(12) United States Patent
Sellman et al.

(10) Patent No.: US 12,349,926 B2
(45) Date of Patent: Jul. 8, 2025

(54) PATIENT-SPECIFIC ANKLE GUIDE SYSTEMS AND METHODS

(71) Applicant: Stryker European Operations Limited, Carrigtwohill (IE)

(72) Inventors: Ryan Sellman, Carlisle, PA (US); David Barry, New York, NY (US)

(73) Assignee: Stryker European Operations Limited, Carrigtwohill (IE)

(*) Notice: Subject to any disclaimer, the term of this patent is extended or adjusted under 35 U.S.C. 154(b) by 698 days.

(21) Appl. No.: 17/187,946

(22) Filed: Mar. 1, 2021

(65) Prior Publication Data

US 2021/0282790 A1    Sep. 16, 2021

Related U.S. Application Data

(60) Provisional application No. 62/987,929, filed on Mar. 11, 2020.

(51) Int. Cl.
   *A61B 17/15* (2006.01)
   *A61B 17/17* (2006.01)

(52) U.S. Cl.
   CPC .......... *A61B 17/15* (2013.01); *A61B 17/1775* (2016.11)

(58) Field of Classification Search
   CPC .......... A61B 17/15–158; A61B 17/75
   See application file for complete search history.

(56) References Cited

U.S. PATENT DOCUMENTS

| | | | |
|---|---|---|---|
| 5,938,665 A * | 8/1999 | Martin | A61B 17/15 606/88 |
| 6,648,894 B2 * | 11/2003 | Abdelgany | A61F 2/4644 606/53 |
| 6,875,236 B2 | 4/2005 | Reiley | |
| 7,618,451 B2 | 11/2009 | Berez et al. | |
| 7,628,793 B2 * | 12/2009 | Calton | A61B 17/155 606/88 |
| 7,799,077 B2 | 9/2010 | Lang et al. | |
| 8,062,302 B2 | 11/2011 | Lang et al. | |
| 8,175,683 B2 | 5/2012 | Roose | |

(Continued)

FOREIGN PATENT DOCUMENTS

| | | |
|---|---|---|
| WO | 2009158522 A1 | 12/2009 |
| WO | 2020239909 A2 | 12/2020 |

OTHER PUBLICATIONS

European Search Report for EP21161696 issued Jul. 9, 2021; 2 pages.

(Continued)

*Primary Examiner* — Zade Coley

(74) *Attorney, Agent, or Firm* — Lerner David LLP

(57) ABSTRACT

The disclosure includes devices for assisting in performing an ankle arthroplasty on a non-resected bone surface of a tibia and/or a talus. The devices may include patient-specific mating surfaces configured to engage the non-resected bone surface in a single relative position relative to the non-resected bone surface. The patient specific nature of the mating surface portion may be generated in the devices prior to the devices being brought into contact with the bone. The devices may include various cutting guides and holes for receiving fasteners to fasten the devices to the bone. The devices may include various features to enhance the stability and/or surface area contact between the devices and the bones.

15 Claims, 42 Drawing Sheets

(56) References Cited

U.S. PATENT DOCUMENTS

| | | | |
|---|---|---|---|
| 8,337,503 B2 * | 12/2012 | Lian | A61B 17/15 |
| | | | 606/87 |
| 8,444,651 B2 | 5/2013 | Kunz et al. | |
| 8,460,304 B2 | 6/2013 | Fitz et al. | |
| 8,475,463 B2 | 7/2013 | Lian | |
| 8,551,103 B2 | 10/2013 | Fitz et al. | |
| 8,562,611 B2 | 10/2013 | Fitz et al. | |
| 8,617,172 B2 | 12/2013 | Fitz et al. | |
| 8,768,028 B2 | 7/2014 | Lang et al. | |
| 8,951,259 B2 | 2/2015 | Fitz et al. | |
| 9,072,531 B2 | 7/2015 | Fitz et al. | |
| 9,095,439 B2 | 8/2015 | Lian | |
| 9,125,672 B2 | 9/2015 | Fitz et al. | |
| 9,125,673 B2 | 9/2015 | Fitz et al. | |
| 9,539,044 B2 | 1/2017 | Lian | |
| 9,730,714 B2 | 8/2017 | Lian | |
| 9,901,353 B2 * | 2/2018 | Carroll | A61B 17/157 |
| 9,993,254 B2 * | 6/2018 | Loring | A61F 2/46 |
| 10,363,053 B2 | 7/2019 | Lian | |
| 2002/0055744 A1 * | 5/2002 | Reiley | A61B 17/1775 |
| | | | 623/21.18 |
| 2007/0100346 A1 * | 5/2007 | Wyss | A61B 17/15 |
| | | | 606/87 |
| 2012/0130376 A1 * | 5/2012 | Loring | A61F 2/4202 |
| | | | 606/90 |
| 2012/0239045 A1 | 9/2012 | Li | |
| 2012/0271314 A1 | 10/2012 | Stemniski et al. | |
| 2013/0026206 A1 * | 1/2013 | Fox | A61B 17/0682 |
| | | | 227/176.1 |
| 2016/0135815 A1 * | 5/2016 | Loring | A61B 17/1739 |
| | | | 606/87 |
| 2017/0027589 A1 * | 2/2017 | Loring | A61B 17/1775 |
| 2018/0289380 A1 | 10/2018 | Mauldin et al. | |
| 2020/0085452 A1 | 3/2020 | Siegler | |

OTHER PUBLICATIONS

Extended European Search Report issued in Appln. No. 23190476.4 mailed Nov. 30, 2023 (8 pages).

* cited by examiner

Alignment Rod

Saw Blade

PATIENT-SPECIFIC ANKLE GUIDE SYSTEMS AND METHODS

CROSS-REFERENCE TO RELATED APPLICATIONS

This application claims the benefit of the filing date of U.S. Provisional Patent Application No. 62/987,929, filed Mar. 11, 2020, the disclosure of which is hereby incorporated by reference herein.

TECHNICAL FIELD

This disclosure is related to systems and methods to facilitate total ankle arthroplasty ("TAA") procedures, and, in particular, patient-specific ankle cutting guide systems and methods.

BACKGROUND OF THE DISCLOSURE

For patients with damaged or otherwise malformed ankle joints, for example due to arthritis or a bone fracture, TAA, also known as total ankle replacement ("TAR"), is being increasingly performed in lieu of ankle fusion procedures. A TAA procedure may include resecting a portion of the patient's distal tibia and/or a portion of the patient's proximal talus and replacing the resected bone with prosthetic components. The accuracy with which the bone resections are made may play an important role in the success of the entire TAA procedure as well as the correct placement of implant components after the bones are resected. The ability for a surgeon to make accurate cuts may be hampered at least in part due to the small size of the operative area in TAA procedures with relatively little space for visualization and surgical instrumentation. Thus, improvements in apparatus and methods to facilitate TAA procedures are desired.

BRIEF SUMMARY

According to one aspect of the disclosure, a device for assisting in performing an ankle arthroplasty on a non-resected bone surface of a tibia includes a posterior surface having a mating surface configured to engage the non-resected bone surface of the tibia in a matching manner on account of a patient-specific nature of the mating surface. The matching manner may register a single relative position of the mating surface relative to the non-resected bone surface of the tibia, and the patient specific nature of the mating surface portion may have been generated in the device prior to the device being brought into contact with the bone surface of the tibia or employed in the arthroplasty. A first guide member may define a transverse cutting instrument guide slot and may have an anterior entrance and a posterior exit. The transverse guide slot may be configured to guide a cutting instrument along a transverse planar guide surface that is substantially orthogonal to a tibial mechanical axis of the tibia when the non-resected tibia surface is engaged to the mating surface in the matching manner. The term "substantially orthogonal" is used because the cut plane may be slightly angled relative to the tibial mechanical axis to accommodate the particular patient's anatomy or to correct a deformity. A second guide member may be coupled to the first guide member. The second guide member may define an angled guide surface angled obliquely to the transverse guide slot. The mating surface may have a first curvature that is curved posteriorly from a central area of the mating surface toward a medial and a lateral edge of the mating surface so that the central area of the mating surface is positioned anterior to the medial and lateral edges of the mating surface.

When in contact with the non-resected bone surface, the first curvature of the mating surface may at least partially wrap around the non-resected bone surface in a medial-to-lateral direction. The mating surface may have a second curvature that is curved posteriorly from the central area of the mating surface toward a superior and an inferior edge of the mating surface so that the central area of the mating surface is positioned anterior to the superior and inferior edges of the mating surface. When in contact with the non-resected bone surface, the second curvature of the mating surface may at least partially wrap around the non-resected bone surface in a superior-to-inferior direction. The mating surface may include an extension portion that extends both inferior and medial of the first guide member, and medial of the second guide member, and the extension portion may be positioned for contacting a medial malleolus of the patient. The device may include a first cylindrical member defining a first pin hole and a second cylindrical member defining a second pin hole. The first and second pin holes may be sized to receive first and second fastening members therethrough, the first and second cylindrical members positioned superior to the first guide member, although in other embodiments the first and second pin holes may be positioned inferior to the first guide member. The first guide member may define a third pin hole at a medial end of the transverse slot and a fourth pin hole at a lateral end of the transverse slot. The device may include a plurality of openings extending from an anterior surface of the device to the posterior surface of the device so that, when the mating surface is engaged with the non-resected bone surface of the tibia, the tibia is visible through the plurality of openings. The transverse guide slot may be defined between a top wall and a bottom wall, the top and bottom walls each having a plurality of peaks and a plurality of troughs. Each peak of the top wall may be aligned in a superior-to-inferior direction with a corresponding trough in the bottom wall, and each peak of the bottom wall may be aligned in the superior-to-inferior direction with a corresponding trough of the top wall. The first guide member may include a channel extending therethrough for receiving an alignment rod, the channel extending orthogonal to the transverse guide slot. The device may also include a rotational alignment sight. The rotational alignment sight may include a projection and an alignment window. When the device is coupled to the tibia, a desired rotational position of the tibia may be indicated when the projection aligns with the alignment window.

According to a further aspect of the disclosure, a device for assisting in performing an ankle arthroplasty on a non-resected bone surface of a talus includes a paddle member having a first mating surface configured to engage the non-resected bone surface of the talus in a first matching manner on account of a patient-specific nature of the first mating surface. The first matching manner may register a single relative position of the first mating surface relative to the non-resected bone surface of the talus, the patient specific nature of the first mating surface having been generated in the device prior to the device being brought into contact with the bone surface of the talus or employed in the arthroplasty. However, in some embodiments, this paddle member may be omitted. A first guide member may define a transverse cutting instrument guide slot and may have an anterior entrance and a posterior exit, wherein the transverse guide slot is configured to guide a cutting instrument along a transverse planar guide surface that is substantially orthogonal to a tibial mechanical axis of the tibia when the non-resected talus surface is engaged to the mating surface in the first matching manner. Again, the term "substantially orthogonal" is used because the cut plane may be slightly angled relative to the tibial mechanical axis to accommodate the particular patient's anatomy or to correct a deformity. A stabilizer member may have a second mating surface configured to engage the non-resected bone surface of the talus in a second matching manner on account of a patient-specific nature of the second mating surface. The second matching manner may register a single relative position of the second mating surface relative to the non-resected bone surface of the talus, the patient specific nature of the second mating surface having been generated in the device prior to the device being brought into contact with the bone surface of the talus or employed in the arthroplasty. The first guide member may be positioned inferior to the paddle member, and the stabilizer member may be positioned inferior to the first guide member.

The first mating surface of the paddle member may be positioned on a posterior and inferior end of the paddle member. The paddle member may include an angled pin hole extending at an oblique angle to the transverse planar guide surface. The stabilizer member may have a medial wing portion and a lateral wing portion, the second mating surface of the stabilizer member being positioned on the medial and lateral wing portions. The stabilizer member may have a first rail and a second rail each extending in an anterior-to-posterior direction, the second mating surface of the stabilizer member being positioned on inferior surfaces of the first rail and the second rail. The device may include a first cylindrical member defining a first pin hole and a second cylindrical member defining a second pin hole, the first and second pin holes sized to receive first and second fastening members therethrough, the first and second cylindrical members positioned inferior to the first guide member. The first guide member may define a third pin hole at a medial end of the guide slot and a fourth pin hole at a lateral end of the guide slot. The first cylindrical member may be positioned a first distance inferior to the first guide member, and the second cylindrical member may be positioned a second distance inferior to the first guide member, the second distance being greater than the first distance. The first guide member may include a channel extending therethrough for receiving an alignment rod, the channel extending orthogonal to the transverse guide slot. The device may include a first cylindrical member defining a first pin hole and a second cylindrical member defining a second pin hole, the first and second pin holes sized to receive first and second fastening members therethrough, the first and second cylindrical members coupled to the first guide member by an extension member, the extension member including a channel extending therethrough for receiving an alignment rod, the channel extending in an anterior-to-posterior direction parallel to the transverse planar guide surface.

According to another aspect of the disclosure, a device for assisting in performing an ankle arthroplasty on a non-resected bone surface includes a posterior surface having a mating surface configured to engage the non-resected bone surface in a matching manner on account of a patient-specific nature of the mating surface. The matching manner may register a single relative position of the mating surface relative to the non-resected bone surface. The patient specific nature of the mating surface portion may have been generated in the device prior to the device being brought into contact with the bone surface or employed in the arthro-plasty. The device may include a cutting instrument guide slot defined by the device and having an anterior entrance and a posterior exit. When the mating surface is engaged to the non-resected bone surface, a center portion of the posterior exit of the guide slot may be positioned a first distance from the non-resected bone surface. The bone surface may be a surface of a tibia, and the guide slot may form a first planar guide surface that is substantially orthogonal to a tibial mechanical axis of the tibia when the non-resected tibia surface is engaged to the mating surface in the matching manner. The device may further define an open viewing window separating the posterior surface into proximal and distal portions. The open viewing window may further separate the posterior surface portion into medial and lateral portions. The device may further include a second planar cutting surface angled obliquely to the guide slot. The anterior entrance of the guide slot may be open at a medial end so that the guide slot freely transitions into the second planar cutting surface. The anterior entrance of the guide slot may be closed at a medial end by a connection portion extending from the planar cutting surface. The device may further include first and second guide holes configured to receive fixation pins through the device, the first and second guide holes each defining axes that are parallel to one another.

According to another embodiment of the disclosure, a device for assisting in performing an ankle arthroplasty on a non-resected bone surface of a tibia includes a posterior surface having a mating surface configured to engage the non-resected bone surface of the tibia in a matching manner on account of a patient-specific nature of the mating surface. The matching manner may register a single relative position of the mating surface relative to the non-resected bone surface of the tibia. The patient specific nature of the mating surface portion may have been generated in the device prior to the device being brought into contact with the bone surface of the tibia or employed in the arthroplasty. A cutting instrument guide slot may be defined by the device and may have an anterior entrance and a posterior exit. The guide slot may form a first planar guide surface that is substantially orthogonal to a tibial mechanical axis of the tibia when the non-resected tibia surface is engaged to the mating surface in the matching manner. A cutting guide member may be adapted to couple to the guide slot, the cutting guide member defining a second planar guide surface angled obliquely to the first planar guide surface. The cutting guide member may be adapted to be hingedly coupled to the guide slot. The cutting guide member may be formed of a metallic material. The cutting guide member may include a hinge portion and a flange portion, the flange portion defining the second planar guide surface. The hinge portion may include a first pin hole extending therethrough. A medial end of the guide slot may define a second pin hole, the first and second pin holes being coaxially aligned when the cutting guide member is coupled to the guide slot.

DETAILED DESCRIPTION OF THE DISCLOSURE

In the present disclosure, the term proximal generally means closer to the heart and the term distal generally means farther away from the heart. The term posterior means a position towards the rear of the body and the term anterior means a position toward the front of the body. The term superior means a position closer to the head and the term inferior means a position closer to the feet. The term patient-specific as used herein refers to a surface of a device configured to mate with a corresponding anatomical surface in substantially only one position and orientation.

Figure 1:
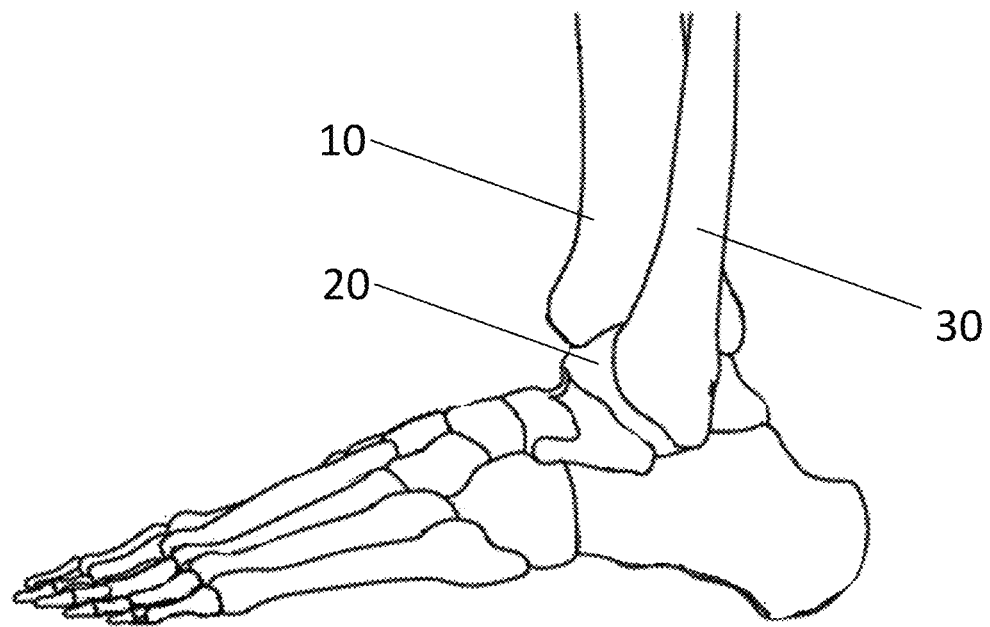
FIG. 1 is a side view of bones of the foot and ankle.
Figure 2:
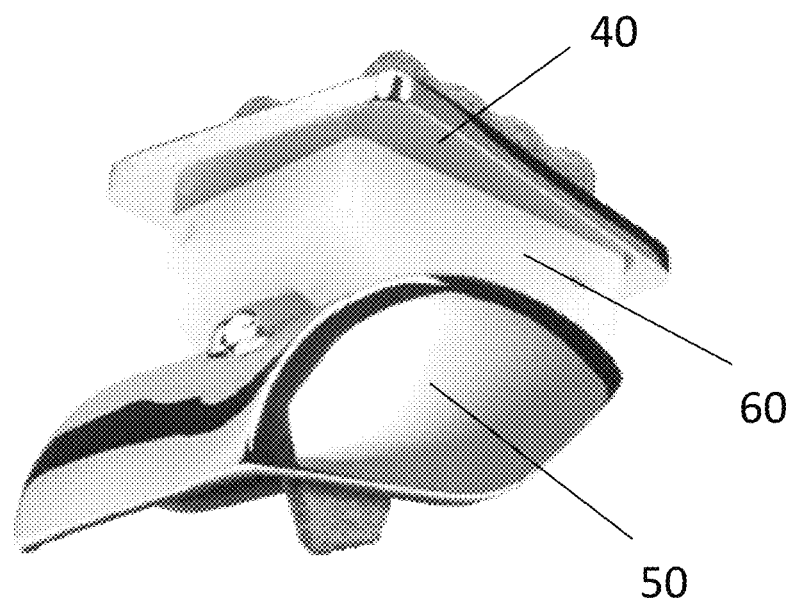
FIG. 2 is a perspective view of components of an ankle joint prosthesis.

FIG. 1 illustrates a simplified side view of the bones of the foot and ankle, including the distal tibia 10, the talus 20, and the fibula 30. In one example, the distal tibia 10 and proximal talus 20 may be arthritic and need replacing, for example with a metal tibial component 40 and a metal talar component 50, respectively, with a plastic mobile bearing 60 (e.g. ultra-high molecular weight polyethylene) interposed between the metal components. An example of such an implant is shown in FIG. 2.

In order to facilitate the surgeon in making accurate resections of the tibia 10 and talus 20, resection guides may be used to guide the cutting instrument in a desired fashion. Such cutting guides, described in greater detail below, may be at least partially patient specific. For example, a surgeon may image the patient's tibia 10 and talus 20 and with the use of specialized software, cutting guides that include bone-contacting surfaces that match (e.g. form a substantial negative of) the topography of the relevant bone may be produced. In this manner, the cutting guides may fit on the corresponding bones in only one (or substantially only one) configuration, helping the surgeon to confirm proper placement. Briefly, computed tomography ("CT") based images may be used to create a 3D model of the patient's anatomy, although other imaging modalities, such as MRI, may be suitable. Other imaging modalities that may be suitable include ultrasound and two-dimensional X-rays that may be morphed into predicted three-dimensional images using statistical shape models, Anatomical alignment can be performed and cutting planes/datum pin placement can be established preoperatively. It should be understood that "datum pin" may refer to a pin that is used in the ankle replacement procedure to place a subsequent instrument called the "datum," with subsequent cut guides being attached to the datum instrument to make chamfer cuts. Patient specific cutting guides or jigs can then be designed from the established cutting planes and datum axis. With the cutting slots (corresponding to the desired cutting planes) and datum pin holes designed, the patient's anatomy can be used to create a matching surface for the guide to fit into place on one specific patient. A Boolean subtraction can be used to create the matching surface of the patient's anatomy that will align the guide intraoperatively. Alternatively, a matching surface can be "grown" or extrapolated from the patient's anatomy. This grown or extrapolated surface may restrict the cut guide to fit in only one area and orientation on one specific patient creating the intraoperative alignment. The patient-specific bone contacting surfaces of the cutting guides are just one feature of the patient specific cutting guides.

Figure 3A:
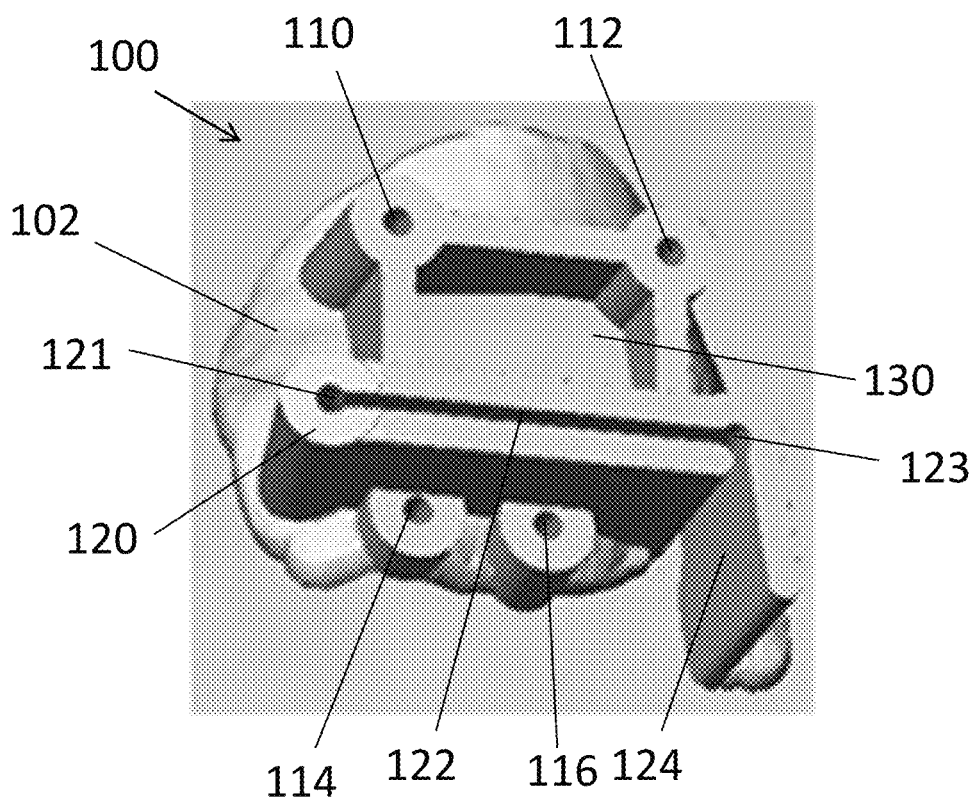
FIG. 3A is a perspective view of a tibia guide according to one aspect of the disclosure.
Figure 3B:
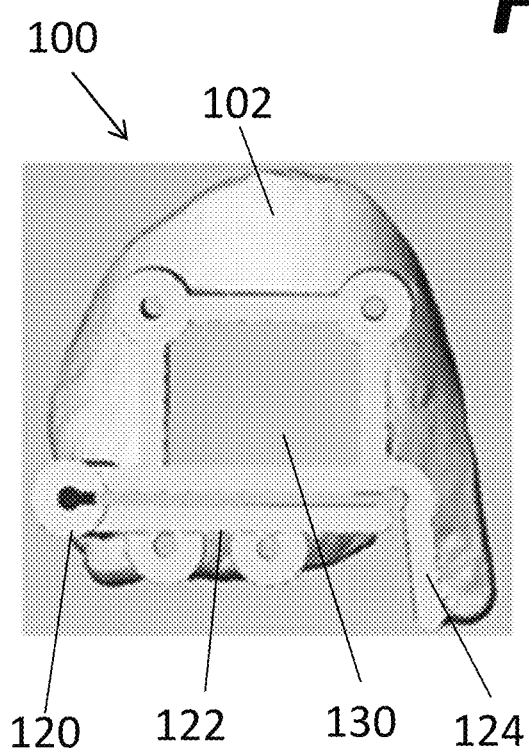
FIG. 3B is a front view of the tibia guide of FIG. 3A.
Figure 3C:
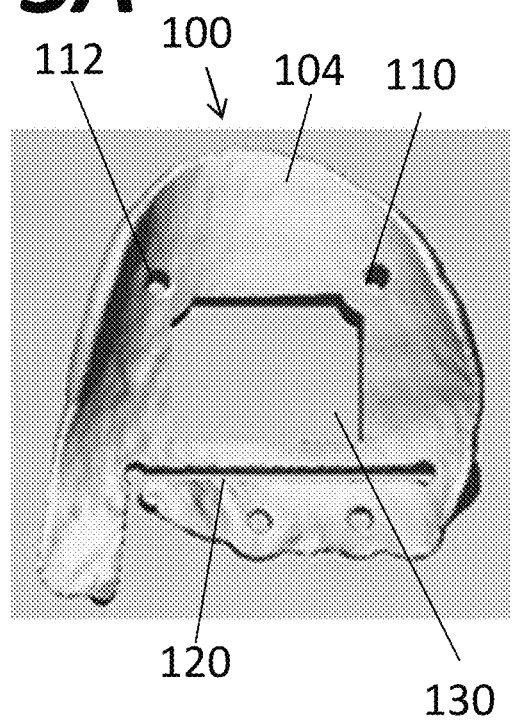
FIG. 3C is a rear view of the tibia guide of FIG. 3A.

For a typical TAA procedure, two patient-specific cutting guides are designed for each patient, including a tibia guide and a talus guide. One example of a patient-specific tibia guide 100 is shown in FIGS. 3A-C. Tibia guide 100 includes an anterior surface 102 (FIGS. 3A-B) and a posterior bone-contacting surface 104 (FIG. 3C). Tibia guide 100 is configured to attach to the anterior surface of the patient's tibia 10. The posterior bone-contacting surface 104 may be keyed to the geometry of the patient's tibia 10 so that tibia guide 100 may fit onto the patient's tibia 10 in only one position and orientation. In addition, the posterior bone-contacting surface 104 may be curved posteriorly from the center toward the medial and lateral edges so that the tibia guide 100 at least partially wraps around the tibia 10 to increase surface area contact between the tibia guide 100 and the tibia 10.

Two pin holes 110 and 112 extend through both the anterior surface 102 and posterior surface 104 of the tibia guide 100 and are sized and shaped to receive fixation pins, or other suitable fixation means, therethrough to fix the tibia guide 100 to the patient's tibia 10. In the illustrated example, pin holes 110 and 112 are positioned superior to a transverse cutting guide slot 120 of the tibia guide 100. Pin hole 110 may be positioned on a lateral side of the tibia guide 100 and pin hole 112 may be positioned on a medial side of the tibia guide 100, with pin holes 110 and 112 being positioned substantially the same height from cutting guide slot 120. Pin holes 110 and 112 may be formed in portions of tibia guide 100 that extend farther anteriorly than other portions of the anterior surface 102 of tibia guide 100, for example in cylindrical or other shaped projections, in order to provide greater surface area for contact between a pin inserted through pin holes 110 and 112 and tibia guide 100. As is described in greater detail below, pin holes 110 and 112 may have positions and orientations that correspond to pin hole positions and orientations of a talus guide 150 so that the talus guide 150 may be slid over the same pins used to hold the tibia guide 100 to the patient's tibia 10 after the tibia guide 100 is removed. Further, pin holes 110 and 112 may have positions and orientations that correspond to pin hole positions and orientations of a universal, non-patient specific cutting guide so that, during the procedure, the surgeon may choose to switch to a universal cutting guide if he or she so desires.

The cutting guide slot 120 may include a first guide portion 122 and a second guide portion 124. The first guide portion 122 may generally consist of two parallel transverse walls defining a first slot therebetween. This first guide portion 122 and corresponding first slot are configured to assist the surgeon in creating a flat transverse cut in the patient's tibia 10. Preferably, the slot 120 of the first guide portion 122 is substantially planar and, when tibia guide 100 is coupled to the tibia 10, the plane of the slot 120 is substantially orthogonal to the mechanical axis of the tibia 10. The second guide portion 124 may consist of a single wall extending at an oblique angle to the first slot, which may in particular be an obtuse angle. However, in some circumstances it may be suitable for the second guide portion 124 to extend perpendicularly relative to the first slot. The second guide portion 124 may define a second slot, although in this instance the second slot is generally open because it is bounded on only one side. This second slot may be configured to assist the surgeon in releasing the resected bone from the medial malleolus and/or from the medial side of the tibia, superior to the medial malleolus. The configuration of the first slot being defined by a fully (or nearly fully) enclosed first guide portion 122 may facilitate a saw blade or other resection tool being directed in a limited intended manner. The configuration of the second slot being open and bounded only by the second guide portion 124 may provide additional freedom of movement that may be necessary for the surgeon to make the cut. Although the second guide portion 124 is being illustrated as being open, in other embodiments (including in other tibia guides described herein that include a generally similar second guide portion), the second guide potion 124 in some embodiments may be closed (or captured), so that one or both of the cutting slots are enclosed or captured. In addition, it should be understood that tibia guide 100 (as well as other tibia guides described herein), need not always be used to resect the medial malleolus, depending on the particular patient and desired surgical procedure.

In addition to defining the first slot, the first guide portion 122 may define a first pin hole 121 at a first end of the first slot relatively far away from the second guide portion 124. The first guide portion 122, either alone or in combination with the second guide portion 124, may define a second pin hole 123 on the opposite side of the first slot from the first pin hole 121. The pin holes 121 and 123 may be configured to receive pins, similar to as described above in connection with pin holes 110 and 112. Pins extending through pin holes 121 and 123 into the patient's tibia 10 may help guide the saw blade, or other cutting tool, as it is inserted through the first and/or second slots and into the patient's tibia 10. In addition, the pins extending through pin holes 121 and 123 may help protect soft tissue, hard tissue, and portions of the cutting guides from being unintentionally cut or otherwise damaged. Further, it should be noted that pin holes 121 and 123, and/or pins extending through these pin holes, may be calibrated with the tibia guide 100, based on information from the prior imaging (e.g. CT scan) so that the pins cannot be over inserted. It should be understood that, for any of the cutting guides described herein, the tool guided by the cutting guide may be any type of saw, including oscillating saws, reciprocating saws, and Precision saws offered by Stryker Corporation.

Still referring to FIGS. 3A-C, the tibia cutting guide 100 may also include two additional pin holes 114 and 116 inferior to first guide portion 122. Pin holes 114 and 116 are preferably positioned a distance from second guide portion 124 so as to avoid any possible interference with the second cut along the second guide portion 124. Although standard pins may be used with pin holes 114 and 116 to provide additional attachment security of tibia cutting guide 100 to the patient's tibia 10, it is envisioned that threaded pins may be used through pin holes 114 and 116. By using threaded pins to help attach the tibia guide 100 to the patient's tibia 10, after both tibial cuts are made, pulling the threaded pins may help remove the portion of the patient's tibia 10 that has been cut completely free from the remainder of the patient's tibia 10.

Figure 5A:
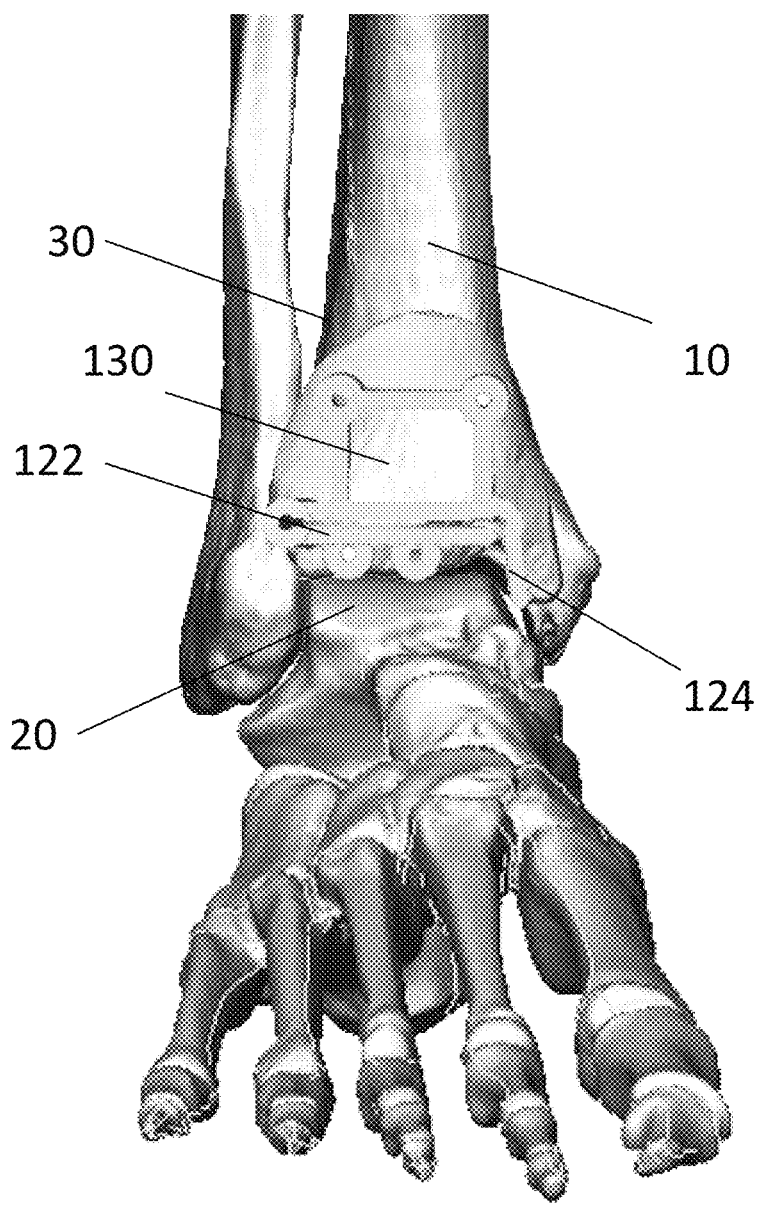
FIGS. 5A-C are various views of the tibia guide of FIG. 3A coupled to the ankle of a patient.
Figure 5B:
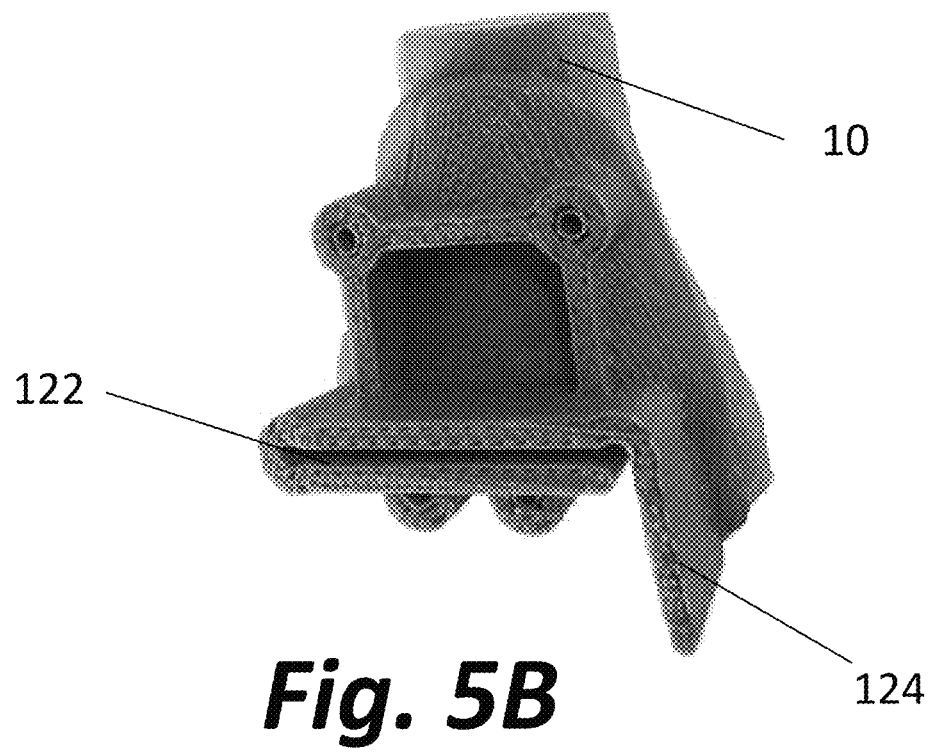
Figure 5C:
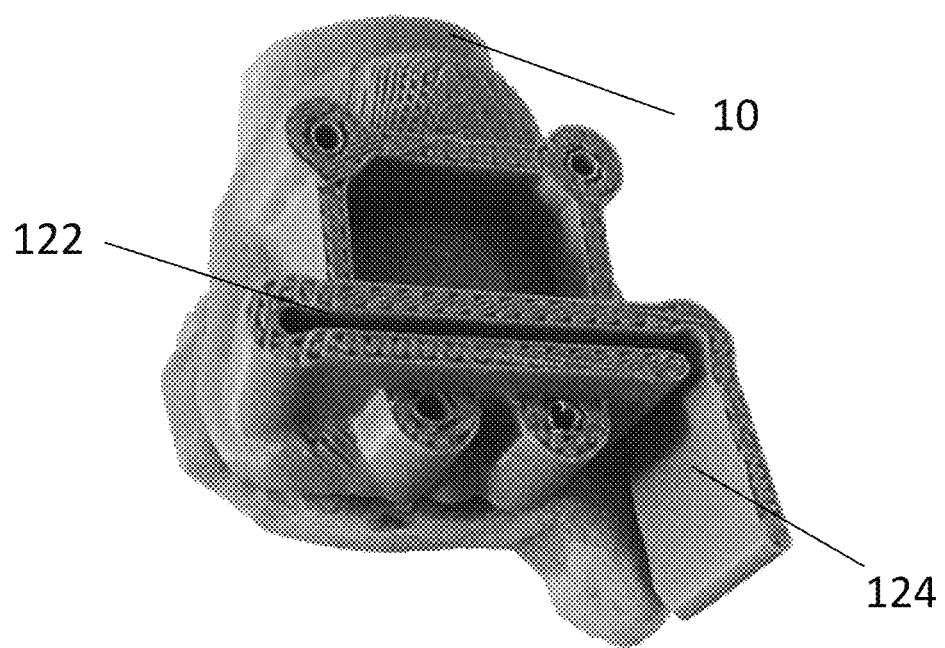

The tibia guide 100 may also include a window 130. Window 130 may facilitate the surgeon in better visualizing the patient's tibia 10 and checking proper fitting between the tibia guide 100 and the patient's tibia 10. Window 130 may generally be defined by a plurality of protruding walls connecting pin hole 110 to pin hole 112, and pin holes 110 and 112 to the superior wall of first guide portion 122. As illustrated, window 130 is generally rectangular, although other window shapes may be suitable. Tibia guide 100 is illustrated positioned on the tibia 10 of a patient, with pins removed for clarity, in FIGS. 5A-C. It should be noted that pin holes 110 and 112 may extend along axes that are parallel to one another, pin holes 121 and 123 may extend along axes that are parallel to one another, and pin holes 114, 116 may extend along axes that are parallel to one another.

Figure 4A:
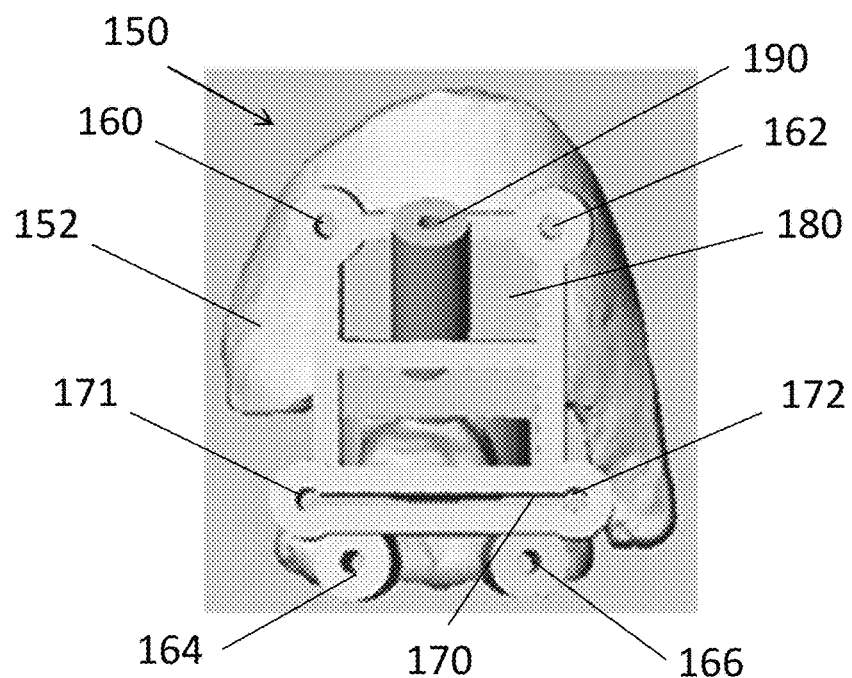
FIG. 4A is a front view of a talus guide according to one aspect of the disclosure.
Figure 4B:
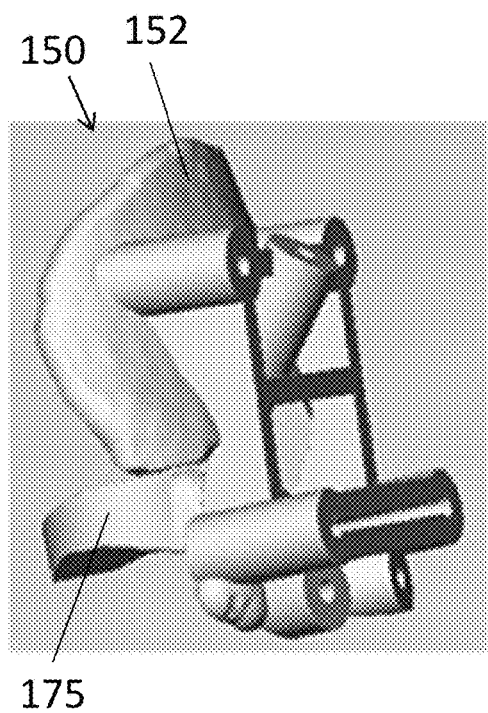
FIG. 4B is a perspective view of the talus guide of FIG. 4A.
Figure 4C:
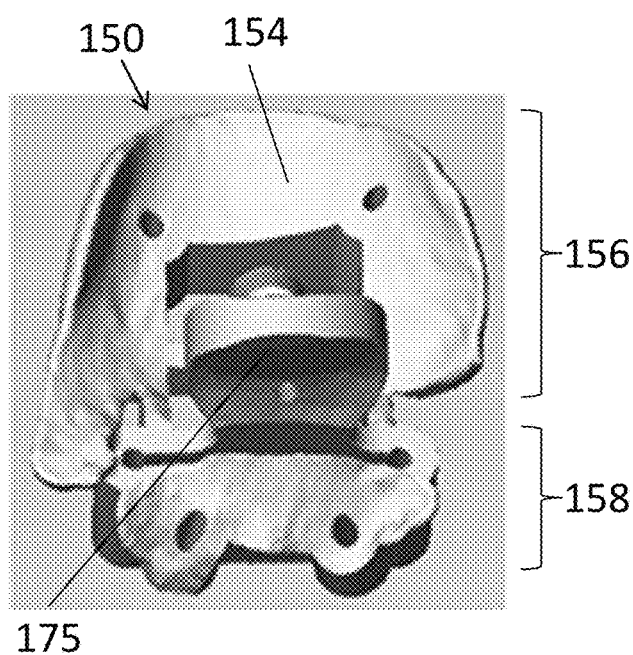
FIG. 4C is a rear view of the talus guide of FIG. 4A.

Now referring to FIGS. 4A-C, an example of a talus guide 150 is illustrated. Talus guide 150 includes an anterior surface 152 (FIGS. 4A-B) and a posterior bone-contacting surface 154 (FIG. 4C). Talus guide 150 may include an upper portion 156 configured to attach to the anterior surface of the patient's tibia 10 and a lower portion 158 configured to attach to the anterior surface of the patient's talus 20. The posterior bone-contacting surfaces 154 of the upper portion 156 and lower portion 158 may be keyed to the geometry of the patient's tibia 10 and talus 20, respectively, so that talus guide 150 may fit onto the patient's tibia 10 and talus 20 in only a single position and orientation. In addition, the posterior bone-contacting surfaces 154 may be curved posteriorly from the center toward the medial and lateral edges so that the talus guide 150 at least partially wraps around the tibia 10 and talus 20 to increase surface area contact between the talus guide 150 and the tibia 10 and talus 20.

Two pin holes 160 and 162 extend through both the anterior surfaces 152 and posterior surfaces 154 of the upper portion 156 of the talus guide 150 and are sized and shaped to receive fixation pins, or other suitable fixation means, therethrough to fix the upper portion 156 of the talus guide 150 to the patient's tibia 10. In the illustrated example, pin holes 160 and 162 are positioned superior to a transverse cutting guide slot 170 of the talus guide 150. Pin hole 160 and may be positioned on a lateral side of the talus guide 150 and pin hole 162 may be positioned on a medial side of the talus guide 150, with pin holes 160 and 162 being positioned substantially the same height from transverse slot 170. As best seen in FIG. 4B, pin holes 160 and 162 may be formed in portions of talus guide 150 that extend farther anteriorly than other portions of the anterior surface 152 of talus guide 150, for example in cylindrical or other shaped projections, in order to provide greater surface area for contact between a pin inserted through pin holes 160 and 162 and talus guide 150. Pin holes 160 and 162 may have the same size, position, and orientation with respect to one another as pin holes 110 and 112 of tibia guide 100 so that, after use and removal of the tibia guide 100, the pin holes 160 and 162 of the talus guide 150 may be slipped over the pins that were previously used with pin holes 110 and 112 of the tibia guide 100.

The transverse slot 170 may be defined by a guide portion generally consisting of two parallel walls defining the transverse slot 170 therebetween. Transverse slot 170 may be configured to assist the surgeon in creating a flat transverse cut in the patient's talus 20. The transverse slot 170 may be fully enclosed to facilitate a saw blade or other resection tool being directed in a limited intended manner. The parallel walls defining the transverse slot 170 may also define a first pin hole 171 on a lateral side of the talus guide 150 and a second pin hole 172 on a medial side of the talus guide 150. The pin holes 171 and 172 may be configured to receive pins, similar to as described above in connection with pin holes 160 and 162. Pins extending through pin holes 171 and 172 and into the patient's talus 20 may help guide the saw blade, or other cutting tool, as it is inserted through the transverse cutting slot 170 and into the patient's talus 20. In addition, the pins extending through pin holes 171 and 172 may help protect soft tissue, hard tissue, and portions of the cutting guide from being unintentionally cut or otherwise damaged.

The talus guide 150 may include a protrusion in the form of a tongue or paddle 175 extending posteriorly from an area of the talus guide 150 between the upper portion 156 and lower portion 158 and superior to the transverse slot 170. The paddle 175 may be configured for insertion between the resected surface of the distal tibia 10 and the unresected proximal surface of the talus 20. Paddle 175 is preferably sized and shaped to provide additional surface area contact between talus guide 150 and the tibia 10 and talus 20, which may better support the foot after the tibia 20 has been cut. This support may be particularly useful during the step of resecting the talus 20 with a blade or other cutting tool through transverse slot 170.

Prior to resecting the talus 20, the patient's foot may be rotated so that the talus 20 is in proper contact with the lower portion 158 of talus guide 150. Once the talus 20 is in the proper position, the surgeon may insert pins through pin holes 164 and 166 and into the properly positioned talus 20. Pin holes 164 and 166 are positioned inferiorly of the transverse cutting slot 170. The talus guide 150 may also include a window 180 similar to window 130. Window 180 may facilitate the surgeon in better visualizing proper contact between the talus guide 150 and the patient's tibia 10 and talus 20. Window 180 may generally be defined by a plurality of protruding walls connecting pin hole 160 to pin hole 162, and pin holes 160 and 162 to the superior wall that defines the transverse slot 170. As illustrated, window 180 is generally rectangular, although other window shapes may be suitable.

Figure 6A:
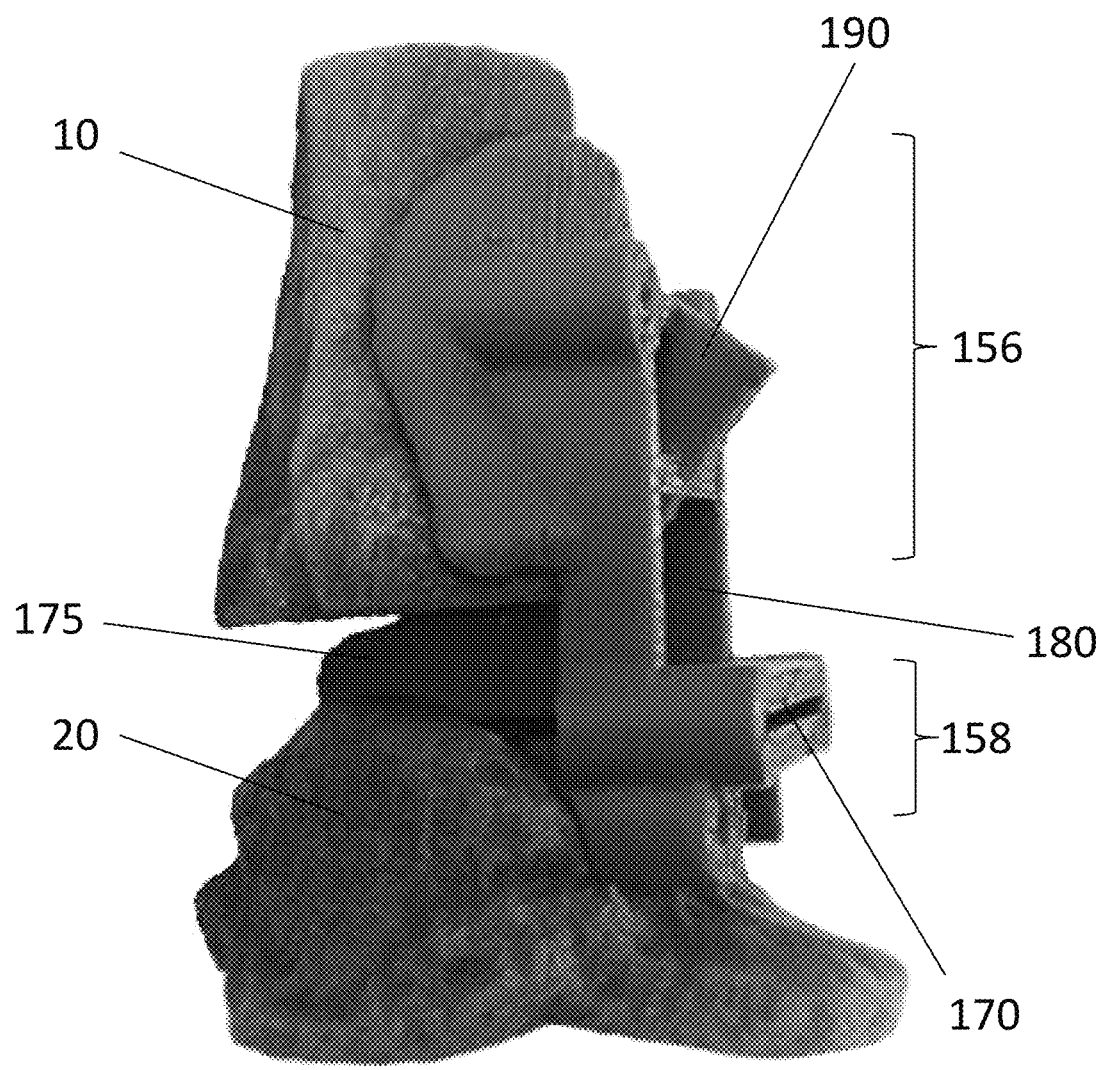
FIGS. 6A-C are various views of the talus guide of FIG. 4A coupled to the ankle of a patient.
Figure 6B:
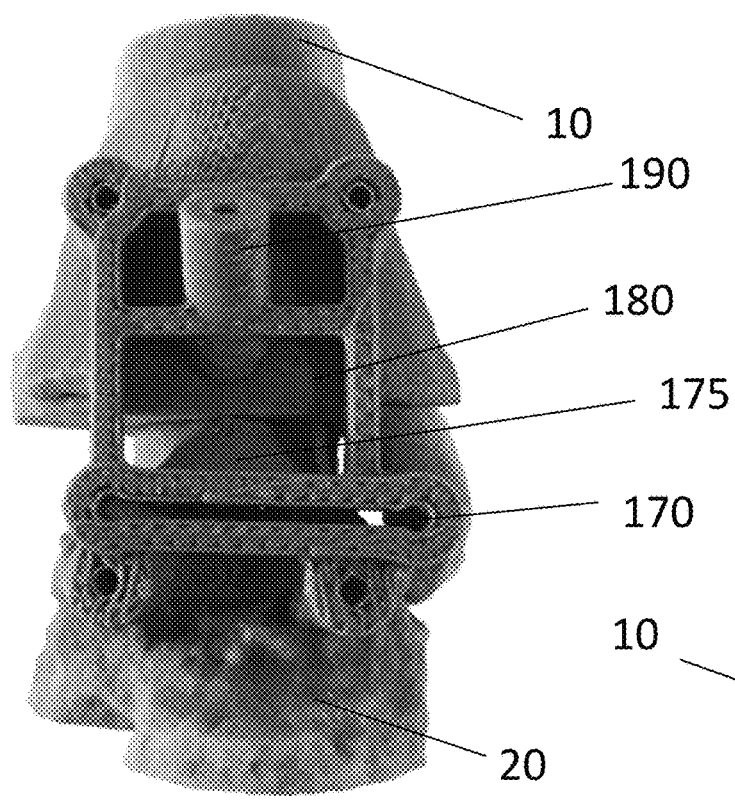
Figure 6C:
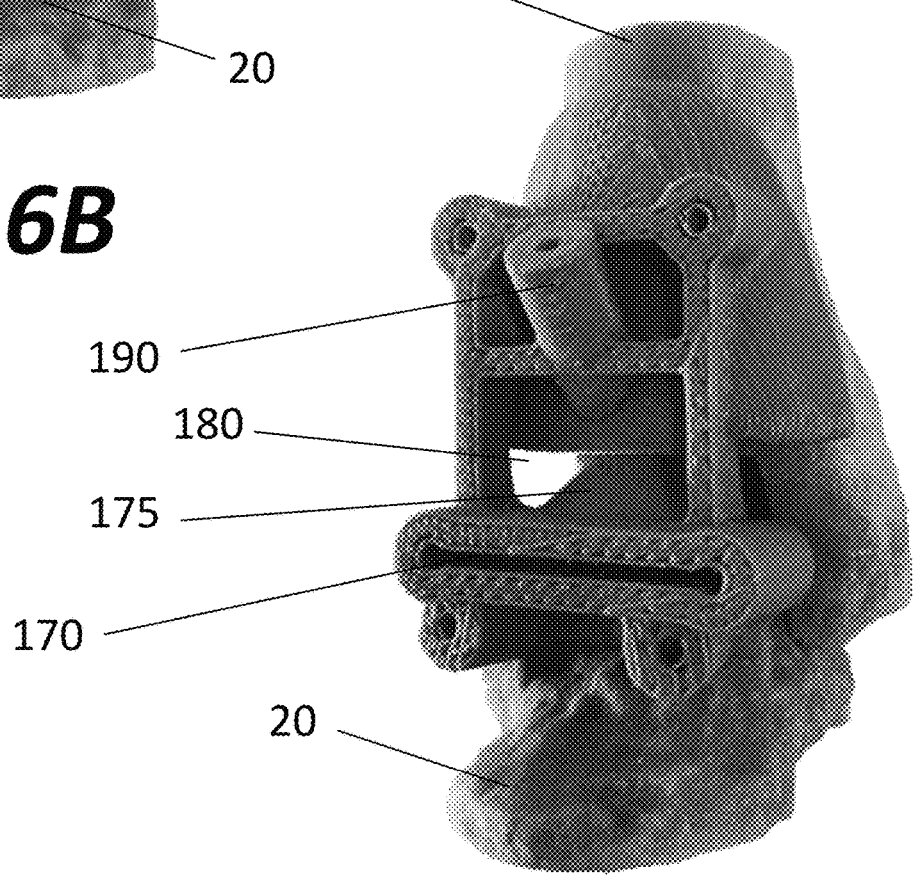

Talus guide 150 may further include an angled pin hole 190 to guide the datum pin into place so the surgeon can attach the existing datum pin cutting guides. In an exemplary TAA procedure, prior to inserting the datum pin, pins in holes 160 and 162 are removed, after the talus 20 is resected, and the patient's foot is plantar flexed to provide the desired insertion position of the datum pin. After the datum pin is in place, the tibia guide 100 and talus guide 150 may be discarded and the TAA procedure continued. Talus guide 150 is illustrated positioned on the tibia 10 and talus 20 of a patient, with pins removed for clarity, in FIGS. 6A-C. Other steps of a TAA procedure that may be used with the cutting guides described herein, including the steps leading up to the use of the guides and the steps following the use of the guides, are provided in U.S. Patent Publication No. 2012/0130376, the disclosure of which is hereby incorporated by reference herein.

Figure 4D:
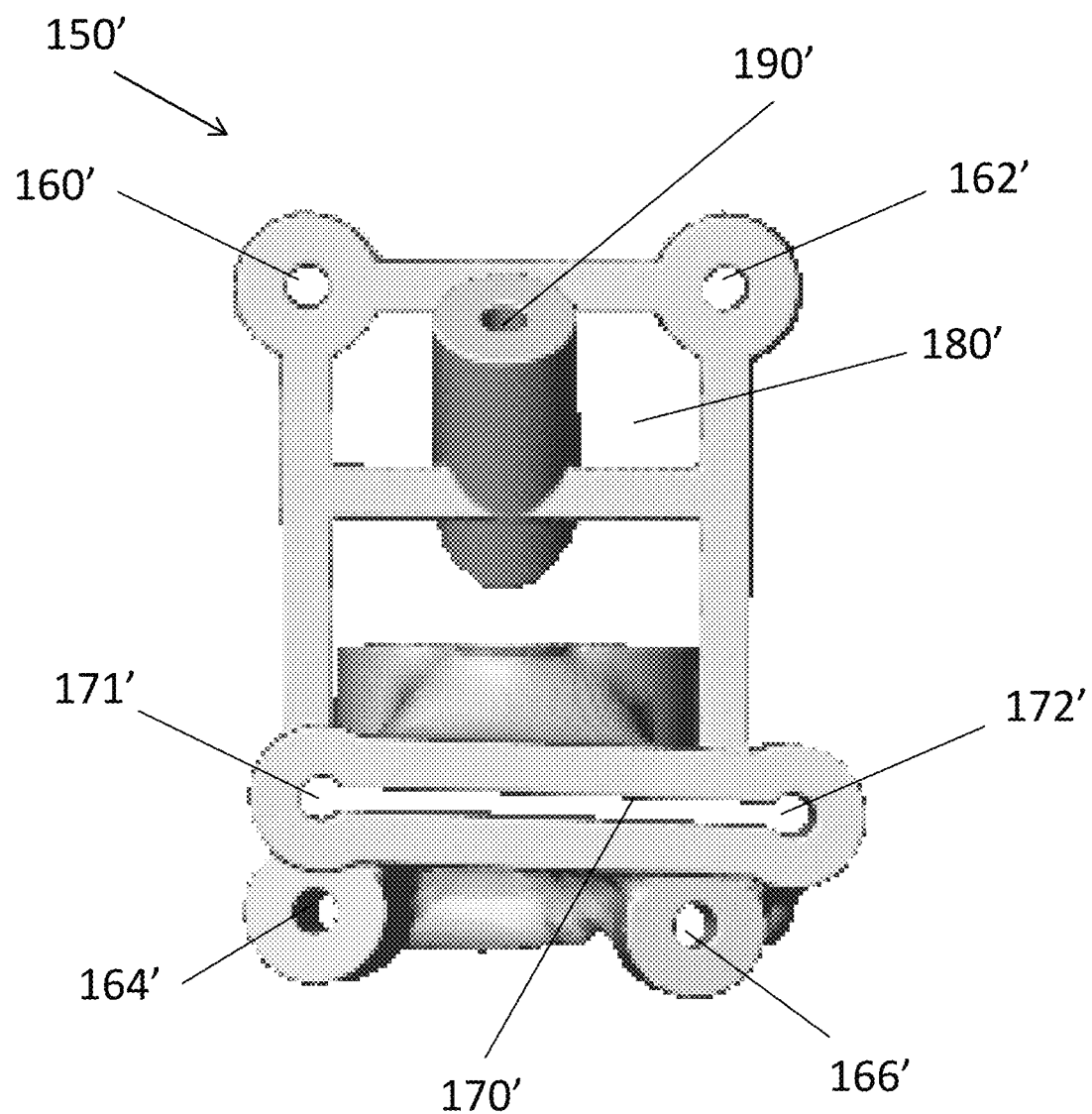
FIG. 4D is a front view of a talus guide according to a second aspect of the disclosure.

FIG. 4D illustrates an alternate version of talus guide 150' in which the upper portion of talus guide 150' does not include a patient-specific tibia contacting surface. The remaining components of talus guide 150', including pin holes 160', 162', 164', 166', window 180', angled pin hole 190', transverse slot 170', and the pin holes 171' and 172' at the opposite ends of the transverse slot 170', are identical to the corresponding features of talus guide 150.

Figure 7A:
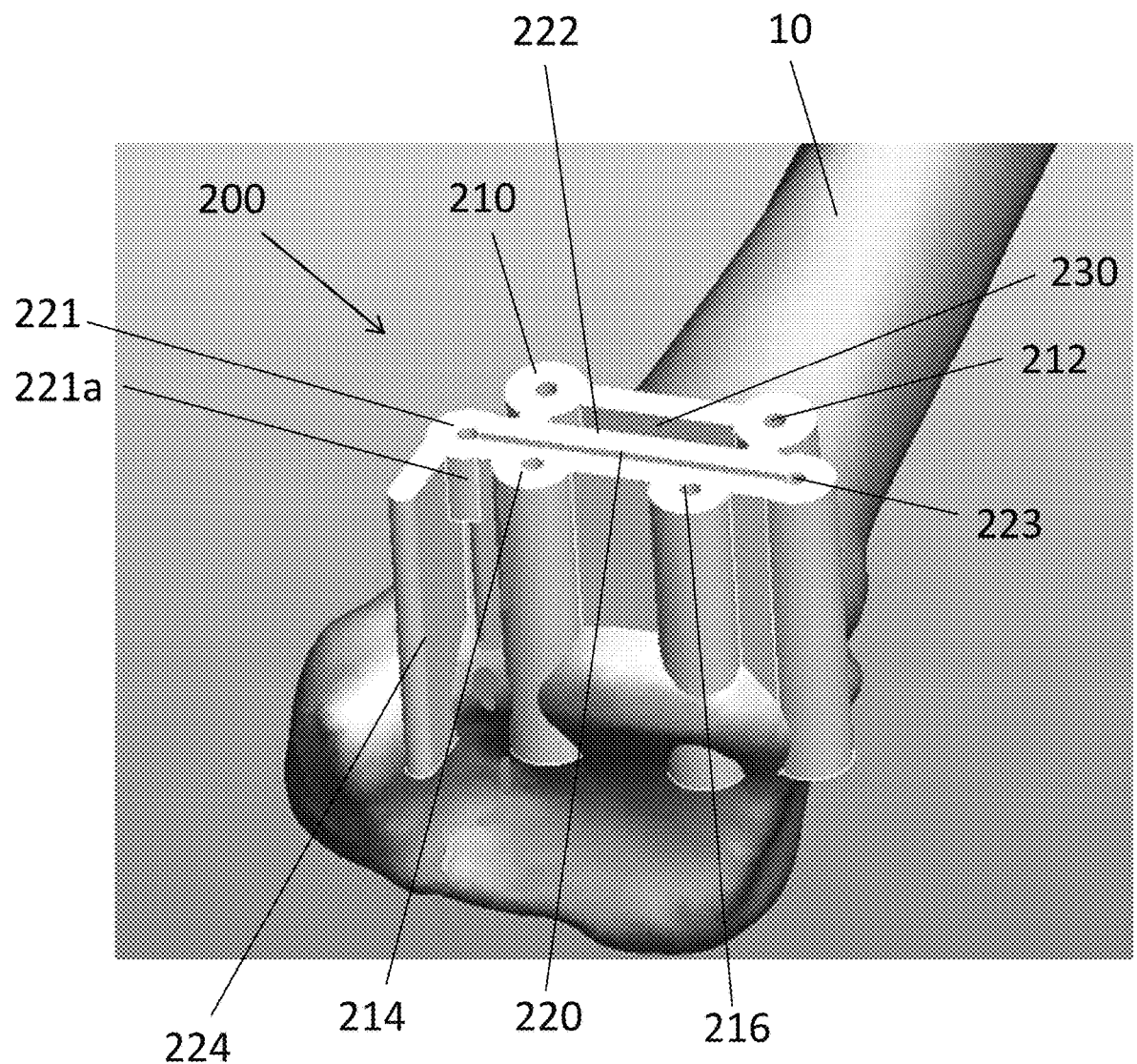
FIGS. 7A-C are various views of a tibia guide according to a second aspect of the disclosure coupled to the tibia of a patient.
Figure 7B:
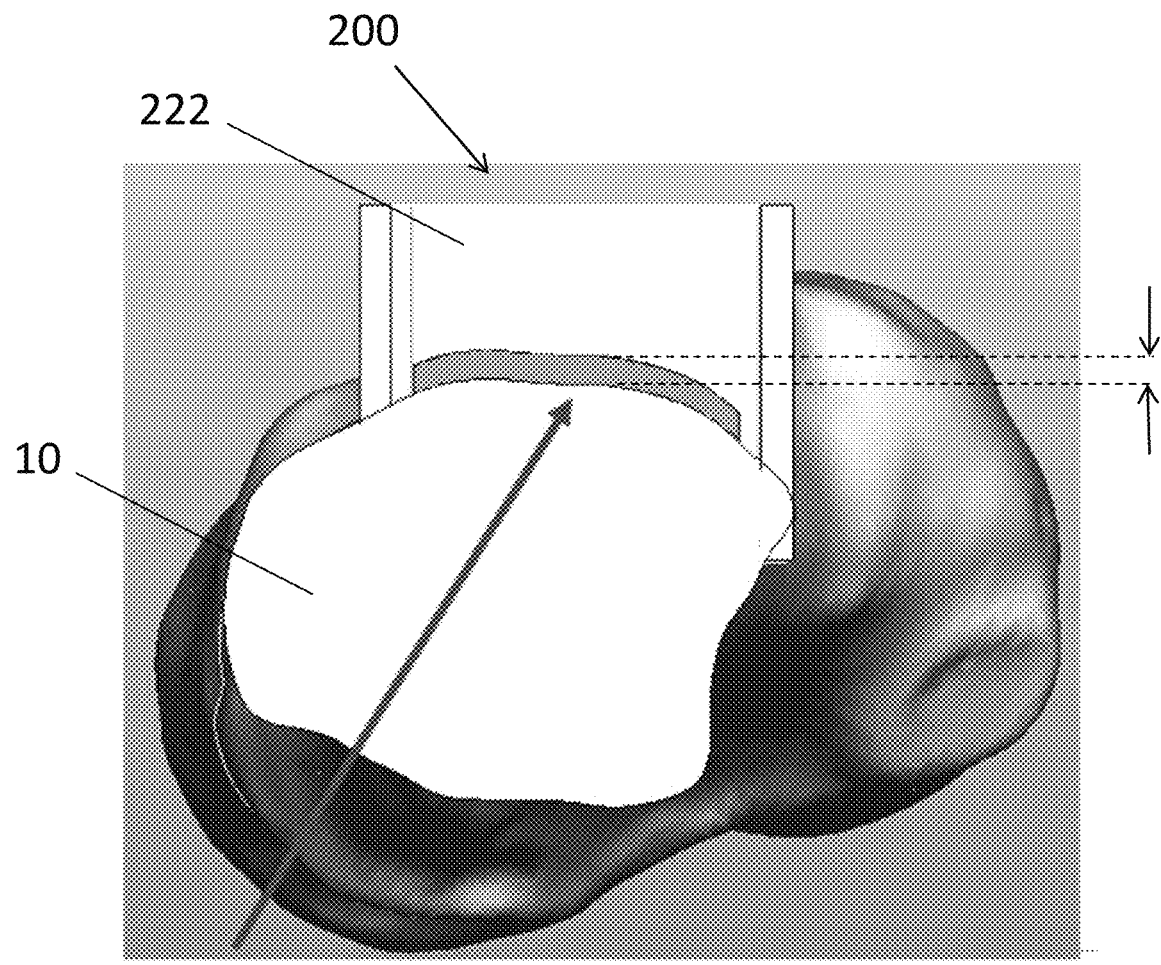
Figure 7C:
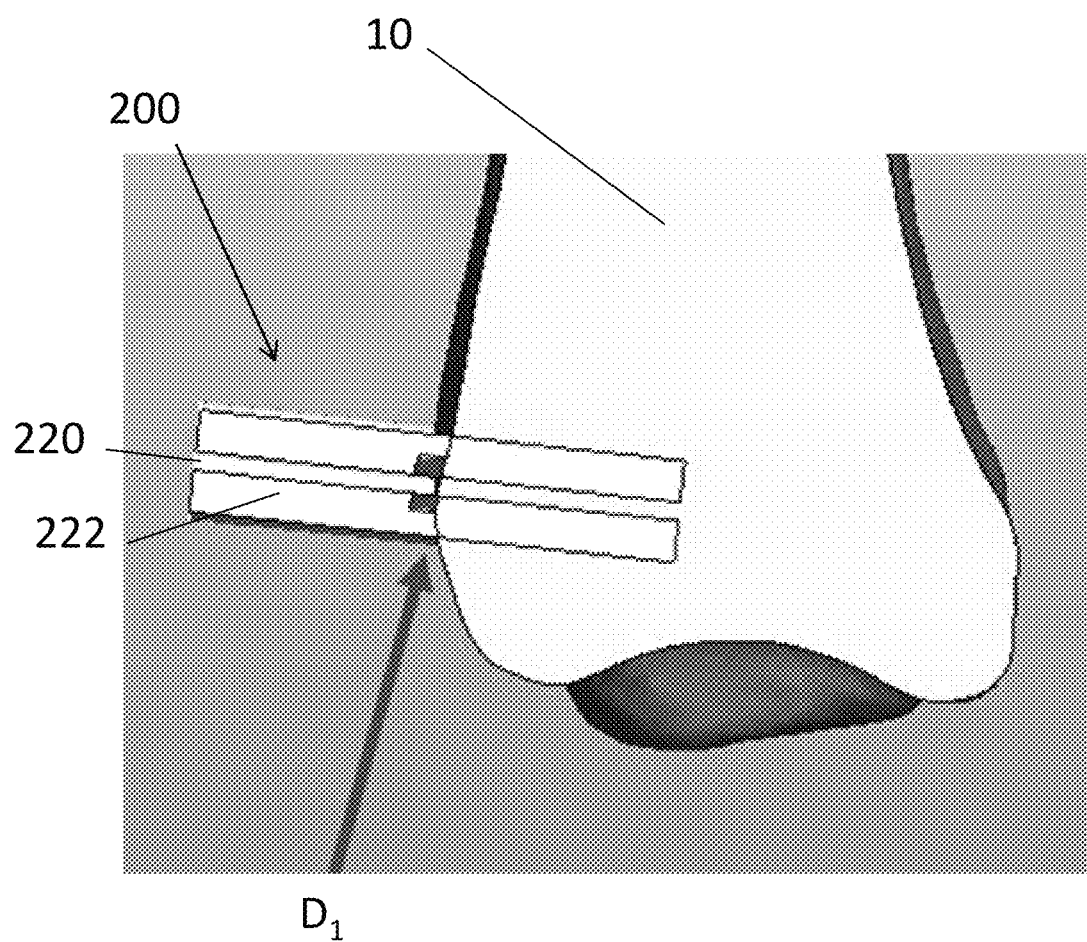

FIGS. 7A-C illustrate a tibia guide 200 that is mostly similar to tibia guide 100 with certain differences. It should be noted that the illustrated tibia guide 100 is for a right foot, whereas the illustrated tibia guide 200 is for a left foot. Further, for purposes of illustration, certain portions of tibia guide 200 are omitted from view, such as the patient specific surfaces and other surfaces that are not part of the cutting slots or pin holes (e.g. the surfaces corresponding to anterior surface 102 and posterior surface 104 of tibia guide 100 are omitted from the illustration of tibia guide 200). As shown in FIG. 7A, tibia guide 200 includes two superior pin holes 210, 212 and two inferior pin holes 214, 216 with a first cutting guide portion 222 and window 230 positioned therebetween. Similar to tibia guide 100, first cutting guide portion 222 defines a transverse slot 220 with a first pin hole 221 and a second pin hole 223 at opposite ends of the transverse slot 220. Also similar to tibia guide 100, tibia guide 200 includes a second guide portion 224 extending obliquely or orthogonally to the transverse cutting slot 220 to assist a surgeon in resecting the medial malleolus. The portions of tibia guide 200 described above may have the same relative positioning and orientation with respect to the corresponding features of tibia guide 100, with the exception that tibia guide 100 is for a right foot whereas tibia guide 200 is for a left foot.

There are a number of differences between tibia guide 100 and tibia guide 200. For example, whereas the transition from the first cutting guide portion 122 to second cutting guide portion 124 is completely open in tibia guide 100, the transition from first cutting guide portion 222 to second cutting guide portion 224 of tibia guide 200 is partially closed. In particular, a connecting portion 221a connects first cutting guide portion 222 to second cutting guide portion 224 so that pin hole 221 is fully enclosed at the anterior end of the guide 200. As illustrated, connecting portion 221a does not extend the full anterior to posterior length of the transition between first cutting guide portion 222 and second cutting guide portion 224. Although the exact length which connecting portion 221a extends in an anterior to posterior direction along the transition between first cutting guide portion 222 and second cutting guide portion 224 may be designed as desired by surgeon or other medical personnel, preferably the length is less than one half, more preferably less than one third, and most preferably one fourth or less the anterior to posterior length of the second cutting guide portion 224. With this closed configuration provided by the connection section 221a, additional strength and rigidity is provided to the transition between the first cutting guide portion 222 and the second cutting guide portion 224. However, the short length of the connecting portion 221a allows the surgeon to resect a significant portion of the medial malleolus. For example, the portion of the medial malleolus posterior to the connecting portion 221a may be resected by guiding a resecting blade or other cutting tool along second cutting guide portion 224, and guiding a cutting portion of the cutting tool to a position posterior to the connecting portion 221a. If connecting portion 221a extended the entire length of the second cutting guide portion 224, a corresponding portion of the medial malleolus would not be easily accessible and it also could be more likely that the tibia guide 200 would be unintentionally cut. It should be understood that after making the transverse cut through cutting slot 220 and the medial malleolus cut along second guide portion 224, a small portion of bone may need to be manually resected after the cutting guide is removed to complete the continuity between the two cuts.

Another difference between tibia guide 100 and tibia guide 200 is that tibia guide 200 includes an offset distance between the transverse cutting slot 220 and the tibia 10 when the tibia guide 200 is coupled to the tibia 10. FIG. 7B illustrates a sectional view of tibia guide 200 coupled to tibia 10 along a plane orthogonal to the longitudinal axis of the tibia 10. FIG. 7C illustrates a sectional view of the tibia guide 200 coupled to tibia 10 along a plane through the longitudinal axis of the tibia 10 extending in an anterior-to-posterior direction. For clarity of illustration, most portions of tibia guide 200 that do not form any part of transverse cutting slot 220 are omitted from FIGS. 7B-C. As shown in FIGS. 7B-C, the posterior surfaces of the walls of first guide portion 222 that define cutting slot 220 are offset a distance $D_1$ from the corresponding surface of the tibia 10 when the tibia guide 200 is coupled to the tibia 10 in an operative condition. In other words, the majority of a center portion of the posterior surface of the first guide portion 222 that defines cutting slot 220 extends anteriorly a distance of $D_1$ compared to the posterior bone-contacting surfaces of tibia guide 200 immediately adjacent the medial and lateral ends of cutting slot 220. This offset distance $D_1$ reduces the amount of debris resulting from the resection blade (or other cutting tool) contacting the tibia guide 200 near the point where the blade enters the tibia 10.

Figure 8A:
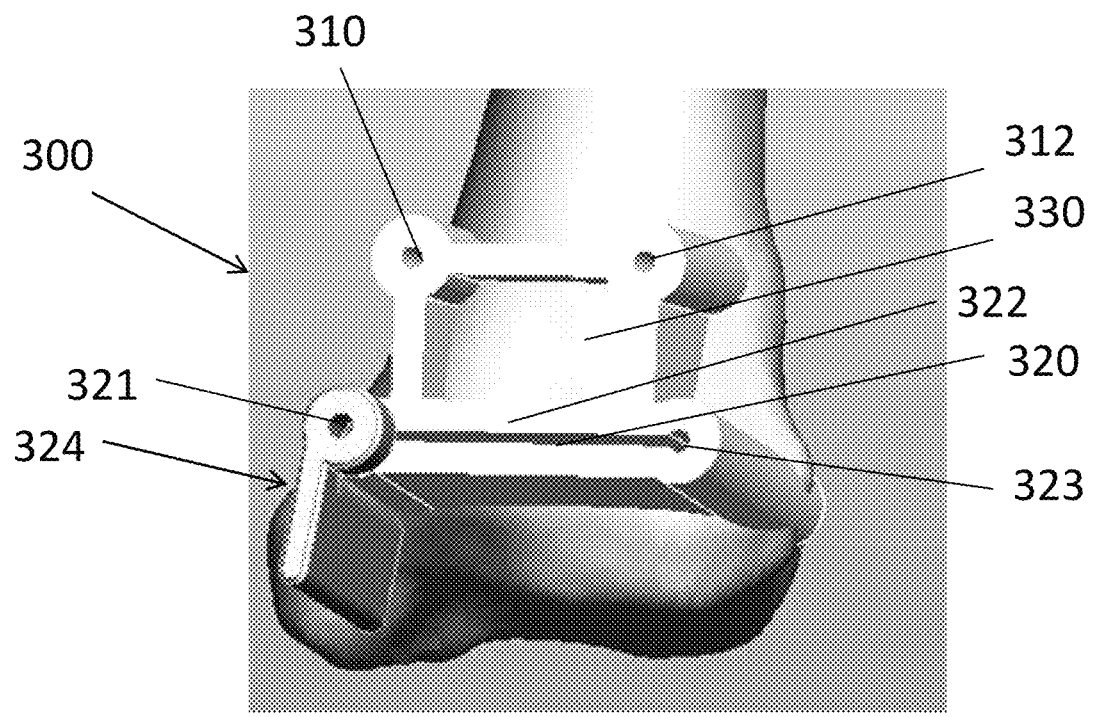
FIGS. 8A-B are various views of a tibia guide according to a third aspect of the disclosure coupled to the tibia of a patient.
Figure 8B:
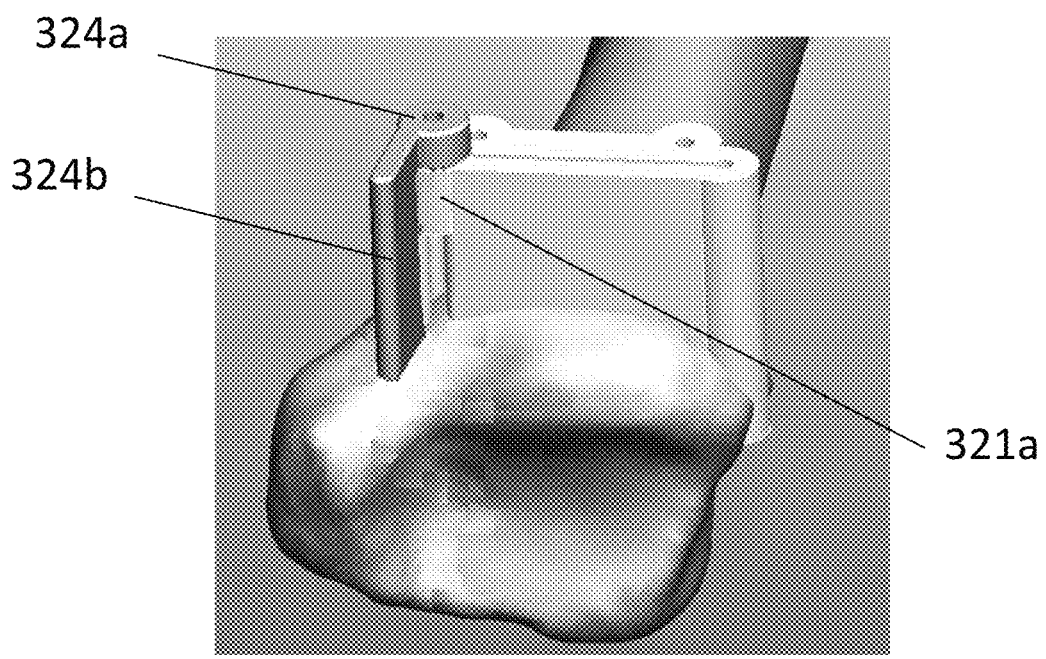

FIGS. 8A-B illustrate a tibia guide 300 that is mostly similar to tibia guide 200 with one difference. For purposes of illustration, certain portions of tibia guide 300 are omitted from view, such as the patient specific surfaces and other surfaces that are not part of the cutting slots or pin holes (e.g. the surfaces corresponding to anterior surface 102 and posterior surface 104 of tibia guide 100 are omitted from the illustration of tibia guide 300). As shown in FIG. 8A, tibia guide 300 includes two superior pin holes 310, 312 and two inferior pin holes (omitted from FIGS. 8A-B) with a first cutting guide portion 322 and window 330 positioned therebetween. Similar to tibia guide 200, first cutting guide portion 322 defines a transverse slot 320 with a first pin hole 321 and a second pin hole 323 at opposite ends of the transverse slot 320.

Tibia guide 300 does not include a second cutting guide portion integral with the tibia guide 300 as shown in tibia guides 100 and 200. Rather, a second guide portion 324 is provided separately and is attachable to tibia guide 300 via pin hole 321. For example, second guide portion 324 may be a metallic hinge type device that may be sterilized and reused for multiple tibia guides 300 corresponding to different patients. In particular, and as best shown in FIG. 8B, second guide portion 324 may include a hinge portion 324a and a flange portion 324b. Hinge portion 324a may include a connecting portion that extends into pin hole 321 to couple second guide portion 324 to tibia guide 300. Preferably, the portion of hinge portion 324a inserted into pin hole 321 does not extend a distance greater than connecting portion 321a (see FIG. 8B). Hinge portion 324a includes a pin hole that is preferably coaxial with pin hole 321 when connected to tibia guide 300. With this configuration, a pin may be inserted through both hinge portion 324a and pin hole 321 to secure the tibia guide 300 to the tibia 10. Alternatively, hinge portion 324a may be coupled to tibia guide 300 by a pin inserted through both the hinge portion 324a and pin hole 321, without any portion of hinge portion 324a extending into pin hole 321. Using a second guide portion 324 that is separate from tibia guide 300 may provide a number of benefits. First, flange 324b, which is intended to guide a saw blade along a cutting path through the medial malleolus, may be positioned at different angles with respect to the transverse cutting slot 320 to give additional freedom to the surgeon. Second, because second cutting guide 324 is made from a material that is sterilizeable, such as a metal suitable for use in surgery, a single second cutting guide 324 may be re-used through multiple procedures, reducing the complexity of designing the remainder of the patient specific tibia guide 300 and correspondingly reducing the costs of producing the tibia guide 300. Third, the use of a harder material such as metal may reduce the likelihood that the cutting saw unintentionally cuts into flange portion 324b as the flange portion 324b guides the direction and position of the saw blade.

Figure 9A:
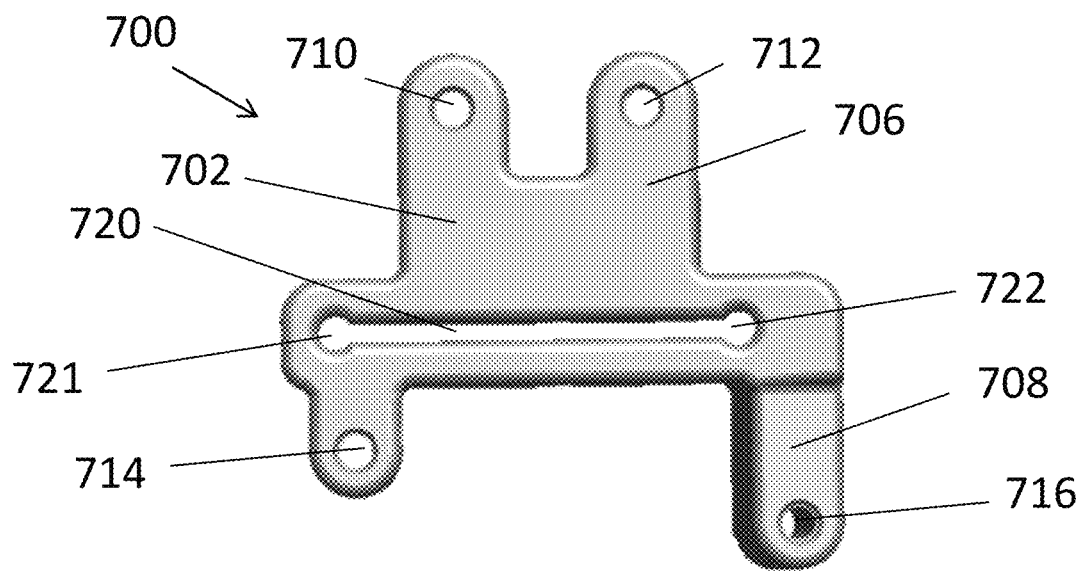
FIG. 9A is a front view of a first talus guide of a two-stage talus guide system.
Figure 9B:
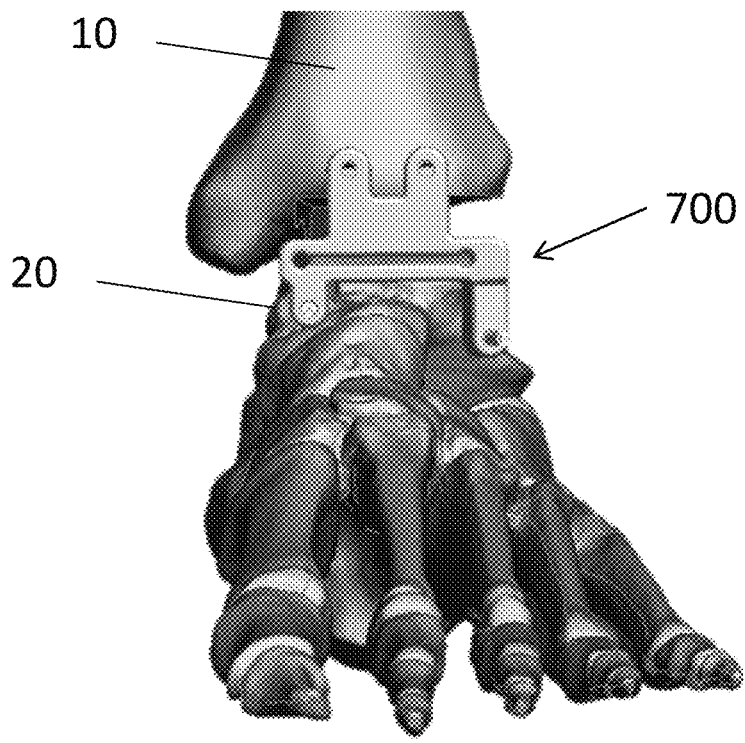
FIGS. 9B-D are various views of the first talus guide of FIG. 9A coupled to an ankle joint.
Figure 9C:
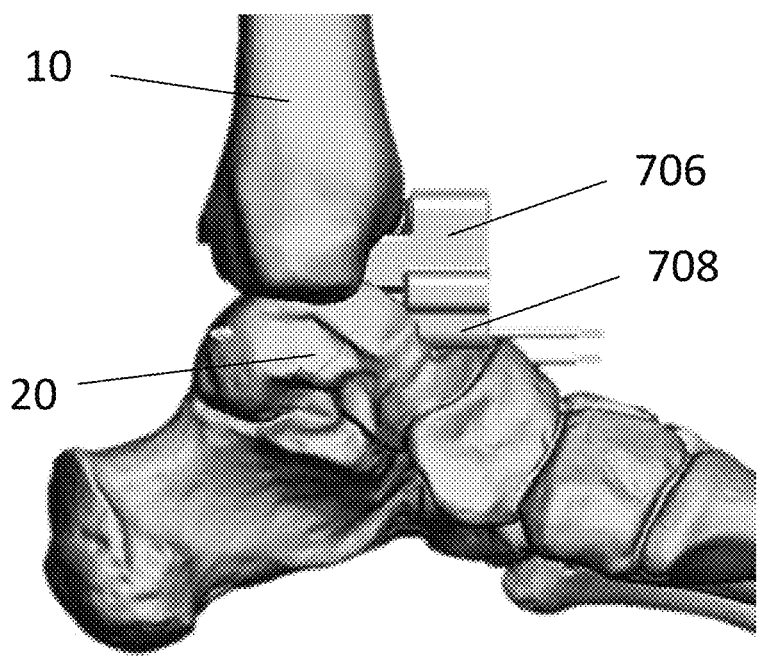
Figure 9D:
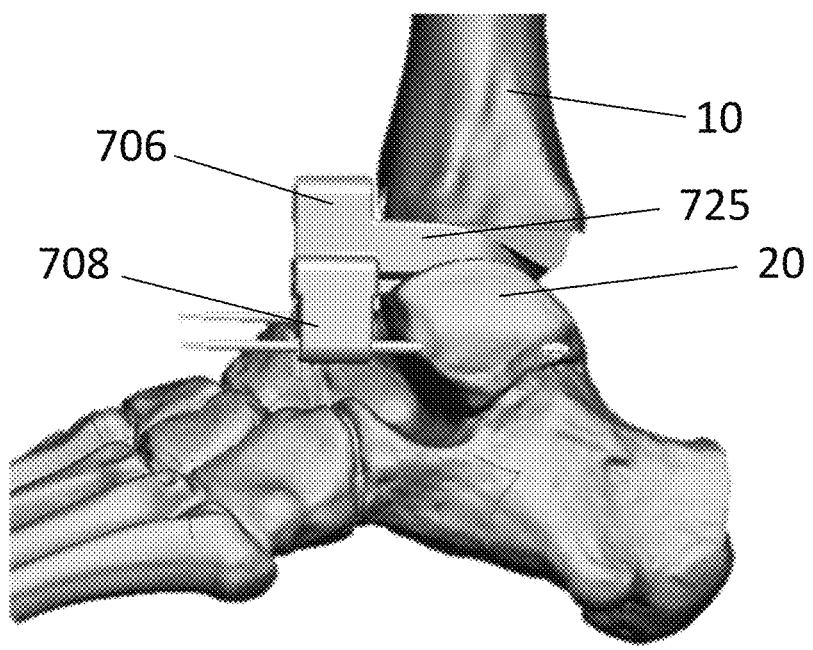

Although the above-described talus guides provide for a single transverse cut, other talus guides may provide for additional cuts. For example, a two-stage talus guide system may provide for a transverse cut of the proximal talus 20 and medial and/or lateral cuts of the talus 20. For example, a first talus guide 700 of a two-part talus guide system is illustrated in FIG. 9A, which may be used after a tibia guide is used to create desired cuts in the distal tibia 10. FIGS. 9B-D illustrate various views of a tibia 10 and talus 20 with the first talus guide 700 coupled thereto, after tibial cuts have been made but before any talus cuts have been made. First talus guide 700 includes an anterior surface 702 and a posterior bone-contacting surface (not labelled in the figures). First talus guide 700 may include an upper portion 706 configured to attach to the anterior surface of the patient's tibia 10 and a lower portion 708 configured to attach to the anterior surface of the patient's talus 20. The posterior bone-contacting surfaces of the upper portion 706 and lower portion 708 may be keyed to the geometry of the patient's tibia 10 and talus 20, respectively, so that tibia guide 700 may fit onto the patient's tibia 10 and talus 20 in only a single position and orientation.

Two pin holes 710 and 712 extend through both the anterior surface 702 and the posterior surfaces of the upper portion 706 of the first talus guide 700 and are sized and shaped to receive fixation pins, or other suitable fixation means, therethrough to fix the upper portion 706 of the talus guide 700 to the patient's tibia 10. Preferably, pin holes 710 and 712 and positioned to correspond with pin holes of a corresponding tibia guide so that pins previously used to couple a tibia guide to tibia 10 can be used without removal to couple the first talus guide 700 to the tibia 10. In the illustrated example, pin holes 710 and 712 are positioned superior to a transverse cutting guide slot 720 of the first talus guide 700. Pin hole 710 and may be positioned on a lateral side of the first talus guide 700 and pin hole 712 may be positioned on a medial side of the first talus guide 700, with pin holes 710 and 712 being positioned substantially the same height from transverse slot 720.

The transverse slot 720 may be defined by a guide portion generally consisting of two parallel walls defining the transverse slot 720 therebetween. Transverse slot 720 may be configured to assist the surgeon in creating a flat transverse cut in the patient's proximal talus 20. The transverse slot 720 may be fully enclosed to facilitate a saw blade or other resection tool being directed in a limited intended manner. The parallel walls defining the transverse slot 720 may also define a first pin hole 721 on a lateral side of the first talus guide 700 and a second pin hole 722 on a medial side of the first talus guide 700. The pin holes 721 and 722 may be configured to receive pins, similar to as described above in connection with pin holes 710 and 712. Pins extending through pin holes 721 and 722 and into the patient's talus 20 may help guide the saw blade, or other cutting tool, as it is inserted through the transverse cutting slot 720 and into the patient's talus 20. In addition, the pins extending through pin holes 721 and 722 may help protect soft tissue, hard tissue, and portions of the cutting guide from being unintentionally cut or otherwise damaged.

Similar to other talus guides described herein, first talus guide 700 may include a protrusion in the form of a tongue or paddle 725 extending posteriorly from an area of the first talus guide 700 between the upper portion 706 and lower portion 708 and superior to the transverse slot 720 (best shown in FIG. 9D). The paddle 725 may be configured for insertion between the resected surface of the distal tibia 10 and the unresected proximal surface of the talus 20. Paddle 725 is preferably sized and shaped to provide additional surface area contact between first talus guide 700 and the tibia 10 and talus 20, which may better support the foot after the tibia 20 has been cut.

Prior to resecting the talus 20, the patient's foot may be rotated so that the talus 20 is in proper contact with the lower portion 708 of first talus guide 700. Once the talus 20 is in the proper position, the surgeon may insert pins through pin holes 714 and 716 and into the properly positioned talus 20. Pin holes 714 and 716 are positioned inferiorly of the transverse cutting slot 720. The transverse cut in the talus 20 may then be made with the guidance of transverse cutting slot 720.

Figure 9E:
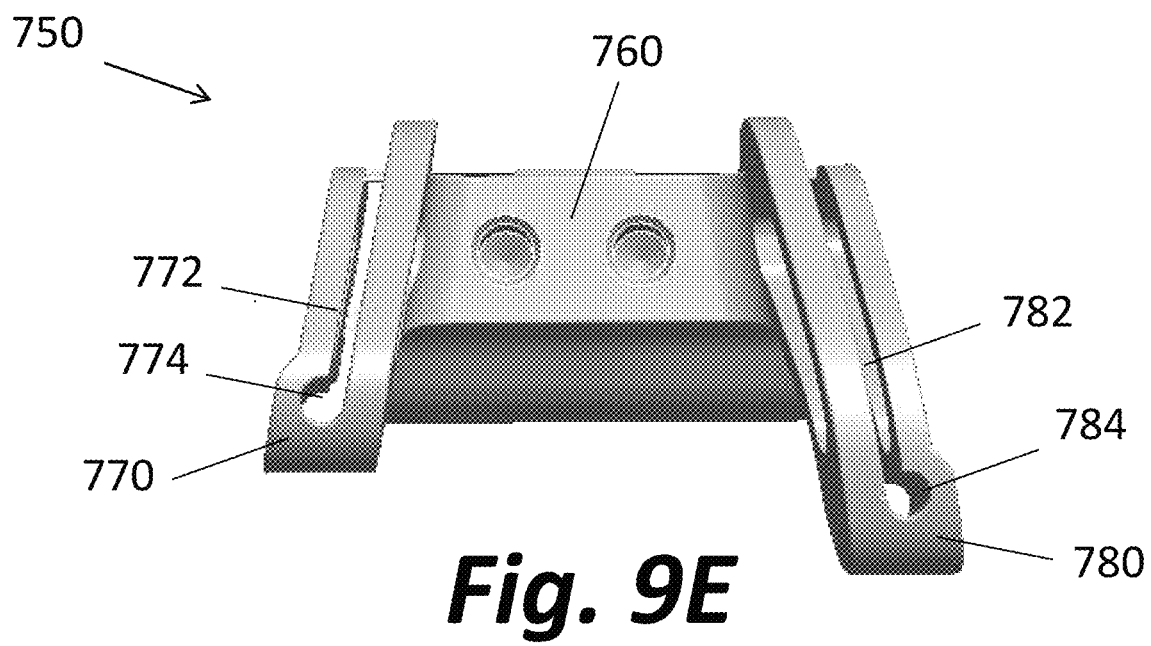
FIG. 9E is a front view of a second talus guide of a two-stage talus guide system.
Figure 9F:
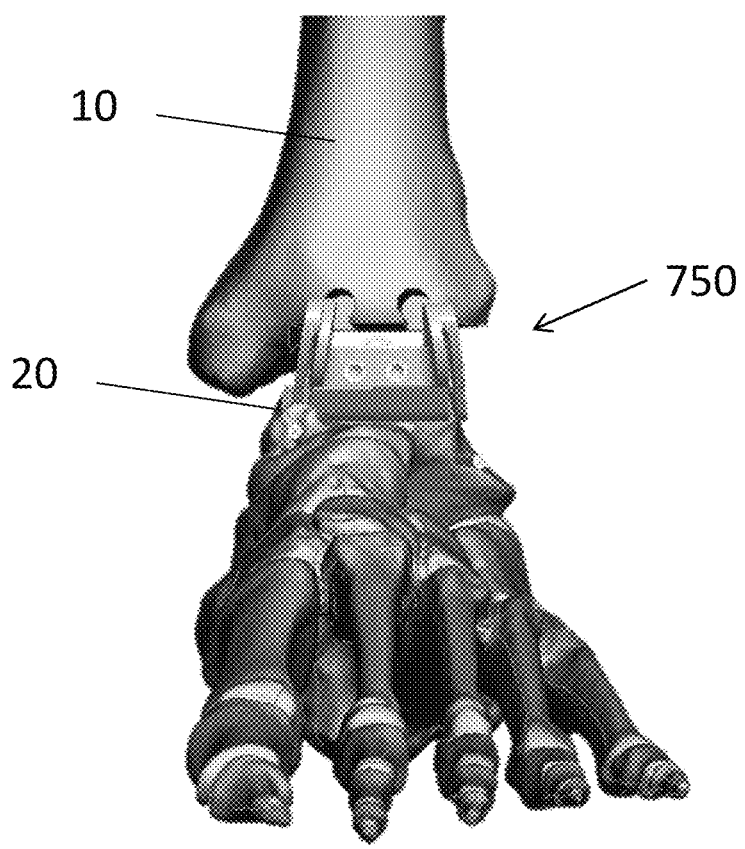
FIGS. 9F-H are various views of the second talus guide of FIG. 9E coupled to an ankle joint prior to medial and lateral talus cuts being made.
Figure 9G:
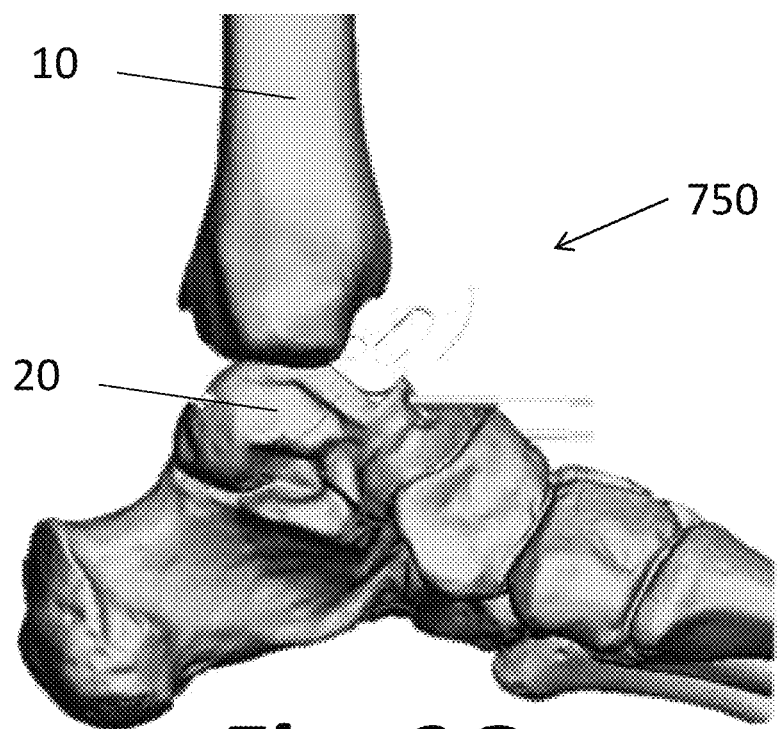
Figure 9H:
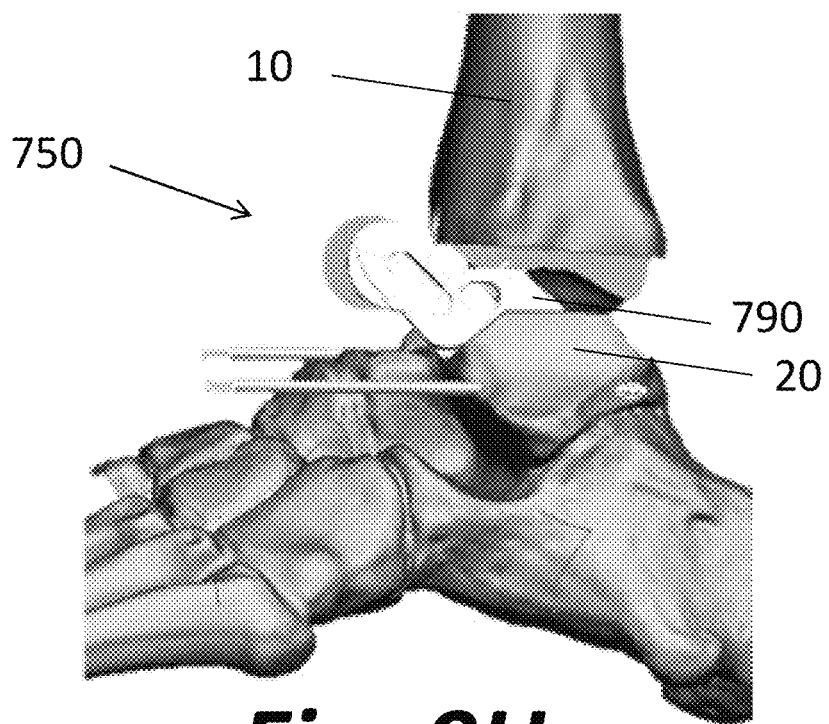
Figure 9I:
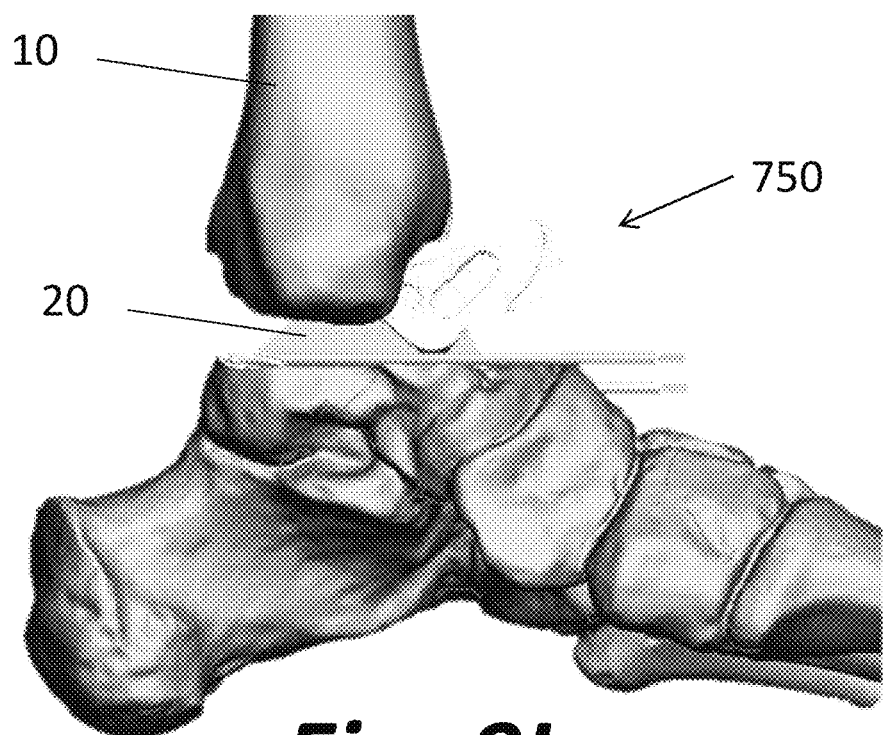
FIGS. 9I-J are various views of the second talus guide of FIG. 9E coupled to an ankle joint after medial and lateral talus cuts are made.
Figure 9J:
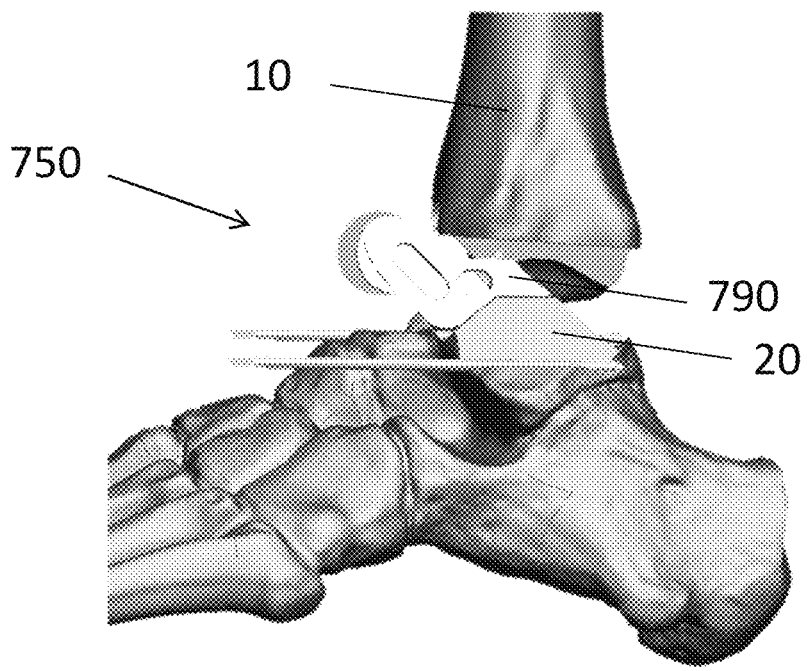

After the first talus guide 700 is used to create the transverse cut in the talus 20, the first talus guide 700 may be removed. Pins in the bone may also be removed, with the exception of pins previously passing through pin holes 714 and 716, which may be left in place. FIG. 9E illustrates a second talus guide 750 for use in creating medial and lateral cuts in the talus 20 after the transverse cut is made using the first talus guide 700. FIGS. 9F-H illustrate the second talus guide 750 coupled to the tibia 10 and talus 20 of the patient after the tibial cuts and the transverse talus cut have been made, but prior to the medial and lateral talus cuts being made. FIGS. 9I-J illustrate the second talus guide 750 coupled to the tibia 10 and/or talus 20 of the patient after the medial and lateral talus cuts have been made. It should be understood that talus guide 750 (as well as other talus guides described herein) may be coupled only to the talus 20, or may be coupled to both the tibia 10 and the talus 20.

Second talus guide 750 may include a central body portion 760, a lateral body portion 770, and a medial body portion 780. The lateral body portion 770 may include a lateral cutting slot 772 extending at a slight angle to the mechanical axis of the tibia. The lateral cutting slot 772 may be defined by two substantially parallel walls and form a pin hole 774 at an inferior end of the lateral cutting slot 772. Similarly, the medial body portion 780 may include a medial cutting slot 782 extending at a slight angle to the mechanical axis of the tibia. The medial cutting slot 782 may be defined by two substantially parallel walls and form a pin hole 784 at an inferior end of the medial cutting slot 782. Both the lateral cutting slot 772 and the medial cutting slot 782 may be bounded at a superior end by a portion of the corresponding lateral body portion 770 and medial body portion 780. These superior connections may provide additional stability as a blade or other cutting tool is moved through the lateral cutting slot 772 and media cutting slot 782.

Pin holes 774 and 784 may correspond in size and position to pin holes 714 and 716 of the first talus guide 700, so that second talus guide 750 may be slipped over the pins in the bone previously passing through pin holes 714 and 716. In addition, one or both walls of lateral body portion 770 and the medial body portion 780 may extend superiorly of the central body portion 760, with the superior extensions adapted to fit into the pin holes created in the bone previously from pins passing through pin holes 710. 712 of the first talus guide 700. As best seen in FIGS. 9H and 9J, second talus guide 750 may also include a protrusion 790 in the form of a tongue similar in form and purpose to protrusion 725. However, protrusion 790 may have flat superior and inferior surfaces, as second talus guide 750 is adapted for use after the distal tibia 10 has been resected and the proximal talus 20 has also been resected. With the protrusion 790 inserted between the resected surfaces of the distal tibia 10 and proximal talus 20, and with pin holes 774 and 784 inserted over the pins previously used for the first talus guide 700, a user may guide a cutting blade or other cutting tool through lateral cutting slot 772 and medial cutting slot 782 to create the medial and lateral cuts of the talus 20, as shown in FIGS. 9I-J. After the tibial cuts and talus cuts have been made, the ankle arthroplasty procedure may continue and the implant components fixed to the bones as desired.

Figure 10A:
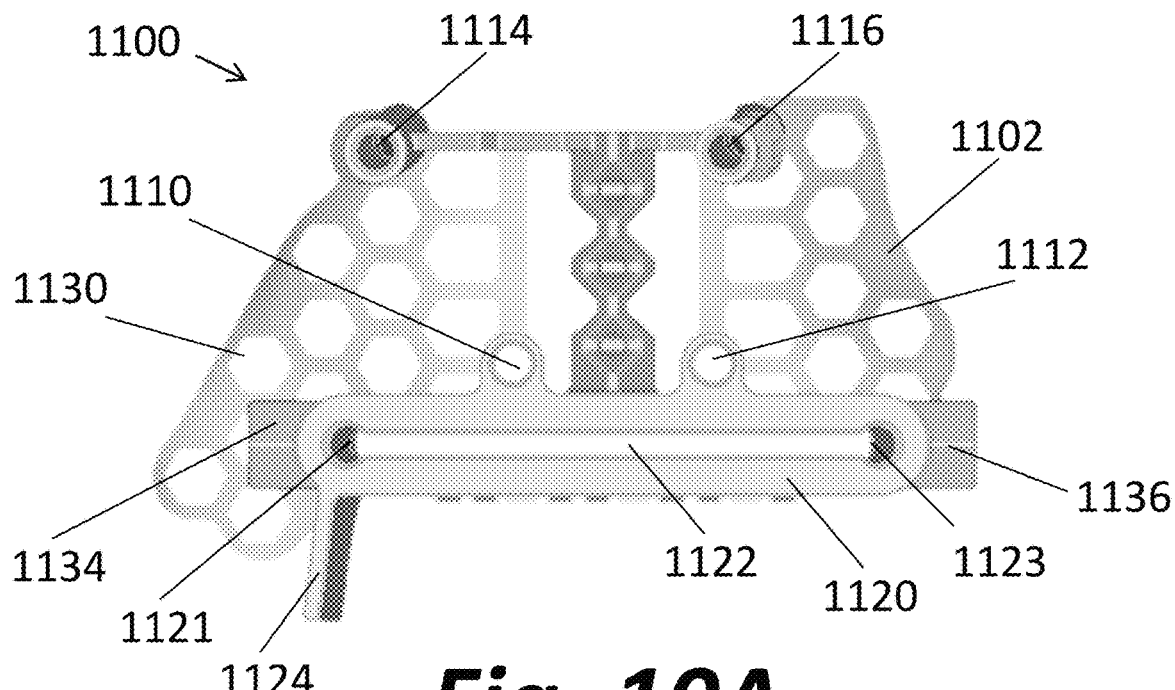
FIGS. 10A-D are various views of a tibia guide according to another aspect of the disclosure.
Figure 10B:
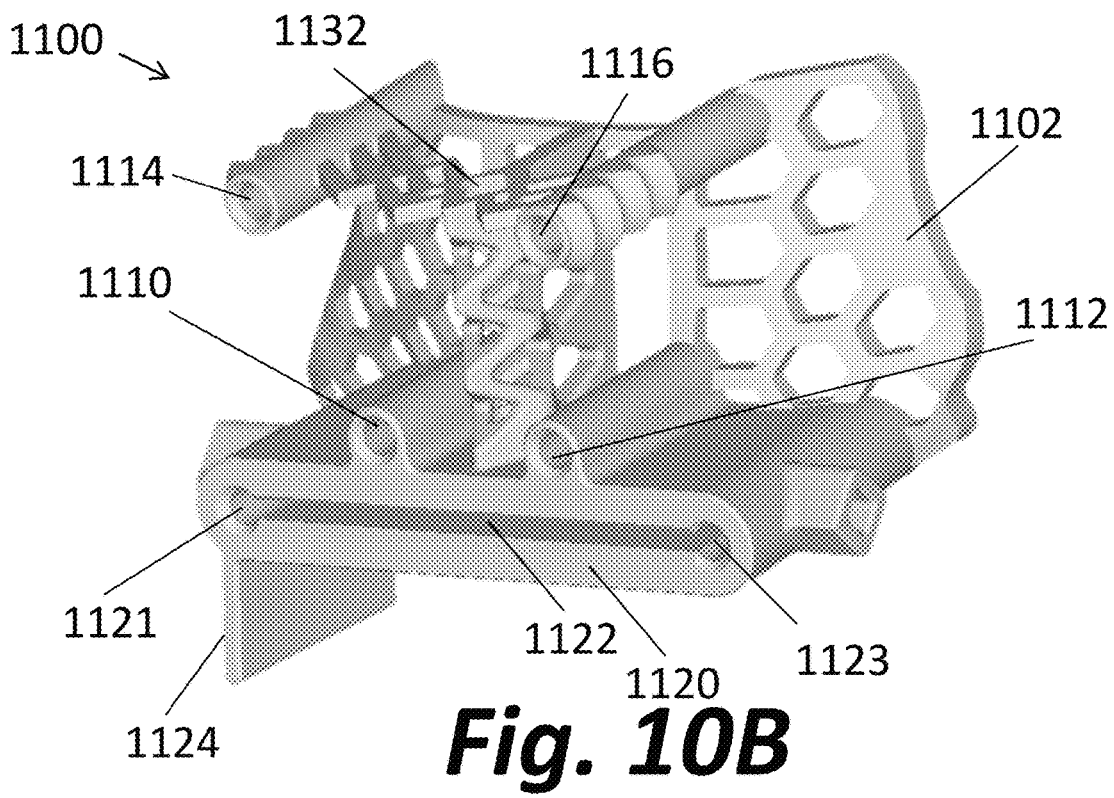
Figure 10C:
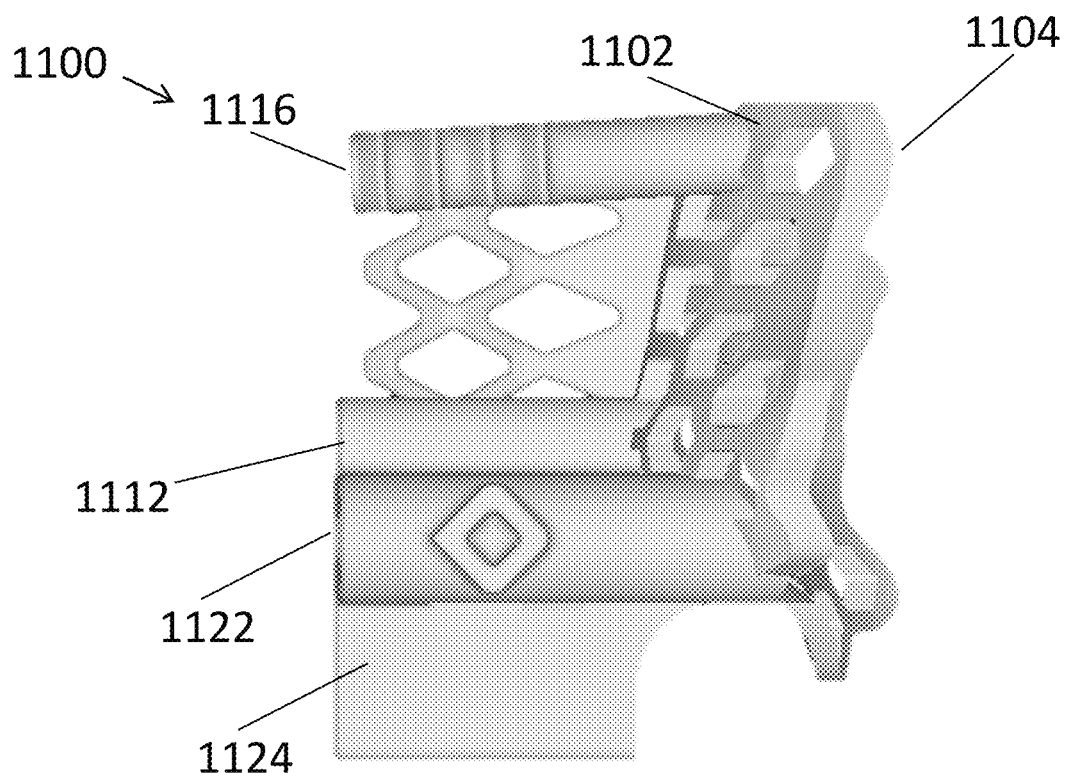
Figure 10D:
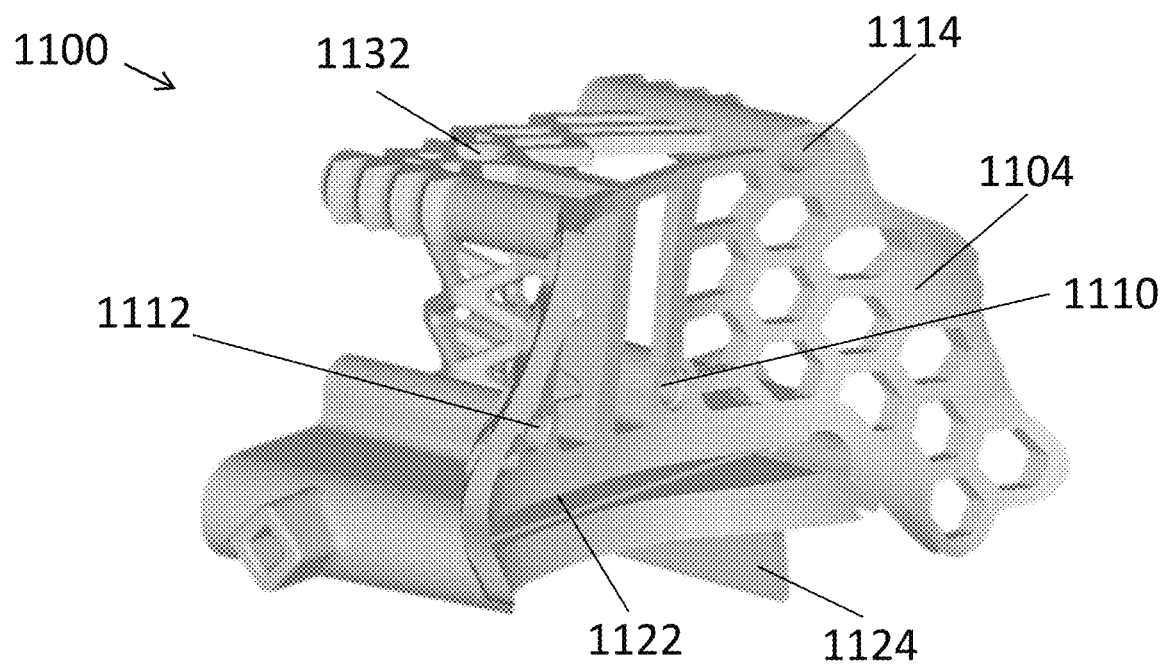
Figure 10E:
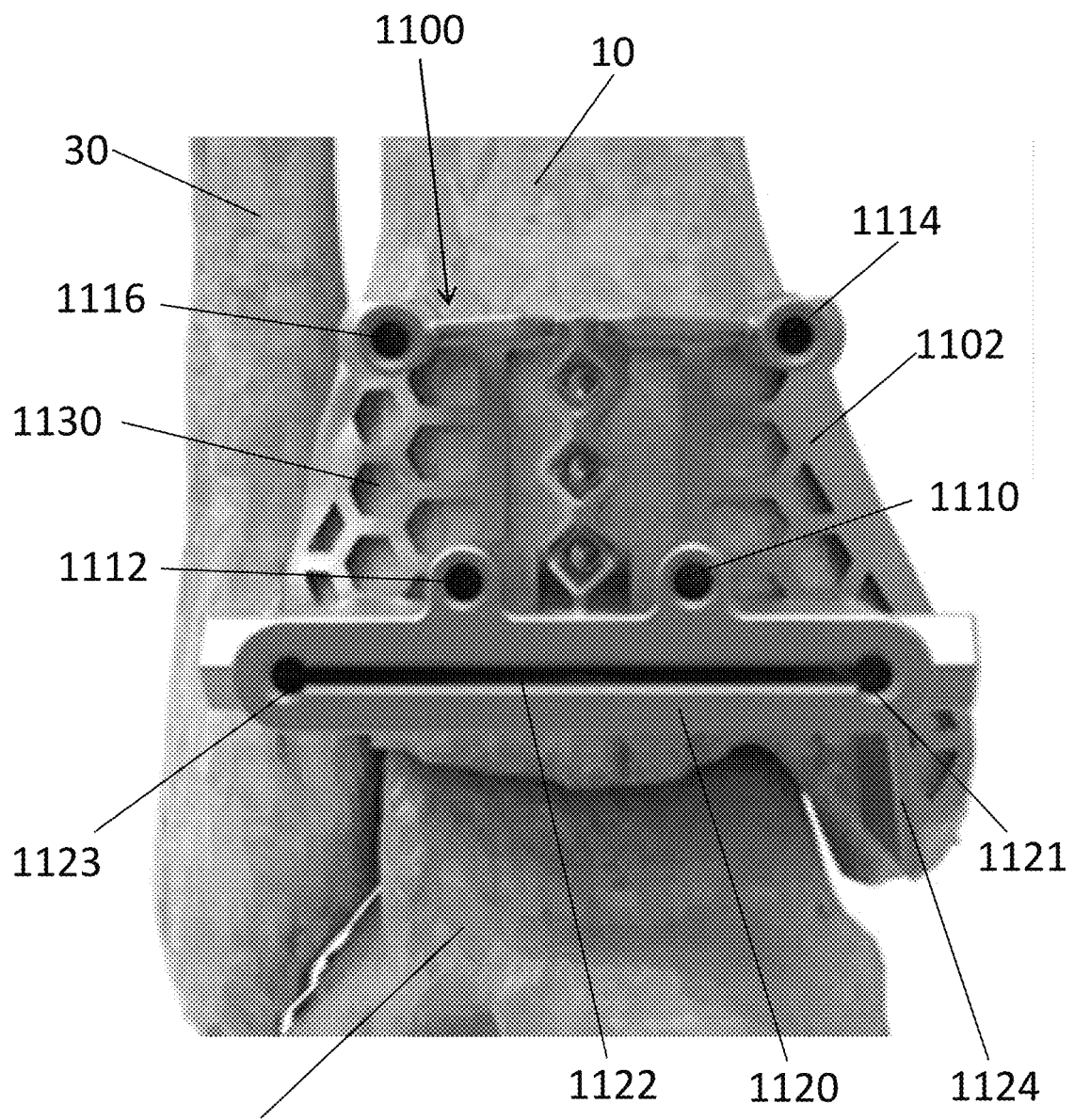
FIGS. 10E-G are various views of the tibia guide of FIGS. 10A-D coupled to the ankle of a patient.
Figure 10F:
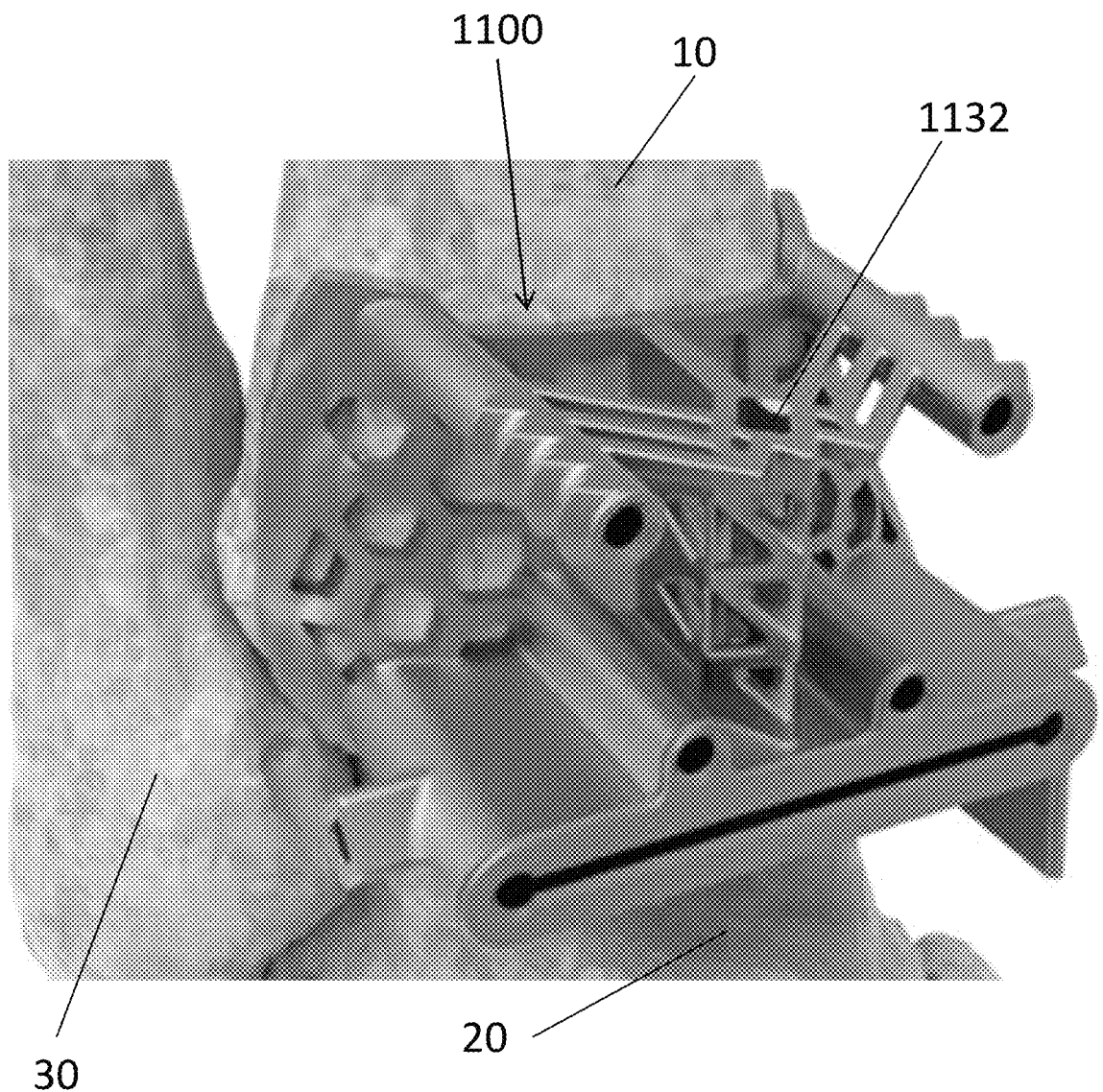
Figure 10G:
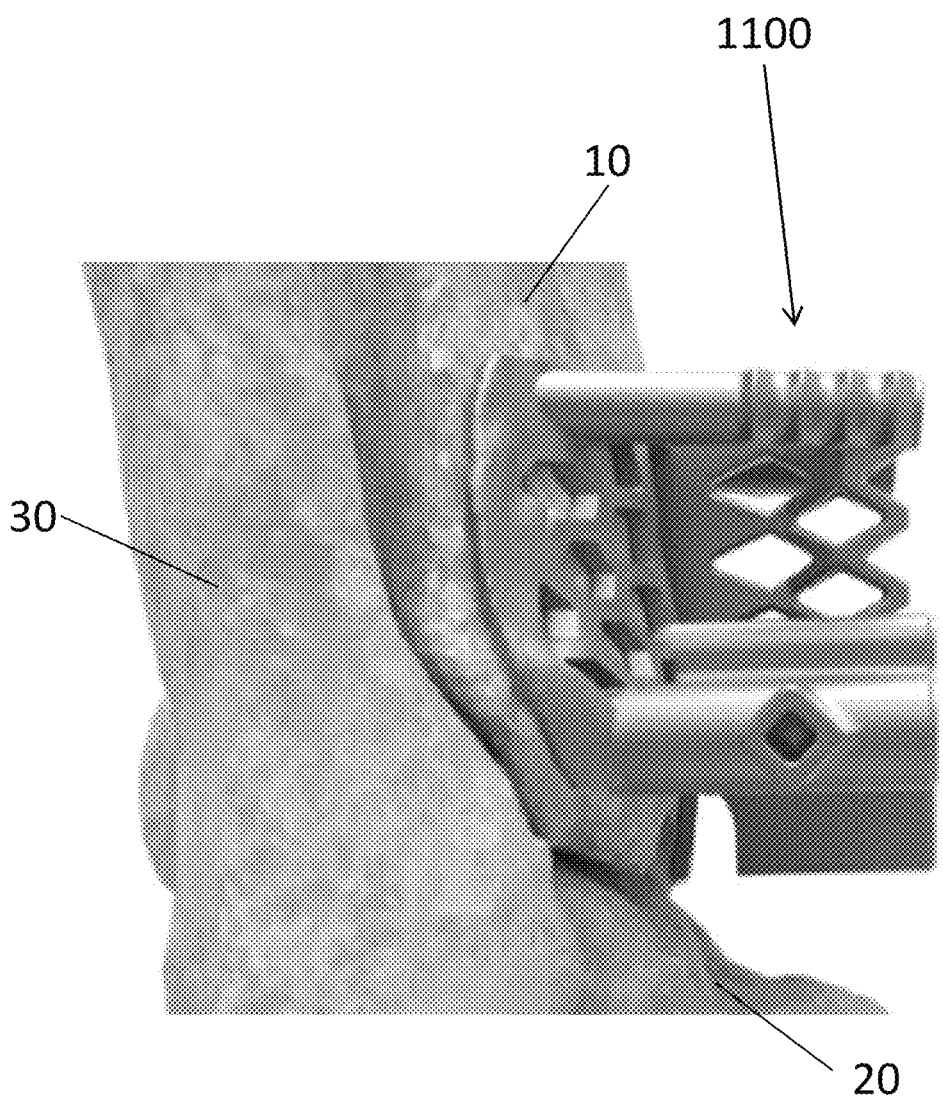

FIGS. 10A-D show various views of another example of a patient-specific tibia guide 1100, with FIGS. 10E-G showing the tibia guide coupled to the distal tibia of a patient. However, it should be understood that tibia guide 1100 shown in FIGS. 10A-D is for a left ankle, whereas the tibia guide of FIGS. 10E-G is for a right ankle, which may include identical but mirrored features. Tibia guide 1100 may have various features similar to other tibia guides described herein, including tibia guide 100. For example, tibia guide 1100 includes an anterior surface 1102 and a posterior bone-contacting surface 1104. Tibia guide 1100 is configured to attach to the anterior surface of the patient's tibia 10. The posterior bone-contacting surface 1104 may be keyed to the geometry of the patient's tibia 10 so that tibia guide 1100 may fit onto the patient's tibia 10 in only one (or substantially only one) position and orientation. In addition, the posterior bone-contacting surface 1104 may be curved posteriorly from the center toward the medial and lateral edges so that the tibia guide 1100 at least partially wraps around the tibia 10 to increase surface area contact between the tibia guide 1100 and the tibia 10 in the medial-to-lateral direction. Still further, the posterior bone-contacting surface 1104 may be curved posteriorly from the center toward the superior and inferior edges so that the tibia guide 1100 at least partially wraps around the tibia 10 to increase surface area contact between the tibia guide 1100 and the tibia 10 in the superior-to-inferior direction. As in other embodiments described herein, posterior bone-contacting surface 1104 may include a portion that extends medial of and inferior to the transverse cutting guide for placement on the patient's medial malleolus which may further help stabilize the guide.

Two pin holes 1110 and 1112 extend through both the anterior surface 1102 and posterior surface 1104 of the tibia guide 1100 and are sized and shaped to receive fixation pins, or other suitable fixation means, therethrough to fix the tibia guide 1100 to the patient's tibia 10. In the illustrated example, pin holes 1110 and 1112 are positioned superior to a transverse cutting guide slot 1122 of the tibia guide 1100. Pin hole 1110 may be positioned on a medial side of the tibia guide 1100 and pin hole 1112 may be positioned on a lateral side of the tibia guide 1100, with pin holes 1110 and 1112 being positioned substantially the same height from cutting guide slot 1122. In the illustrated embodiment, pin holes 1110 and 1112 are positioned just superior of cutting guide slot 1122. Pin holes 1110 and 1112 may be formed in portions of tibia guide 1100 that extend farther anteriorly than other portions of the anterior surface 1102 of tibia guide 1100, for example in cylindrical or other shaped projections, in order to provide greater surface area for contact between pins inserted through pin holes 1110 and 1112 and tibia guide 1100. Pin holes 1110 and 1112 may have positions and orientations that correspond to pin hole positions and orientations of a talus guide 1150 so that the talus guide 1150 may be slid over the same pins used to hold the tibia guide 1100 to the patient's tibia 10. Further, pin holes 1110 and 1112 may have positions and orientations that correspond to holes in the tibia implant so that, when the holes are drilled out of the tibia 10 for implantation of the tibia implant, no holes remain in the bone from use of the tibia guide 1100 or the talus guide 1150.

Tibia guide 1100 may include two additional pin holes 1114 and 1116. Pin hole 1114 may be positioned on a medial side of the guide and pin hole 1116 may be positioned on a lateral side of the guide, with both pin holes 1114 and 1116 being positioned near a superior or top end of the guide. Pin holes 1114 and 1116 may be defined within cylindrical projections generally similar to pin holes 1110 and 1112. However, pin holes 1114 and 1116 may have trajectories that are slightly different from the trajectories of pin holes 1110 and 1112. For example, the trajectories of the pin holes 1114 and 1116 may be about five degrees off the trajectories of the pin holes 1110 and 1112. Pin holes 1114 and 1116 may be referred to as contingency or "bailout" holes with pin holes 1114 and 1116 only intended for use with a universal cutting guide instead of the patient-specific tibia guide 1100 and talus guide 1150. In other words, if a surgeon decides that the tibia guide 1100 should not be used for any reason, pins may be passed through pin holes 1114 and 1116 into the tibia 10, the tibia guide 1100 may be removed by sliding the guide off the pins, and a traditional universal (i.e. non-patient specific) guide with holes corresponding to the position of pin holes 1114 and 1116 may be used to complete the procedure. It should be understood that, even if these "bailout" holes are used, talus guide 1150 (described in greater detail below) may still be used, or otherwise alternative non-patient specific instruments may be used for resecting the talus 20.

The tibia guide 1100 may also include one or more visualization windows 1130. Windows 1130 may facilitate the surgeon in better visualizing the patient's tibia 10 and checking proper fitting between the tibia guide 1100 and the patient's tibia 10. In the illustrated embodiment, windows 1130 may be in the form of a plurality of cut-outs or other apertures in the portion of tibia guide 1100 contoured to the patient's bone contours, and the cut-outs may extend from the anterior surface 1102 to the posterior surface 1104. In the illustrated embodiment, windows 1130 include a first group of windows on a lateral side of the tibia guide 1100 and a second group of windows on the medial side of the tibia guide. The windows 1130 may include a plurality of hexagonal shaped cut-outs, as well as other shaped cut-outs, such as substantially rectangular cut-outs extending from an area near cutting slot 1122 to the superior surface of the tibia guide, as well as a plurality of five-sided cut-outs positioned between the hexagonal and rectangular cut-outs. However, it should be understood that other shapes or other groups of shapes may be suitable. In particular, any shaped cut-outs that provide for good visibility while leaving enough structure to maintain structural integrity and rigidity of the tibia guide 1100 may be suitable in place of the specific embodiment shown.

A cutting guide 1120 may include a first guide portion 1122 and a second guide portion 1124, which may be substantially similar to the cutting guide slot 220 of FIG. 7A. The first guide portion 1122 may generally consist of two parallel transverse walls defining a first slot therebetween. This first guide portion 1122 and corresponding first slot are configured to assist the surgeon in creating a flat transverse cut in the patient's tibia 10. Preferably, the slot of the first guide portion 1122 is substantially planar and, when tibia guide 1100 is coupled to the tibia 10, the plane of the slot 1122 is substantially orthogonal to the mechanical axis of the tibia 10. The second guide portion 1124 may consist of a single wall extending at an oblique angle to the first slot 1122, which may in particular be an obtuse angle. However, in some circumstances it may be suitable for the second guide portion 1124 to extend perpendicularly relative to the first slot. The second guide portion 1124 may define a second slot, although in this instance the second slot is generally open because it is bounded on only one side. This second slot may be configured to assist the surgeon in releasing the resected bone from the medial malleolus and/or from the medial side of the tibia, superior to the medial malleolus. The configuration of the first slot being defined by a fully (or nearly fully) enclosed first guide portion 1122 may facilitate a saw blade or other resection tool being directed in a limited intended manner. The configuration of the second slot being open and bounded only by the second guide portion 1124 may provide additional freedom of movement that may be necessary for the surgeon to make the cut. Although the first cutting guide portion 1122 is shown as a slot that is substantially closed, the cutting guide portion may take other forms described above in connection with other embodiments of tibia guides.

In addition to defining the first slot, the first guide portion 1122 may define a first pin hole 1121 at a first end of the first slot relatively near the second guide portion 1124. The first guide portion 1122 may define a second pin hole 1123 on the opposite side of the first slot from the first pin hole 1121. The pin holes 1121 and 1123 may be configured to receive pins, similar to as described above in connection with pin holes 1110 and 1112. Pins extending through pin holes 1121 and 1123 into the patient's tibia 10 may help guide the saw blade, or other cutting tool, as it is inserted through the first and/or second slots and into the patient's tibia 10. In addition, the pins extending through pin holes 1121 and 1123 may help protect soft tissue, hard tissue, and portions of the cutting guides from being unintentionally cut or otherwise damaged. Further, it should be noted that pin holes 1121 and 1123, and/or pins extending through these pin holes, may be calibrated with the tibia guide 1100, based on information from the prior imaging (e.g. CT scan) so that the pins cannot be over inserted.

Figure 10H:
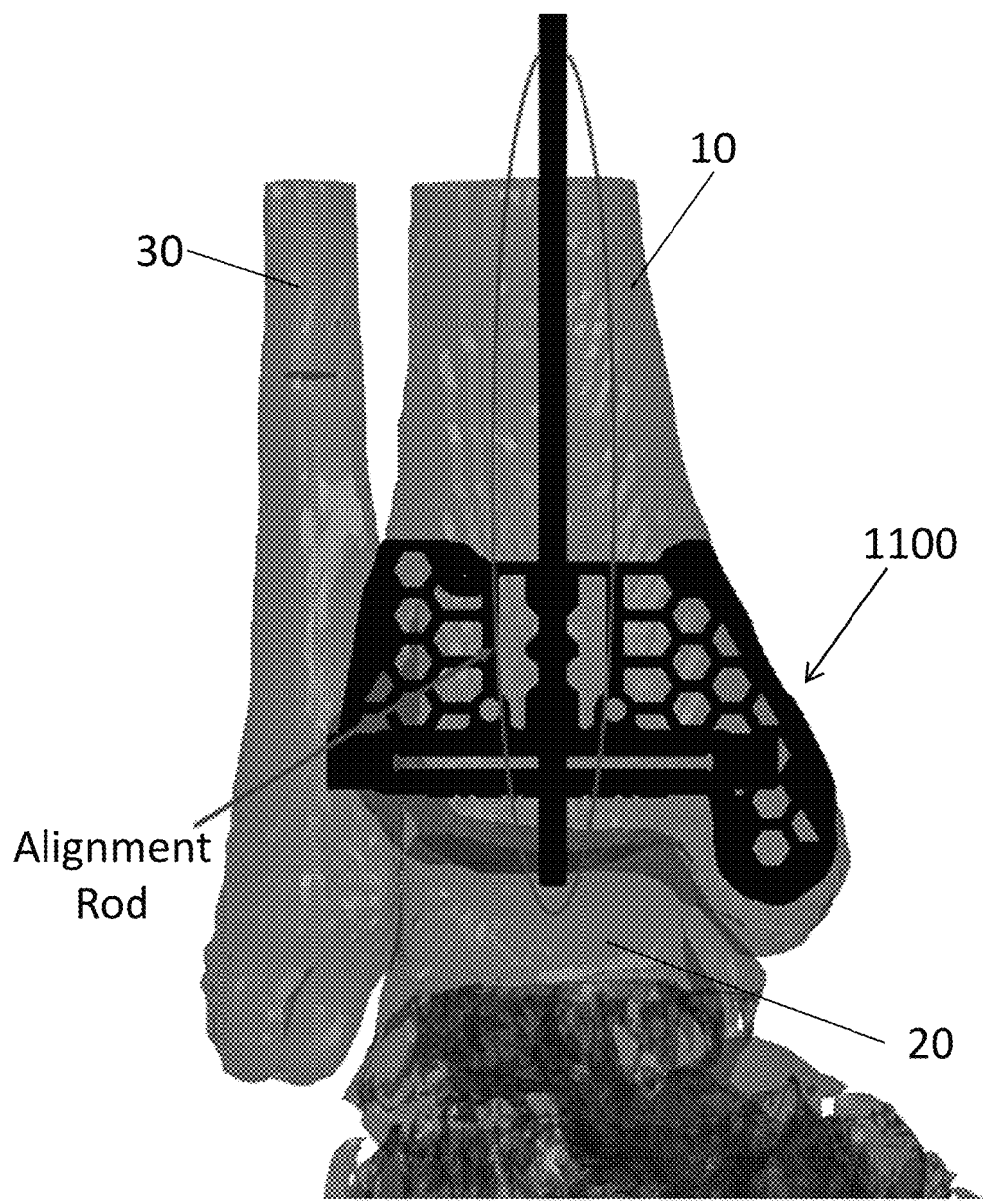
FIG. 10H is a front view of the tibia guide of FIGS. 10A-D coupled to an alignment rod and positioned on a patient's tibia.

Tibia guide 1100 may include an alignment hole 1132 adapted to receive an alignment rod therethrough. Alignment hole 1132 is best shown in FIGS. 10B, 10D, and 10F. Alignment hole 1132 may extend from the superior end of tibia guide 1100 and to or through first guide portion 1122, and is preferably orthogonal to the transverse cutting slot defined by the first guide portion 1122. With this configuration, an alignment rod may be passed through alignment hole 1132 to check for desired alignment of the tibia guide 1100 to the tibia 10, as shown in FIG. 10H. Tibia guide 1100 may also include one or more fixation blocks, 1134, 1136, which may be assist in fixation of the tibia guide 1100 during manufacturing operations.

Figure 11A:
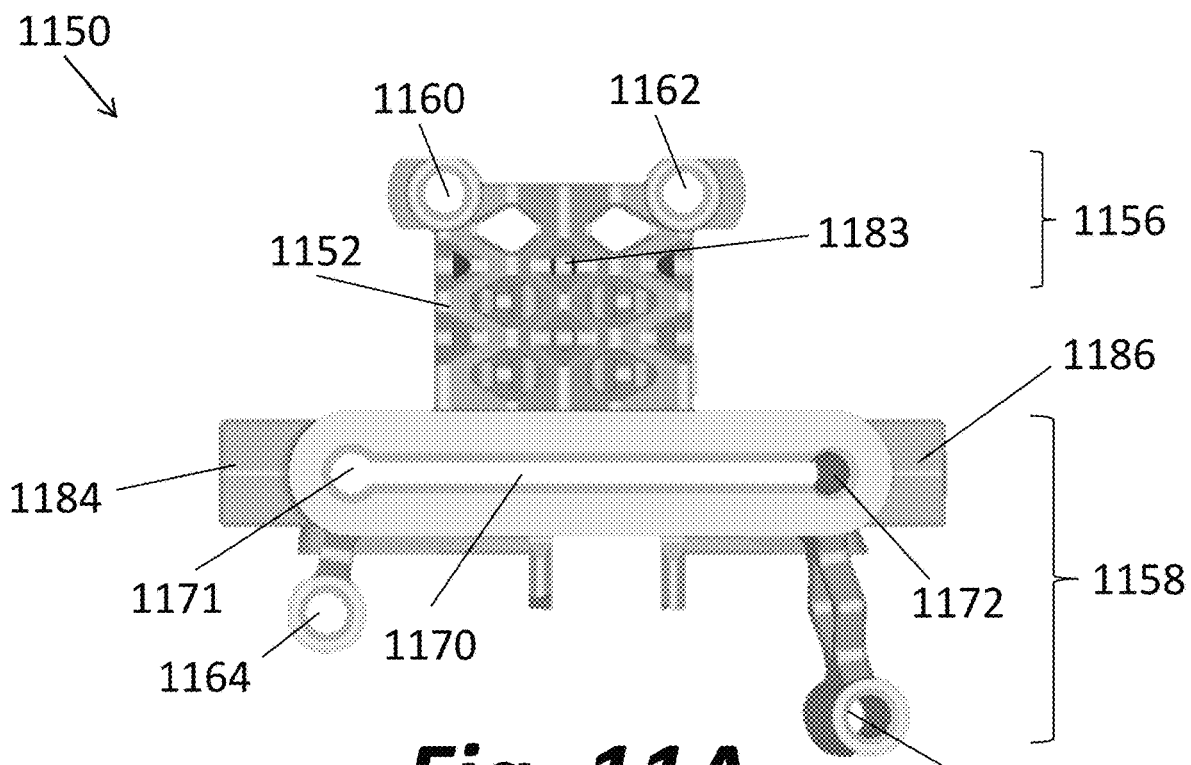
FIGS. 11A-E are various views of a talus guide according to another aspect of the disclosure.
Figure 11B:
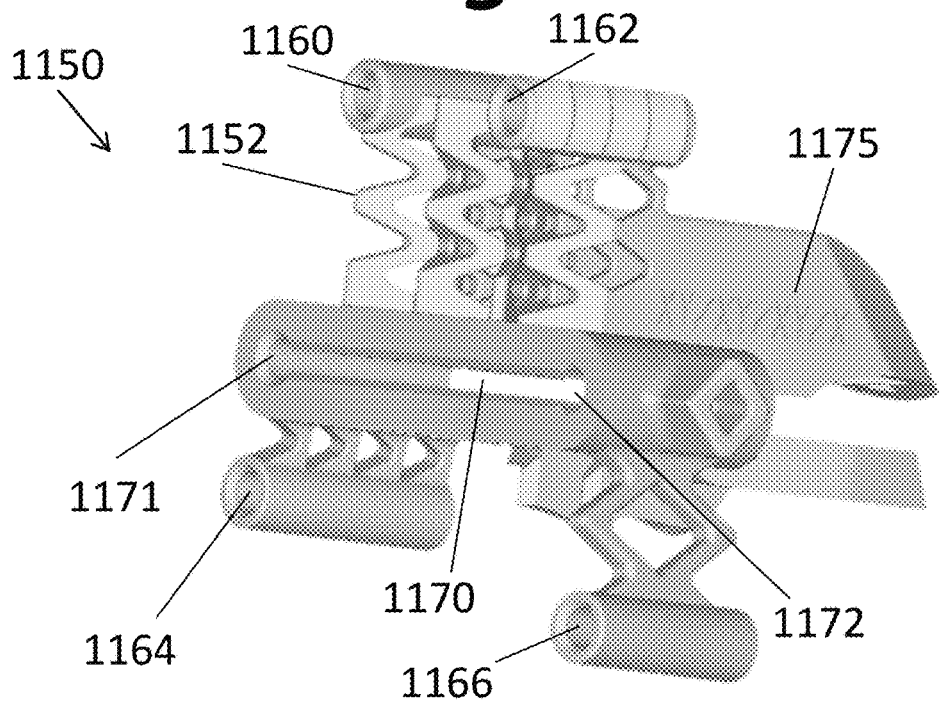
Figure 11C:
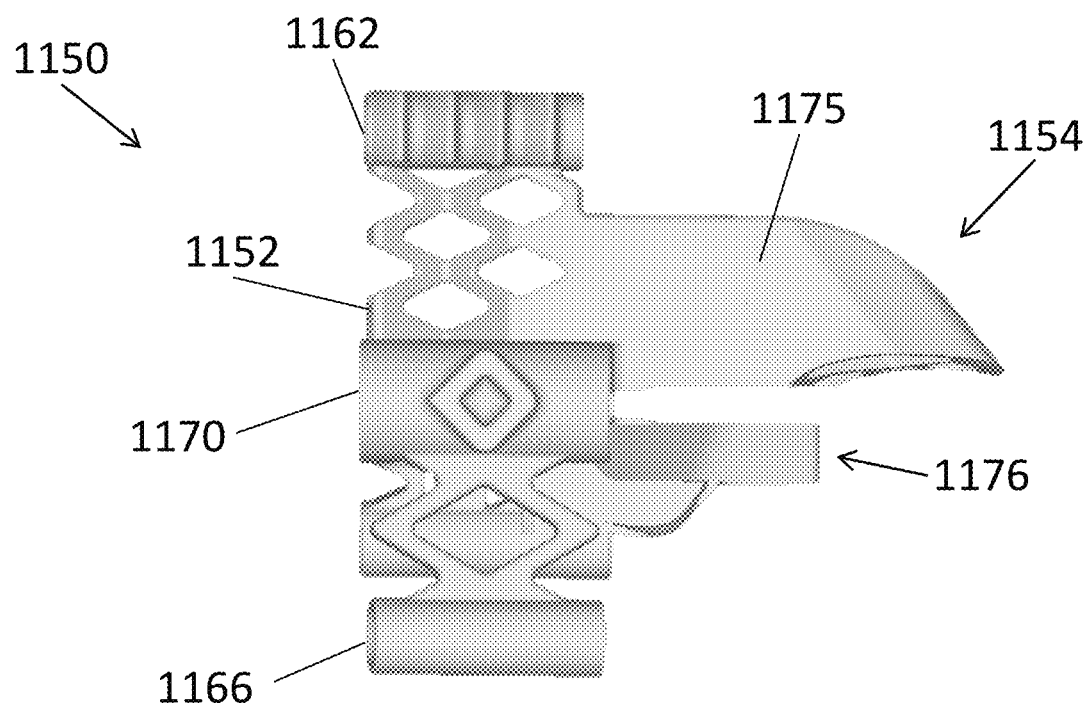
Figure 11D:
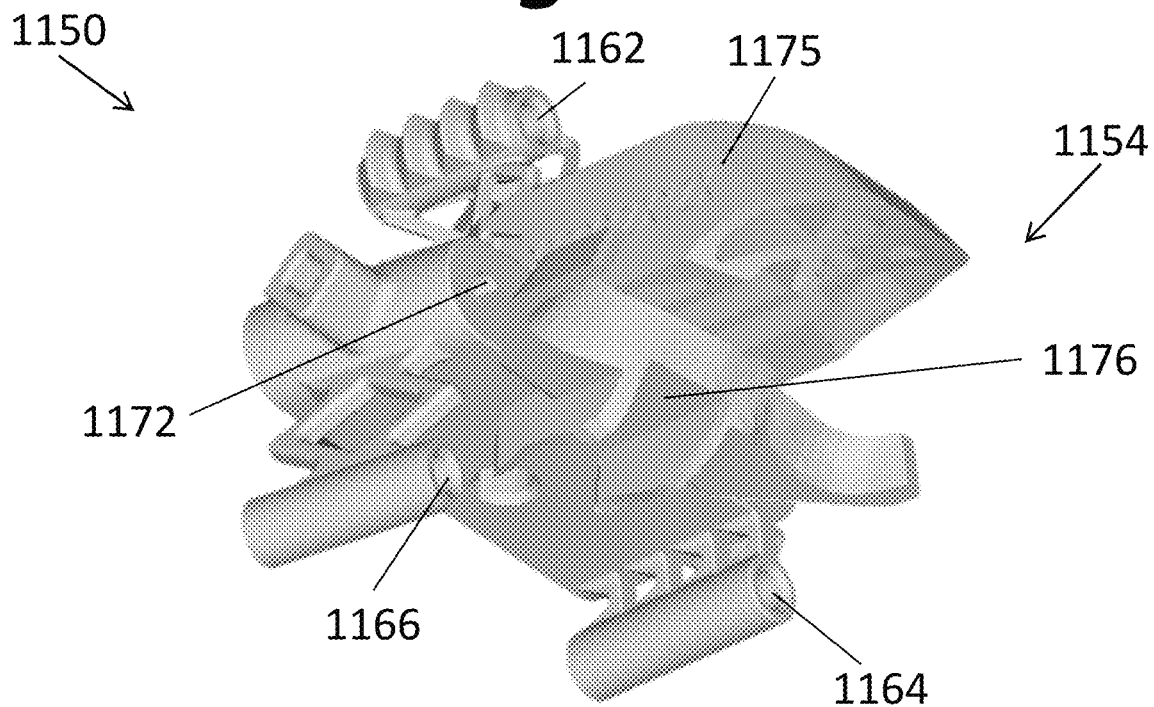
Figure 11E:
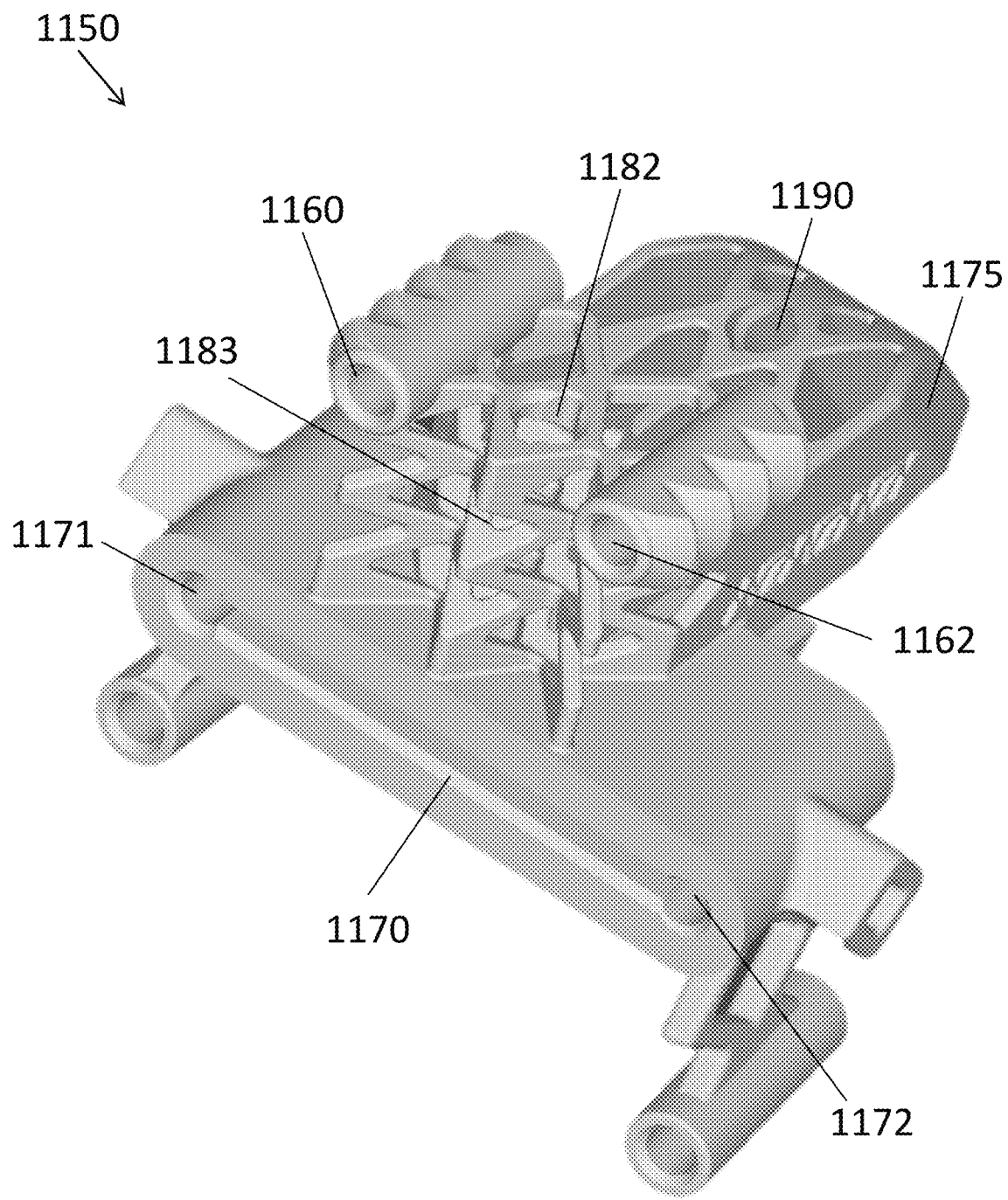
Figure 11F:
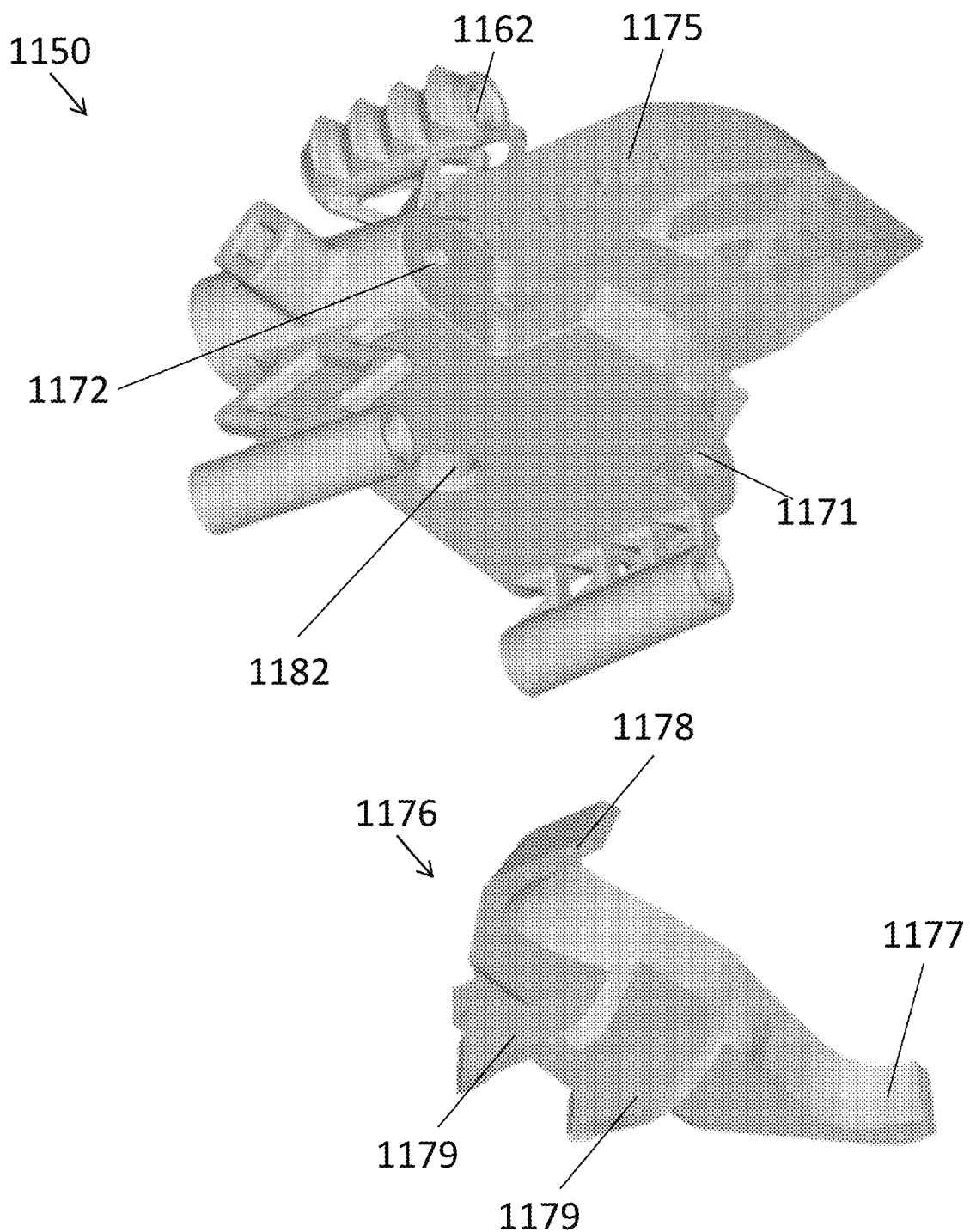
FIG. 11F is an exploded view of the talus guide of FIGS. 11A-D.
Figure 11G:
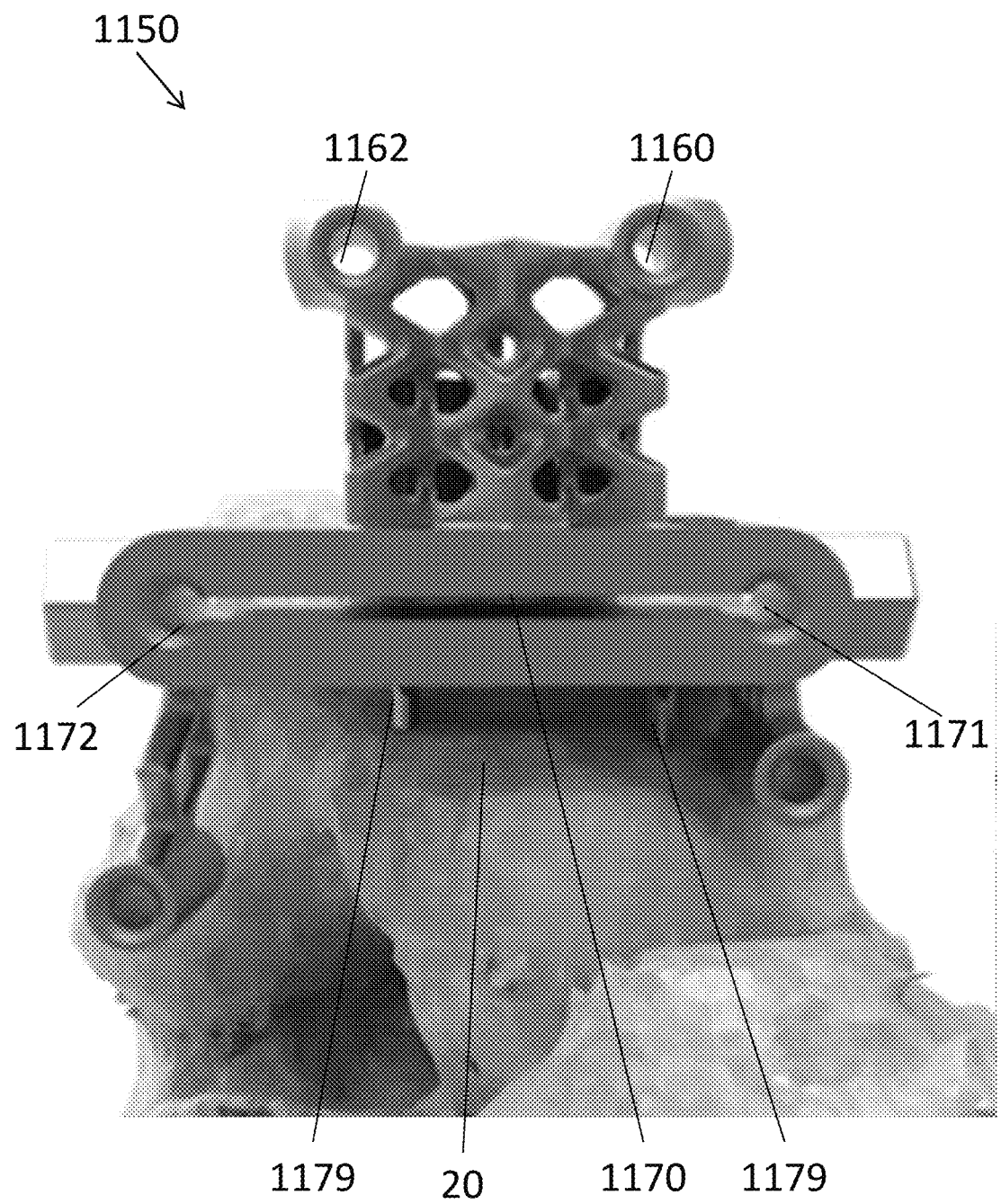
FIGS. 11G-I are various views of the talus guide of FIGS. 10A-D coupled to the ankle of a patient.
Figure 11H:
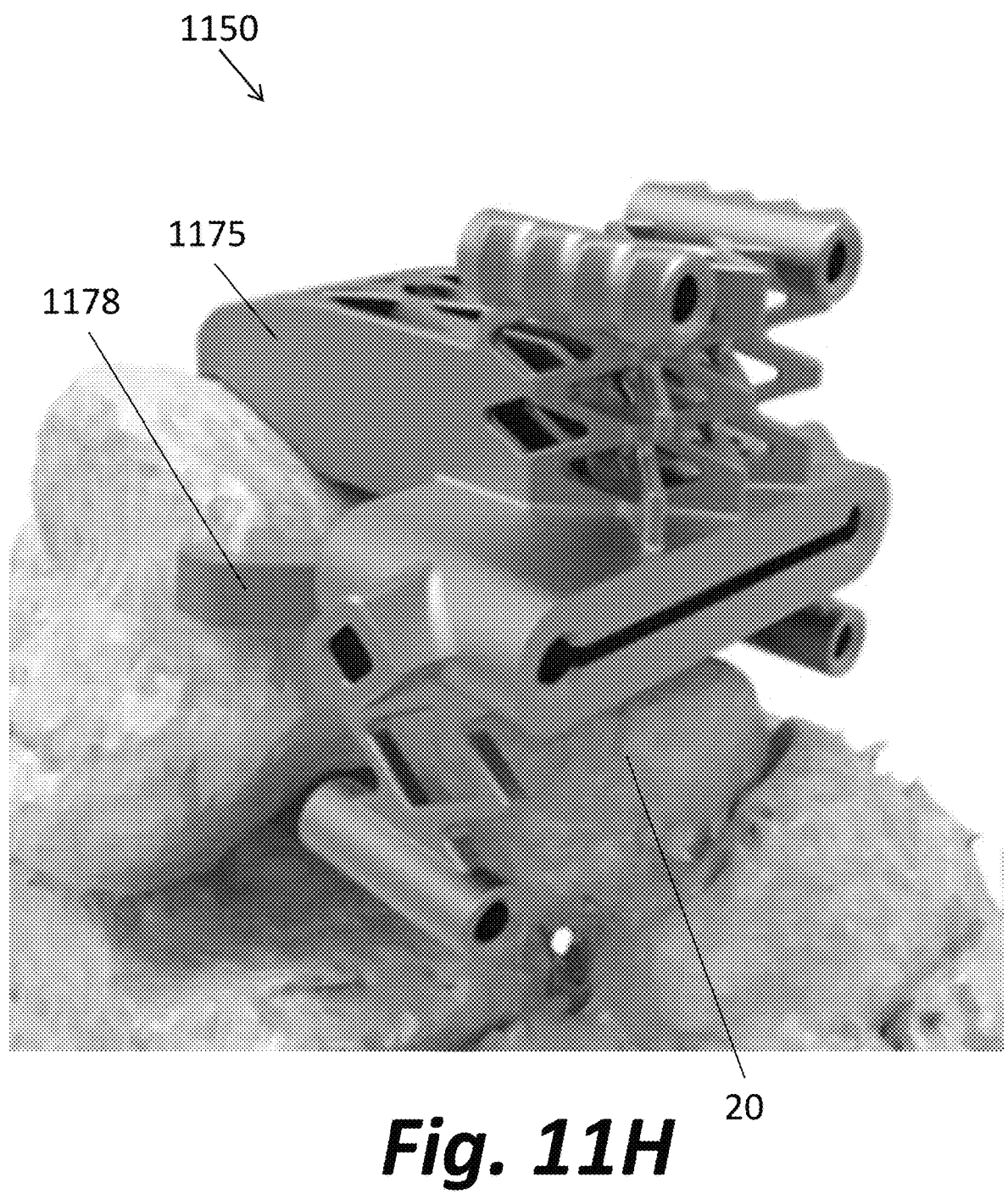
Figure 11I:
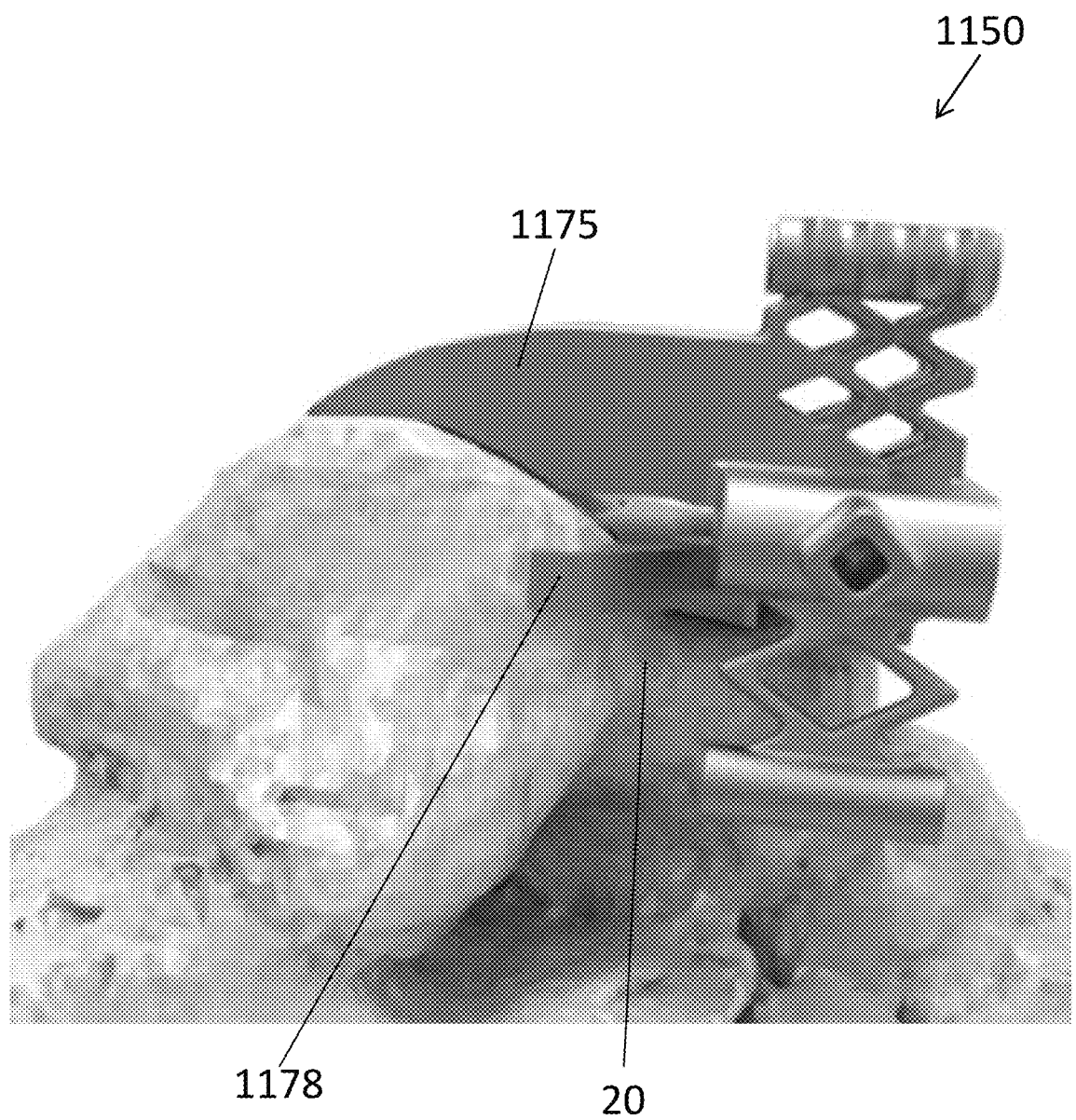

FIGS. 11A-F show various views of another example of a patient-specific talus guide 1150, with FIGS. 11G-I showing the talus guide coupled to the talus 20 of a patient. However, it should be understood that talus guide 1150 shown in FIGS. 11A-F is for a left ankle, whereas the talus guide of FIGS. 11G-I is for a right ankle, which may include identical but mirrored features. Talus guide 1150 may have various features similar to other talus guides described herein, including talus guide 150 and 750. For example, talus guide 1150 may include an anterior surface 1152 and one or more posterior bone-contacting surfaces 1154 described in greater detail below. Talus guide 1150 may include an upper portion 1156 configured to attach to the anterior surface of the patient's tibia 10 and a lower portion 1158 configured to attach to the anterior surface of the patient's talus 20. The posterior bone-contacting surfaces 1154 of the upper portion 1156 and lower portion 1158 may be keyed to the geometry of the patient's tibia 10 and talus 20, respectively, so that talus guide 1150 may fit onto the patient's tibia 10 and talus 20 in only (or substantially only) a single position and orientation, as described in greater detail below. As with other talus guides described herein, talus guide 1150 may be coupled to the talus 20 only, or to both the tibia 10 and the talus 20, with any of the contact areas optionally being patient-specific and configured to fit in only one or substantially only one orientation.

Two pin holes 1160 and 1162 may extend through both the anterior surface 1152 and a posterior surface 1154 of the upper portion 1156 of the talus guide 1150 and are sized and shaped to receive fixation pins, or other suitable fixation means, therethrough to fix the upper portion 1156 of the talus guide 1150 to the patient's tibia 10. In the illustrated example, pin holes 1160 and 1162 are positioned superior to a transverse cutting guide slot 1170 of the talus guide 1150. Pin hole 1160 and may be positioned on a medial side of the talus guide 1150 and pin hole 1162 may be positioned on a lateral side of the talus guide 1150, with pin holes 1160 and 1162 being positioned substantially the same height from transverse slot 1170. As best seen in FIG. 11C, pin holes 1160 and 1162 may be defined by cylindrical or other shaped projections, in order to provide greater surface area for contact between a pin inserted through pin holes 1160 and 1162 and talus guide 1150. Pin holes 1160 and 1162 may have the same size, position, and orientation with respect to one another as pin holes 1110 and 1112 of tibia guide 1100 so that, after use and removal of the tibia guide 1100, the pin holes 1160 and 1162 of the talus guide 1150 may be slipped over the pins that were previously used with pin holes 1110 and 1112 of the tibia guide 1100.

The transverse slot 1170 may be defined by a guide portion generally consisting of two parallel walls defining the transverse slot 1170 therebetween. Transverse slot 1170 may be configured to assist the surgeon in creating a flat transverse cut in the patient's talus 20. The transverse slot 1170 may be fully enclosed to facilitate a saw blade or other resection tool being directed in a limited intended manner. The parallel walls defining the transverse slot 1170 may also define a first pin hole 1171 on a medial side of the talus guide 1150 and a second pin hole 1172 on a lateral side of the talus guide 1150. The pin holes 1171 and 1172 may be configured to receive pins, similar to as described above in connection with pin holes 1160 and 1162. Pins extending through pin holes 1171 and 1172 and into the patient's talus 20 may help guide the saw blade, or other cutting tool, as it is inserted through the transverse cutting slot 1170 and into the patient's talus 20. In addition, the pins extending through pin holes 1171 and 1172 may help protect soft tissue, hard tissue, and portions of the cutting guide from being unintentionally cut or otherwise damaged.

The talus guide 1150 may include a protrusion in the form of a tongue or paddle 1175 extending posteriorly from an area of the talus guide 1150 between the upper portion 1156 and lower portion 1158 and superior to the transverse slot 1170. The paddle 1175 may be configured for insertion between the resected surface of the distal tibia 10 and the unresected proximal surface of the talus 20. Paddle 1175 is preferably sized and shaped to provide additional surface area contact between talus guide 1150 and the tibia 10 and talus 20, which may better support the foot after the tibia 20 has been cut. This support may be particularly useful during the step of resecting the talus 20 with a blade or other cutting tool through transverse slot 1170. All or some parts of paddle 1175 may be patient specific in order to match corresponding surfaces of the bone, although in some embodiments the paddle 1175 need not have any patient specific features. For example, a posterior portion of the inferior side of paddle 1175 may have a surface contour that matches the contours of the anterior/superior surfaces of the talus dome, which may be best seen in FIG. 11H. In addition, paddle 1175 may include an angled pin hole 1190 (best shown in FIG. 11E) to guide the datum pin into place so the surgeon can attach the existing datum pin cutting guides. Paddle 1175 may also help serve as a joint space evaluator to help ensure enough bone was removed from the patient so that the implants will fit on the prepared bone surface, with the height of the paddle 1175 being based on the patient's anatomy and the amount of bone to be resected. It should be understood that, in some embodiments, the paddle 1175 may be configured to provide relatively little contact with the bone, and an additional stabilizer (such as stabilizer 1176 described in greater detail below) may provide most of the desired or necessary contact area (which contact may be patient specific) between the talus guide 1150 and the patient's bone.

Talus guide 1150 may include an additional stabilizer 1176, which is best shown in the view of FIG. 11F, which illustrates stabilizer 1176 as a separate component. It should be understood that talus guide 1150 is preferably a single unitary piece, and is shown as separate pieces in FIG. 11F purely for better illustrating certain features of the components, although the stabilizer 1176 may optionally be fabricated separately from the rest of the talus guide 1150 and the components may then be coupled together. Stabilizer 1176 may include a medial wing 1177 and a lateral wing 1178 adapted to contact the medial and lateral aspects of the dome of the talus 20. Medial and lateral wings 1177, 1178 may each extend away from a center portion of stabilizer 1176 and curve posteriorly, with the surfaces preferably including contours that match the contours of the patient's talus 20 to help provide better stabilization of the talus guide 1150 on the talus, as best shown in FIGS. 11H-I. In addition to medial and lateral wings 1177, 1178, stabilizer 1176 may include two posterior rails 1179, as best shown in FIG. 11F. Posterior rails 1179 may both be relatively thin members protruding from an inferior surface of stabilizer 1176 and running in an anterior to posterior direction. Some portions of rails 1179, including the inferior surfaces, may be contoured to the patient's bone, and in particular to the corresponding contours of the superior aspect of the neck of the talus 20. The contact between rails 1179 and the superior aspect of the neck of the talus 20 may further help stabilize talus guide 1150 in place, as best shown in FIG. 11G. In all embodiments of talus guides described herein with a stabilizer 1176 or similar stabilizer structure, it should be understood that the paddle 1175 (or similar structure) may be omitted from the talus guide.

As noted above, pin holes 1160 and 1162 of talus guide 1150 may be slid over pins protruding from the tibia 10 that were previously engaged with the tibia guide 1100. Prior to resecting the talus 20, the patient's foot may be rotated so that the talus 20 is in proper contact with the paddle 1175 and stabilizer 1176 of talus guide 1150. Once the talus 20 is in the proper position, the surgeon may insert pins through pin holes 1164 and 1166 and into the properly positioned talus 20. Pin holes 1164 and 1166 are positioned inferiorly of the transverse cutting slot 1170. In addition to pin holes 1164 and 1166 being positioned to help attach talus guide 1150 to the talus 20, the pin holes 1164 and 1166 may be positioned to align with the medial and lateral inferior walls of the talus implant so that, when the medial and lateral walls of the talus are prepared to receive the talus implant, there are no holes remaining from pins that were previously inserted through pin holes 1164 and 1166. Other pin holes that are not illustrated in FIGS. 11A-F may be provided to give a surgeon additional options for attachment, including pin holes on one or both of the medial and lateral wings 1177, 1178 of the stabilizer 1176. It should be noted that, similar to tibia guide 1100, talus guide 1150 may include one or more fixation blocks, 1184, 1186, which may assist in the fixation of the talus guide 1150 during manufacturing operations.

Figure 11J:
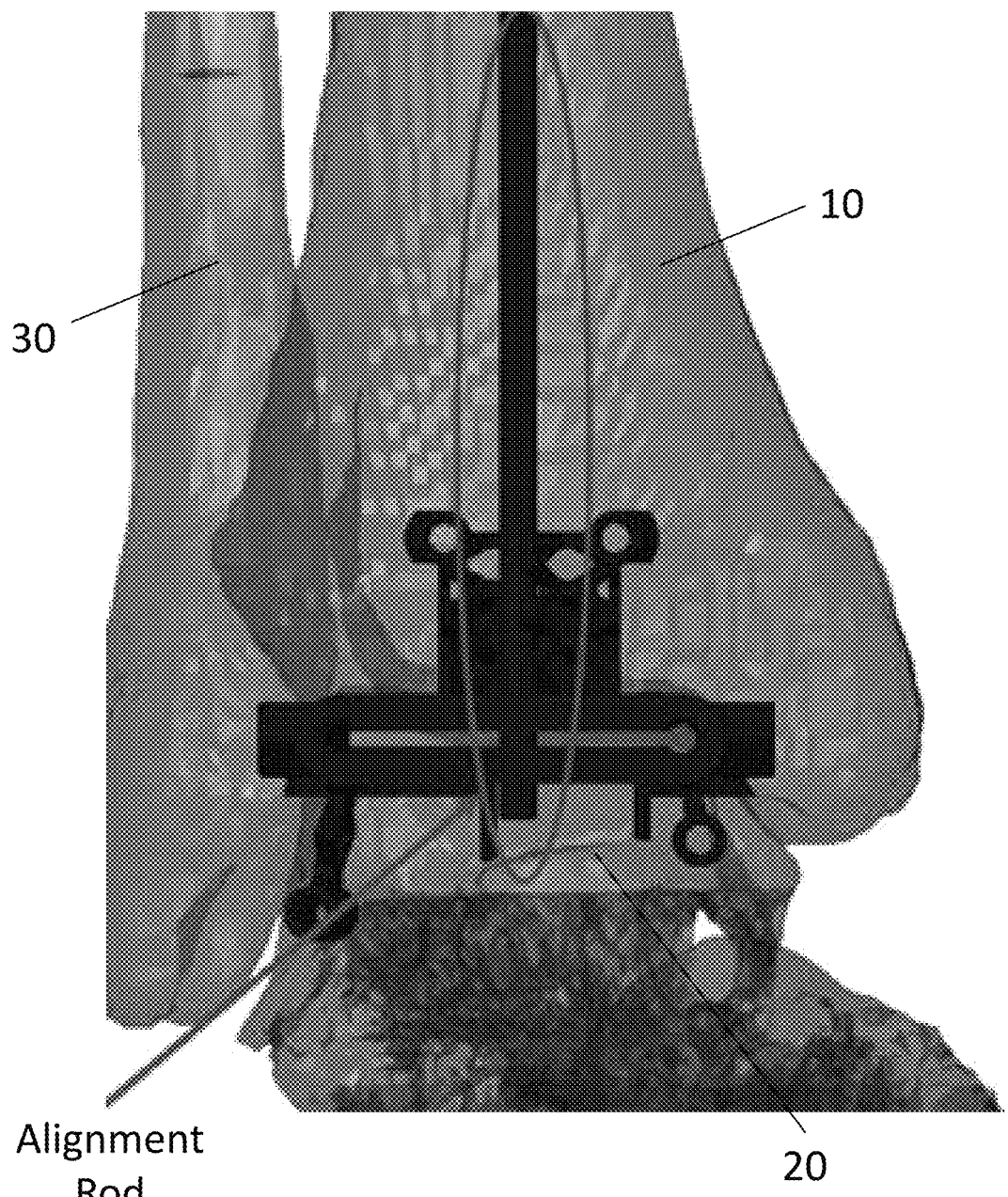
FIGS. 11J-K are views of different alignments rods coupled to the talus guide of FIGS. 11A-E while the talus guide is coupled to the patient's talus.
Figure 11K:
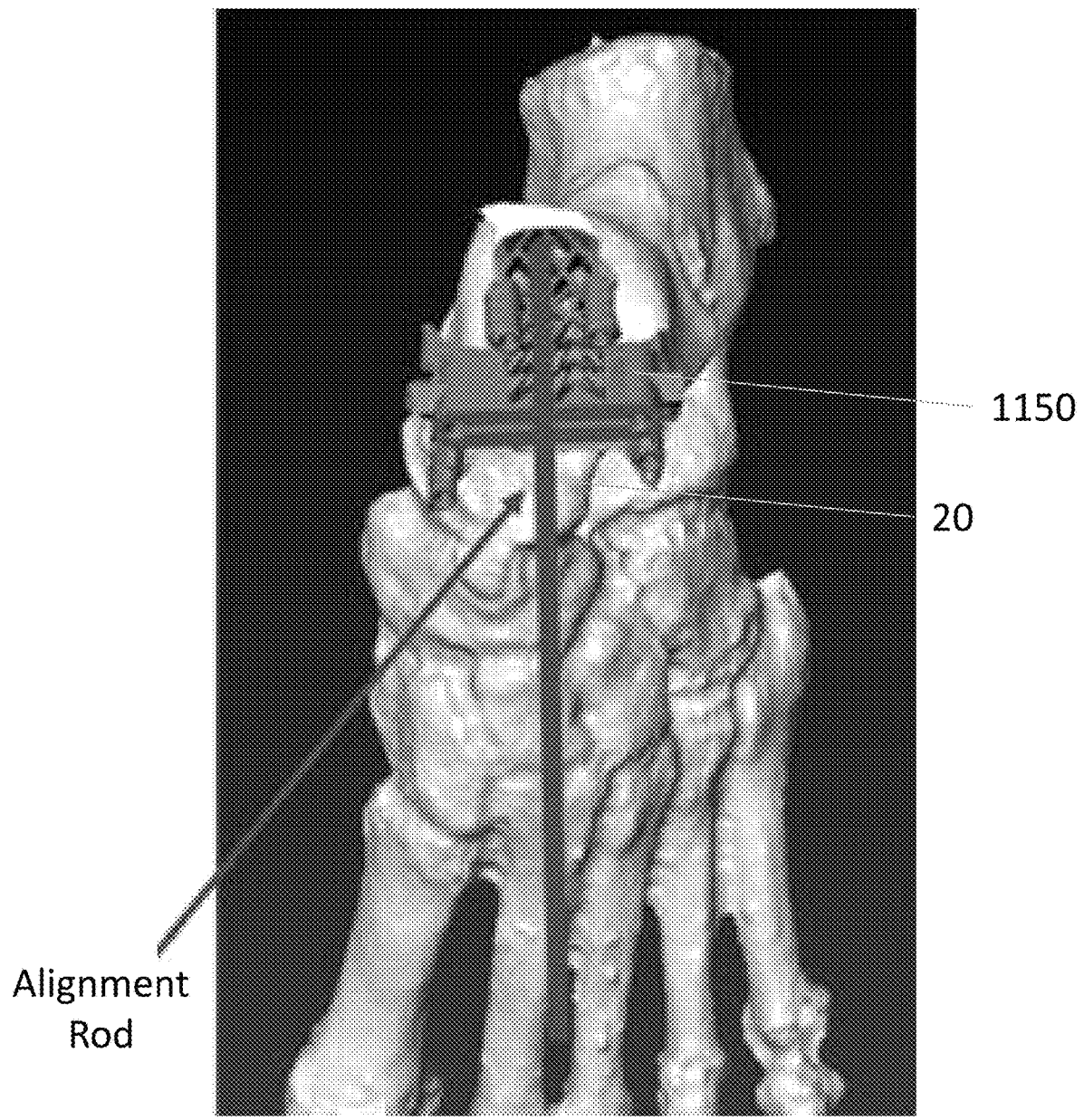

Talus guide 1150 may include a first alignment hole 1182 and a second alignment hole 1183, each alignment hole adapted to receive an alignment rod therethrough. Alignment hole 1182 may include a top opening (best shown in FIG. 11E) and a bottom opening (FIG. 11F), the alignment hole 1182 extending substantially orthogonal to transverse cutting slot 1170. Similar to the tibia guide 1100, an alignment rod may be passed through alignment hole 1182 to check for desired alignment of the talus guide 1150 to the talus 20 and/or tibia 10, as shown in FIG. 11J. Alignment hole 1183, best shown in FIGS. 11A and 11E, may extend in an anterior-to-posterior direction substantially parallel to the anterior-to-posterior passage within slot 1170 and may be aligned with the anterior-to-posterior vector of the angled pin hole 1190. As shown in FIG. 11K, an alignment rod may be positioned within alignment hole 1183 to check the suitability of the alignment of the patient's forefoot.

Figure 12A:
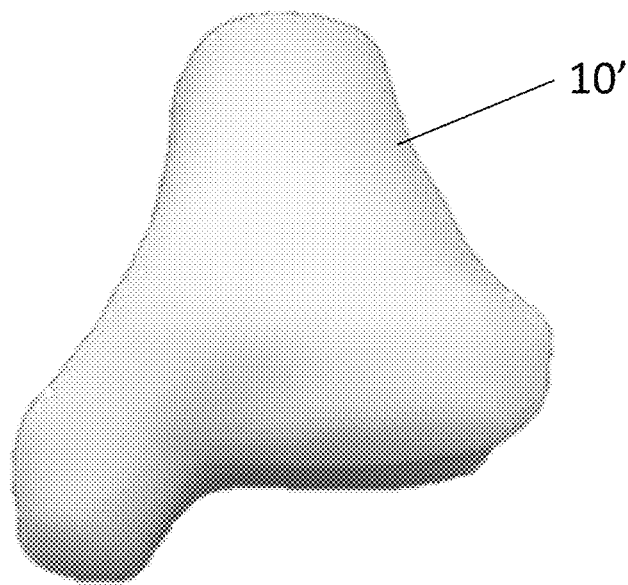
FIGS. 12A-B are views of physical models of a patient's distal tibia and talus.
Figure 12B:
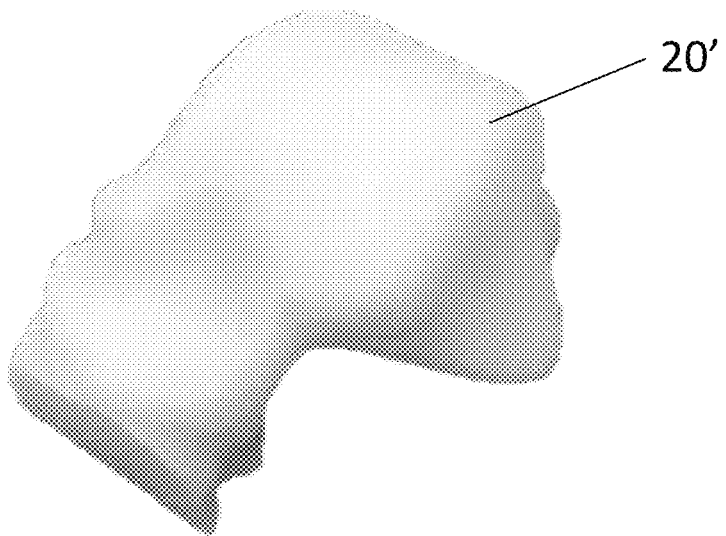

Tibia guides and talus guides, including those described herein, may be provided to the surgeon or other personnel with physical model bones to assist the surgeon. For example, an accurate three-dimensional physical model of the patient's distal tibia 10' is shown in FIG. 12A, and may be provided along with a patient specific tibia guide such as tibia guide 1100. Similarly, an accurate three-dimensional physical model of the patient's talus 20' may be provided along with a patient specific talus guide such as talus guide 1150. These physical models 10' and 20' may be used preoperatively by the surgeon to help explain the surgery to the patients and also to help with additional case planning as may be necessary. The physical models 10' and 20' may also be used intraoperatively as a basis for comparing the fit of the relevant guides 1100 and 1150 to the patient's native bone.

Figure 13A:
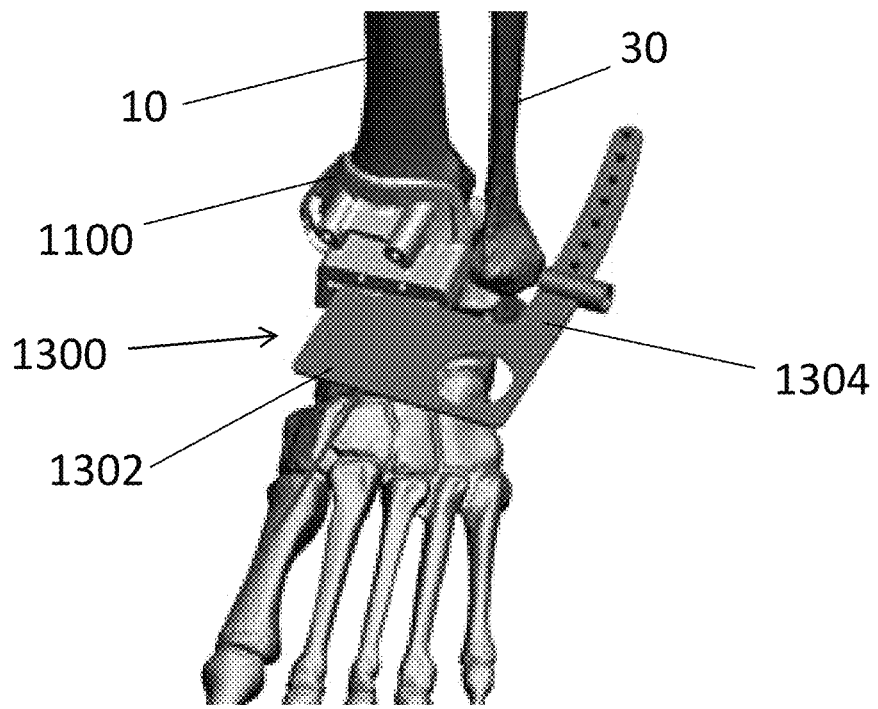
FIG. 13A is a perspective view of a wing accessory coupled to the tibia guide of FIGS. 10A-D, with the tibia guide attached to the patient's tibia.
Figure 13B:
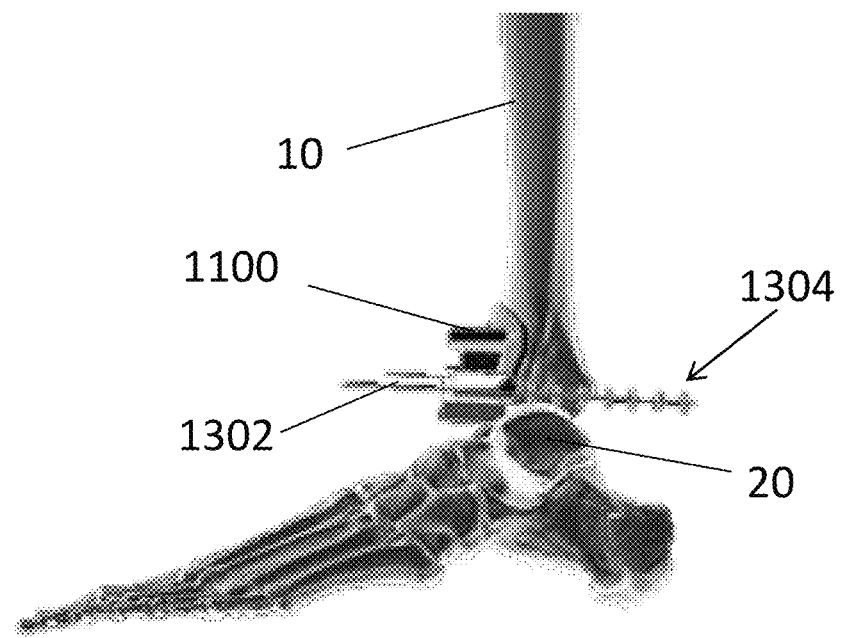
FIG. 13B is a lateral fluoroscopic view of the assembly as shown in FIG. 13A.

FIG. 13A illustrates a wing accessory 1300 that may be used with tibia guide 1100, or any other tibia guide described herein. Wing accessory 1300 may include a first portion adapted for insertion into the transverse cutting guide slot 1122 when the tibia guide 1100 is coupled to the tibia, but prior to making the transverse resection. It should be understood that the portion of the wing accessory 1300 inserted into transverse slot 1122 is not visible in FIG. 13A. Wing accessory 1300 may also include a main body 1302 that is coplanar to the transverse cutting slot 1122 when the wing accessory 1300 is inserted in the cutting slot 1122. Wing accessory 1300 may further include an extension member 1304 extending from the main body 1302, the extension member 1304 also being coplanar with the transverse cutting slot 1122 when the wing accessory 1300 is coupled to tibia guide 1100. As shown in FIG. 13A, the extension member 1304 may be adapted to extend in an anterior to posterior direction adjacent the distal tibia 10 when the wing accessory 1300 is coupled to tibia guide 1100. Prior to resecting the tibia 10, the wing accessory 1300 may be coupled to tibia guide 1100 and an X-ray or other suitable imaging technique may be used to image the extension member 1304 relative to the tibia 10, for example using a lateral X-ray as shown in FIG. 13B. The extension portion 1304 may readily show the surgeon where the resection in the tibia 10 will be located if the transverse cutting slot 1122 is used, helping the surgeon confirm proper placement. The extension member 1304 may include a plurality of pins or other protrusions that may be used to indicate distances. For example, each pin or protrusion may be spaced an equal distance from an adjacent pin or protrusion, for example about 10 mm from the center of one pin to the center of the next pin. In addition, each pin may extend an equal distance above and below the extension member 1304, for example about 5 mm above and about 5 mm below the extension member 1304. Such features may assist the surgeon in determining or confirming relevant distances, such as desired cut distances. It should be understood that the wing accessory may be similarly used with the talus guide 1150 to determine or confirm relevant cut distances and alignment of the talus guide 1150 relative to the talus 20. Wing accessory 1300 may include a hole or other aperture that may assist a user in grasping the wing accessory 1300, for example by pulling the wing accessory 1300 to remove the wing accessory from the cutting guide slot 1122.

Figure 14A:
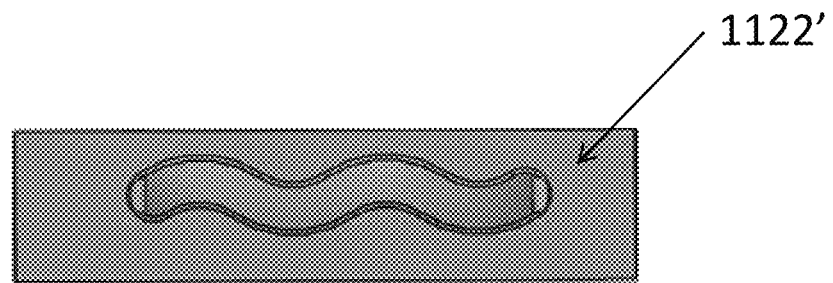
FIG. 14A shows an alternative version of a transverse cutting slot for use in a tibia or talus cut guide.
Figure 14B:
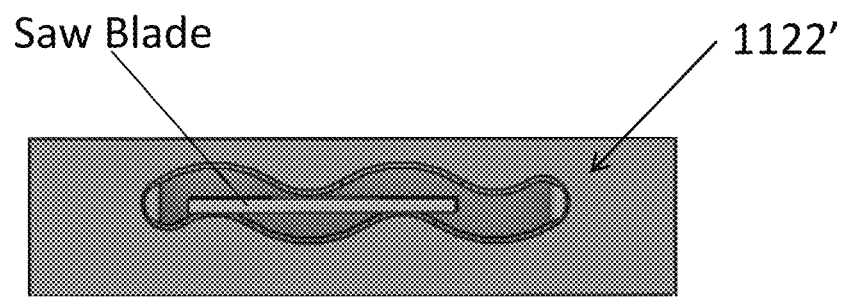
FIG. 14B shows a saw blade positioned within the transverse cutting slot of FIG. 14A.
Figure 14C:
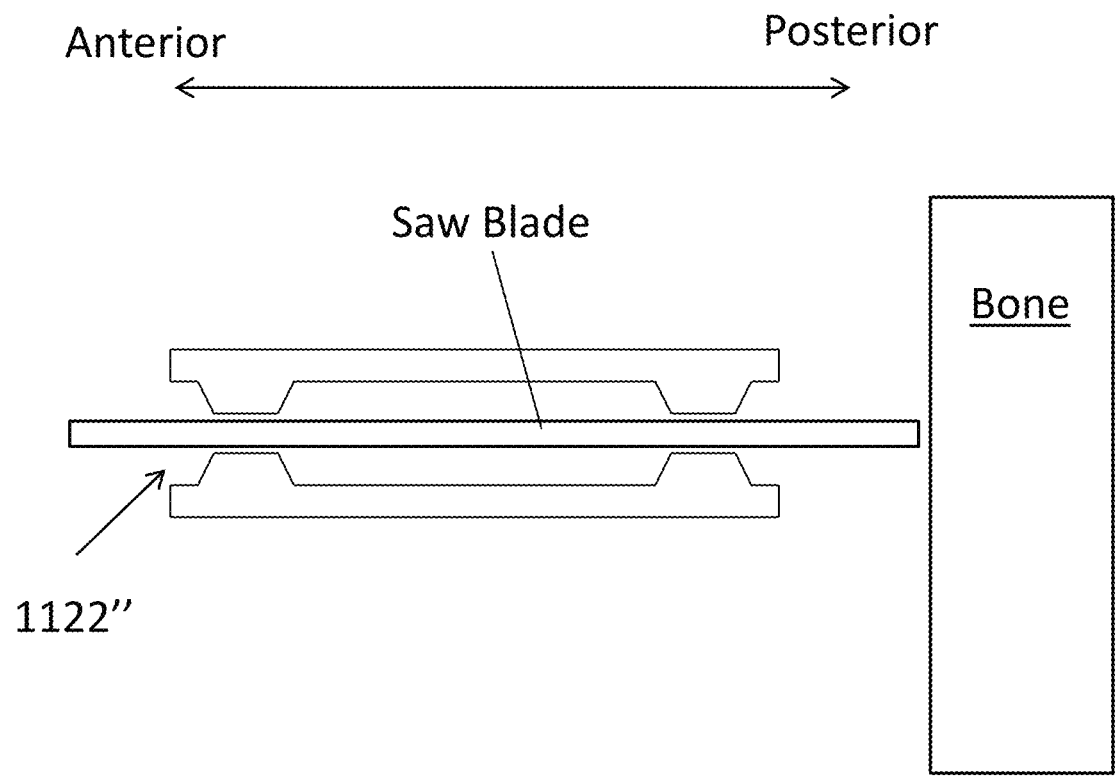
FIG. 14C shows a saw blade positioned with a further alternative version of a transverse cutting slot for use in a tibia or talus cut guide.

FIG. 14A shows an alternative construction of a transverse cutting slot 1122' that may be used in place of transverse cutting slot 1122 of tibia guide 1100, or in place of any other transverse cutting slot of any tibia or talus guide described herein. Compared to transverse cutting slot 1122, which is substantially planar and bounded by parallel straight walls, transverse cutting slot 1122' may be defined by top and bottom walls that are "wavy," where the top wall includes peaks that align with troughs of the bottom wall, and the bottom wall includes peaks that align with troughs of the top wall. With this configuration, as shown in FIG. 14B, a saw blade or other cutting tool may still be guided to make a substantially planar cut, but the saw blade may only contact the peaks of the top and bottom walls that define the transverse cutting slot 1122'. Compared to cutting slot 1122, a saw blade through cutting slot 1122' may have fewer areas of contact with surfaces of the cutting guide, which may lead to less cutting or damaging of both the saw blade and the walls that define the cutting slot 1122'. FIG. 14C shows a further alternative construction of a transverse cutting slot 1122", which may be used in place of any transverse cutting slots described herein. As shown in FIG. 14C, the structure forming the transverse cutting slot 1122" may include a first pair of anterior and posterior bump-outs or extensions that extend inferiorly from the superior surface of the cutting slot in a medial-to-lateral direction, and a second pair of anterior and posterior bump-outs or extensions that extend superiorly from the inferior surface of the cutting slot in a medial-to-lateral direction. The two anterior bump-outs may be positioned adjacent one another, and the two posterior bump-outs may be positioned adjacent one another, to provide the main points of contact between the saw blade and the structure forming the cutting slot 1122". With this configuration, there is little or no contact between the saw blade and the structure that defines the cutting slot 1122" between the anterior and posterior bump-outs, helping to reduce the overall area of contact between the saw blade and the cutting guide. The geometry of the transverse cutting slot 1122" shown in FIG. 14C may be beneficial from a manufacturing standpoint, as it may be simpler to create compared to more complex shapes that achieve a similar goal. It should also be understood that similar bump-outs to those illustrated for the cutting slot in FIG. 14C may be utilized in any of the apertures described herein that function to receive pins through the apertures.

Figure 15A:
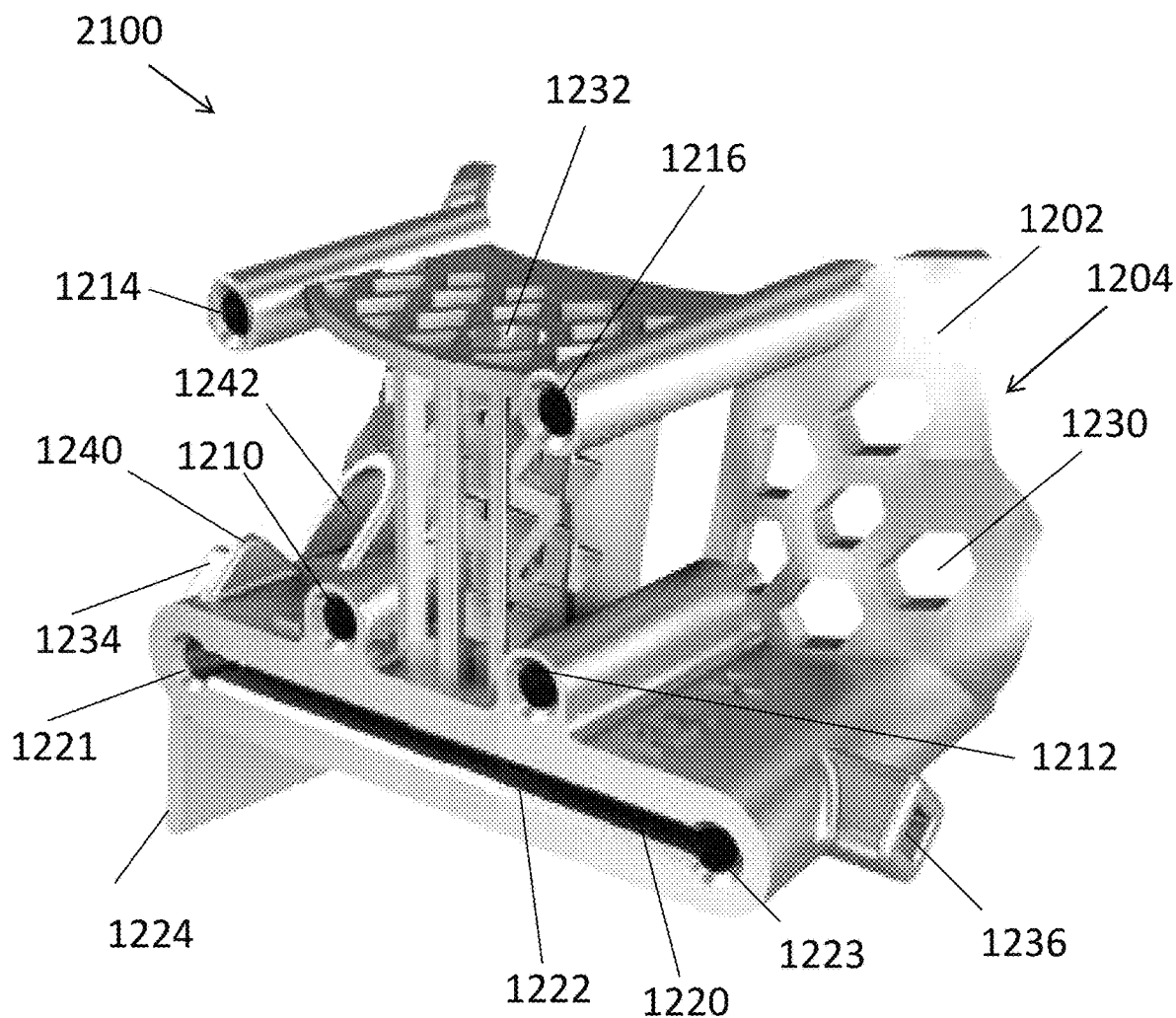
FIGS. 15A-C show various views of a tibial cutting guide according to another aspect of the disclosure.
Figure 15B:
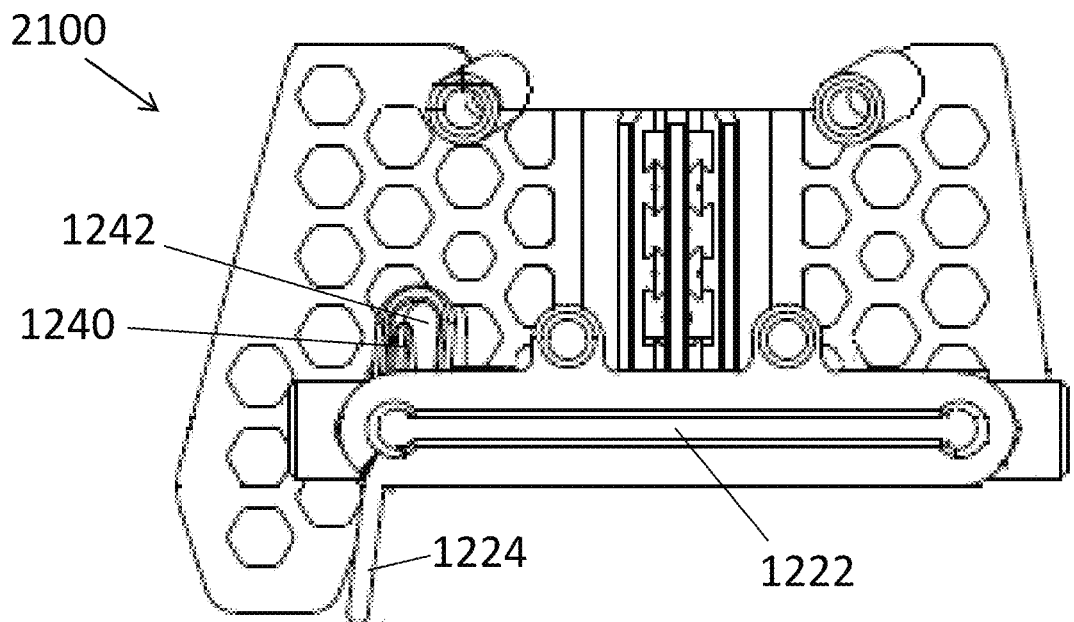
Figure 15C:
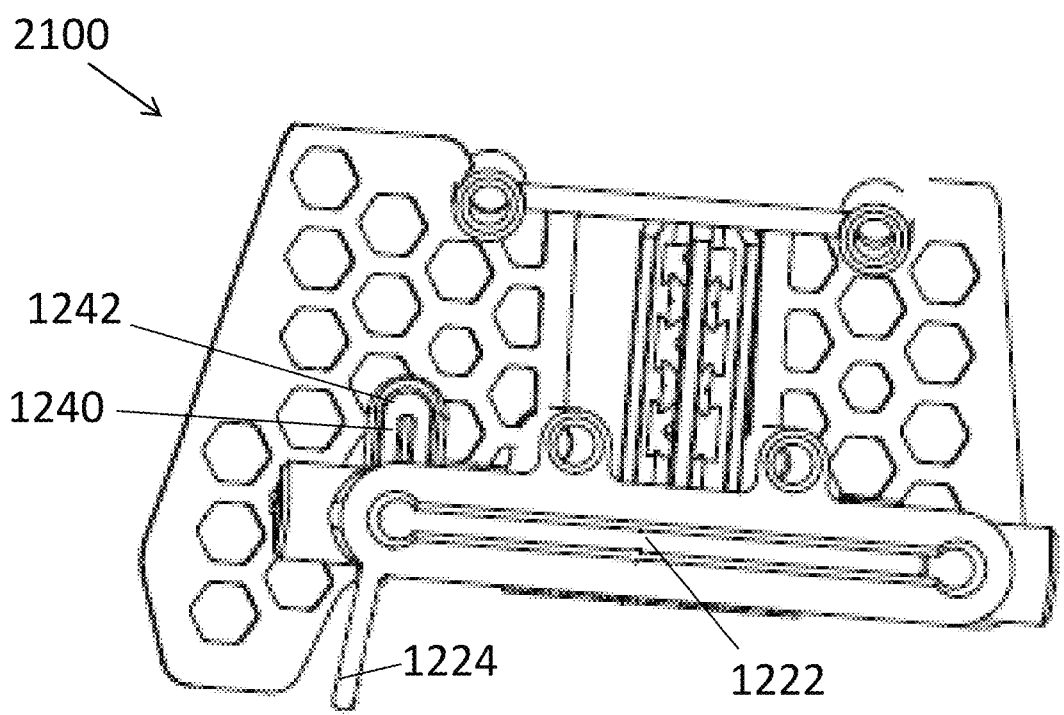

FIGS. 15A-C illustrate another embodiment of a patient-specific tibia guide 1200 that is similar to tibia guide 1100 in most respects. Tibia guide 1200 may have various features similar to other tibia guides described herein, including tibia guides 100 and 1100. For example, tibia guide 1200 includes an anterior surface 1202 and a posterior bone-contacting surface 1204 opposite the anterior surface 1202. Tibia guide 1200 is configured to attach to the anterior surface of the patient's tibia 10. The posterior bone-contacting surface 1204 may be keyed to the geometry of the patient's tibia 10 so that tibia guide 1200 may fit onto the patient's tibia 10 in only one (or substantially only one) position and orientation. In addition, the posterior bone-contacting surface 1204 may be curved posteriorly from the center toward the medial and lateral edges so that the tibia guide 1200 at least partially wraps around the tibia 10 to increase surface area contact between the tibia guide 1200 and the tibia 10 in the medial-to-lateral direction. Still further, the posterior bone-contacting surface 1204 may be curved posteriorly from the center toward the superior and inferior edges so that the tibia guide 1200 at least partially wraps around the tibia 10 to increase surface area contact between the tibia guide 1200 and the tibia 10 in the superior-to-inferior direction. As in other embodiments described herein, posterior bone-contacting surface 1204 may include a portion that extends medial of and inferior to the transverse cutting guide for placement on the patient's medial malleolus which may further help stabilize the guide.

Two pin holes 1210 and 1212 extend through both the anterior surface 1202 and posterior surface 1204 of the tibia guide 1200 and are sized and shaped to receive fixation pins, or other suitable fixation means, therethrough to fix the tibia guide 1200 to the patient's tibia 10. In the illustrated example, pin holes 1210 and 1212 are positioned superior to a transverse cutting guide slot 1222 of the tibia guide 1200. Pin hole 1210 may be positioned on a medial side of the tibia guide 1200 and pin hole 1212 may be positioned on a lateral side of the tibia guide 1200, with pin holes 1210 and 1212 being positioned substantially the same height from cutting guide slot 1222. In the illustrated embodiment, pin holes 1210 and 1212 are positioned just superior of cutting guide slot 1222. Pin holes 1210 and 1212 may be formed in cylindrical or other shaped projections, in order to provide greater surface area for contact between pins inserted through pin holes 1210 and 1212 and tibia guide 1200. Pin holes 1210 and 1212 may have positions and orientations that correspond to pin hole positions and orientations of a talus guide 1250 so that the talus guide 1250 may be slid over the same pins used to hold the tibia guide 1200 to the patient's tibia 10. Further, pin holes 1210 and 1212 may have positions and orientations that correspond to holes in the tibia implant so that, when the holes are drilled out of the tibia 10 for implantation of the tibia implant, no holes remain in the bone from use of the tibia guide 1200 or the talus guide 1250.

Tibia guide 1200 may include two additional pin holes 1214 and 1216. Pin hole 1214 may be positioned on a medial side of the guide and pin hole 1216 may be positioned on a lateral side of the guide, with both pin holes 1214 and 1216 being positioned near a superior or top end of the guide. Pin holes 1214 and 1216 may be defined within cylindrical projections similar to pin holes 1210 and 1212. Pin holes 1214 and 1216 may be referred to as contingency or "bailout" holes with pin holes 1214 and 1216 only intended for use with a universal cutting guide instead of the patient-specific tibia guide 1200 and talus guide 1250. In other words, if a surgeon decides that the tibia guide 1200 should not be used for any reason, pins may be passed through pin holes 1214 and 1216 into the tibia 10, the tibia guide 1200 may be removed by sliding the guide off the pins, and a traditional universal (i.e. non-patient specific) guide with holes corresponding to the position of pin holes 1214 and 1216 may be used to complete the procedure.

The tibia guide 1200 may also include one or more visualization windows 1230. Windows 1230 may facilitate the surgeon in better visualizing the patient's tibia 10 and checking proper fitting between the tibia guide 1200 and the patient's tibia 10. In the illustrated embodiment, windows 1230 may be in the form of a plurality of cut-outs or other apertures in the portion of tibia guide 1200 contoured to the patient's bone contours, and the cut-outs may extend from the anterior surface 1202 to the posterior surface 1204. In the illustrated embodiment, may of the windows 1230 are honey-comb shaped or hexagonal. As illustrated, windows 1230 include a first group of windows on a lateral side of the tibia guide 1200 and a second group of windows on the medial side of the tibia guide. The windows 1230 may include a plurality of hexagonal shaped cut-outs, as well as other shaped cut-outs, such as substantially diamond-shaped cutouts on a superior surface of the tibial cutting guide 1200. However, it should be understood that other shapes or other groups of shapes may be suitable. In particular, any shaped cut-outs that provide for good visibility while leaving enough structure to maintain structural integrity and rigidity of the tibia guide 1200 may be suitable in place of the specific embodiment shown. Further, these diamond-shaped cutouts or lattice structure may be used, where appropriate, as pin holes to receive pins therethrough.

A cutting guide 1220 may include a first guide portion 1222 and a second guide portion 1224, which may be substantially similar to the cutting guide slot 220 of FIG. 7A and cutting guide slot 1120 of FIG. 10A. The first guide portion 1222 may generally consist of two parallel transverse walls defining a first slot therebetween. This first guide portion 1222 and corresponding first slot are configured to assist the surgeon in creating a flat transverse cut in the patient's tibia 10. Preferably, the slot of the first guide portion 1222 is substantially planar and, when tibia guide 1200 is coupled to the tibia 10, the plane of the slot 1222 is substantially orthogonal to the mechanical axis of the tibia 10. The second guide portion 1224 may consist of a single wall extending at an oblique angle to the first slot 1222, which may in particular be an obtuse angle. However, in some circumstances it may be suitable for the second guide portion 1224 to extend perpendicularly relative to the first slot. The second guide portion 1224 may define a second slot, although in this instance the second slot is generally open because it is bounded on only one side. This second slot may be configured to assist the surgeon in releasing the resected bone from the medial malleolus and/or from the medial side of the tibia, superior to the medial malleolus. The configuration of the first slot being defined by a fully (or nearly fully) enclosed first guide portion 1222 may facilitate a saw blade or other resection tool being directed in a limited intended manner. The configuration of the second slot being open and bounded only by the second guide portion 1224 may provide additional freedom of movement that may be necessary for the surgeon to make the cut. Although the first cutting guide portion 1222 is shown as a slot that is substantially closed, the cutting guide portion may take other forms described above in connection with other embodiments of tibia guides.

In addition to defining the first slot, the first guide portion 1222 may define a first pin hole 1221 at a first end of the first slot relatively near the second guide portion 1224. The first guide portion 1222 may define a second pin hole 1223 on the opposite side of the first slot from the first pin hole 1221. The pin holes 1221 and 1223 may be configured to receive pins, similar to as described above in connection with pin holes 1210 and 1212. Pins extending through pin holes 1221 and 1223 into the patient's tibia 10 may help guide the saw blade, or other cutting tool, as it is inserted through the first and/or second slots and into the patient's tibia 10. In addition, the pins extending through pin holes 1221 and 1223 may help protect soft tissue, hard tissue, and portions of the cutting guides from being unintentionally cut or otherwise damaged. Further, it should be noted that pin holes 1221 and 1223, and/or pins extending through these pin holes, may be calibrated with the tibia guide 1200, based on information from the prior imaging (e.g. CT scan) so that the pins cannot be over inserted.

Tibia guide 1200 may include an alignment hole 1232 adapted to receive an alignment rod therethrough. Alignment hole 1232 may extend from the superior end of tibia guide 1200 and to or through first guide portion 1222, and is preferably orthogonal to the transverse cutting slot defined by the first guide portion 1222. With this configuration, an alignment rod may be passed through alignment hole 1232 to check for desired alignment of the tibia guide 1200 to the tibia 10, similar to the embodiment shown in FIG. 10H. Tibia guide 1200 may also include one or more fixation blocks, 1234, 1236, which may be assist in fixation of the tibia guide 1200 during manufacturing operations. For example, fixation blocks 1234, 1236 may be used to guide a milling machine that creates certain features in the tibia guide 1200. In one example, tibia guide 1200 is additively manufactured, with certain features being milled into the tibia guide 1200, and the fixation blocks 1234, 1236 may assist in guiding the milling process.

The main components of tibia guide 1200 described above are substantially similar to those of tibia guide 1100 already described. One main difference of tibia guide 1200 is the inclusion of a rotational alignment sight. In the illustrated embodiment, the rotational alignment sight includes a projection 1240 extending superiorly from a medial side of the tibia guide 1200 near pin hole 1221. Projection 1240 may take any suitable shape, including a thin member in the medial-to-lateral direction having a generally triangular shape that narrows in the inferior-to-superior direction. The rotational alignment sight may also include an alignment window 1242, which may be define a general "U"-shape profile. As best illustrated in FIGS. 15B-C, the patient's tibia may be rotated to achieve perfect medial gutter perspective, which may be confirmed by the rotational alignment sight. In particular, FIG. 15B illustrates a rotational configuration in which the projection is not aligned with the alignment window 1242, while FIG. 15C illustrates a rotational configuration in which the projection is aligned with the alignment window 1242. However, it should be understood that other shapes and configurations of the projection 1240 and alignment window 1242 may provide similar functionality. For example, a spherical or circular bead and a circular hole may be implemented so that, upon lining up correctly, the spherical or circular bead forms a complete circle with the circular hole. In other embodiments, a single pillar may be provided in a first plane, with a pair of pillars provided in a second plane so that, upon achieving the desired alignment, the single pillar is substantially equidistant between the pair of pillars. Other complementary shapes that provide a visual indication of proper alignment when viewed in a particular orientation with respect to one another may also be suitable for use in this feature.

Figure 16A:
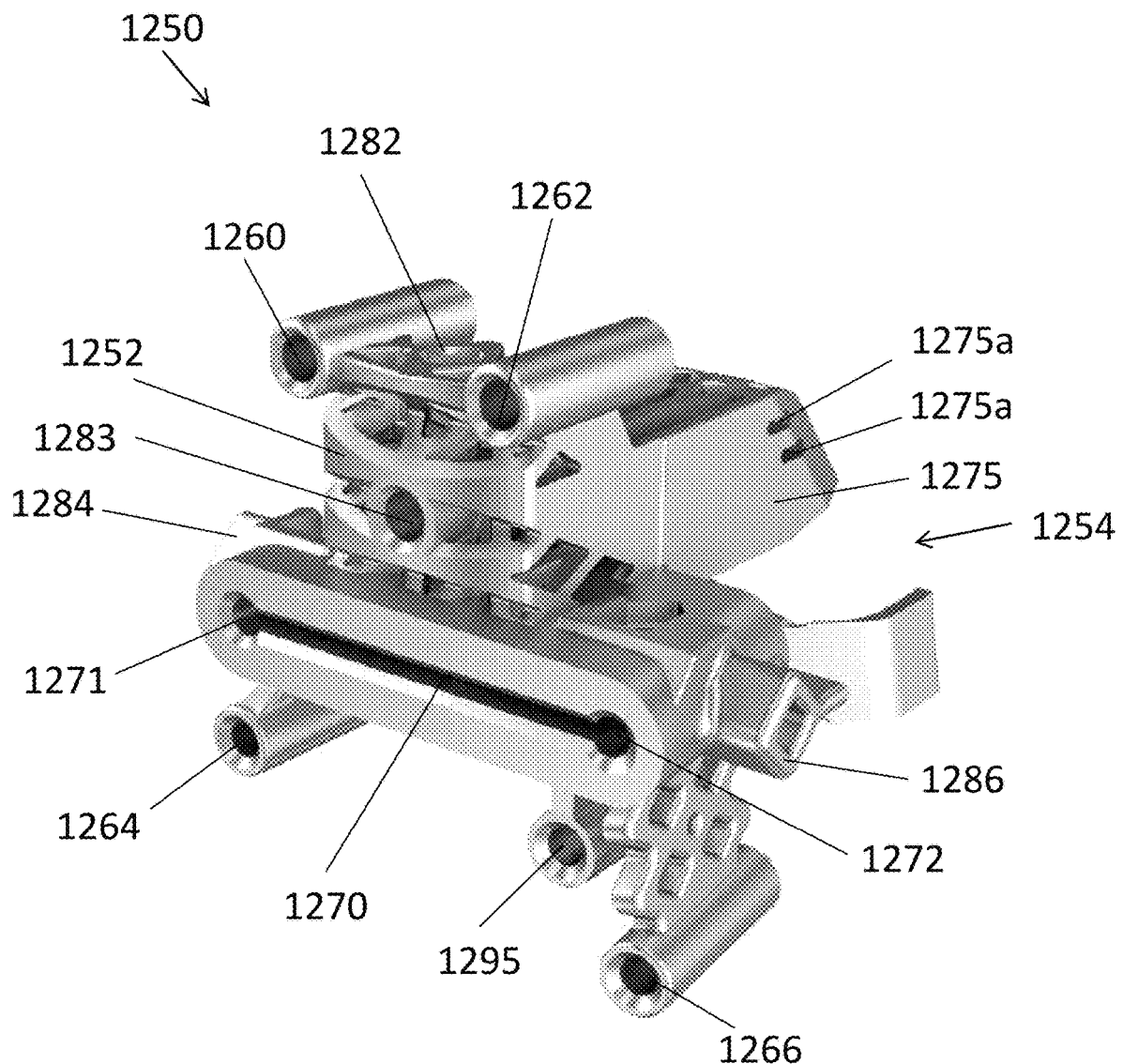
FIGS. 16A-C show various views of a talus cutting guide according to another aspect of the disclosure.
Figure 16B:
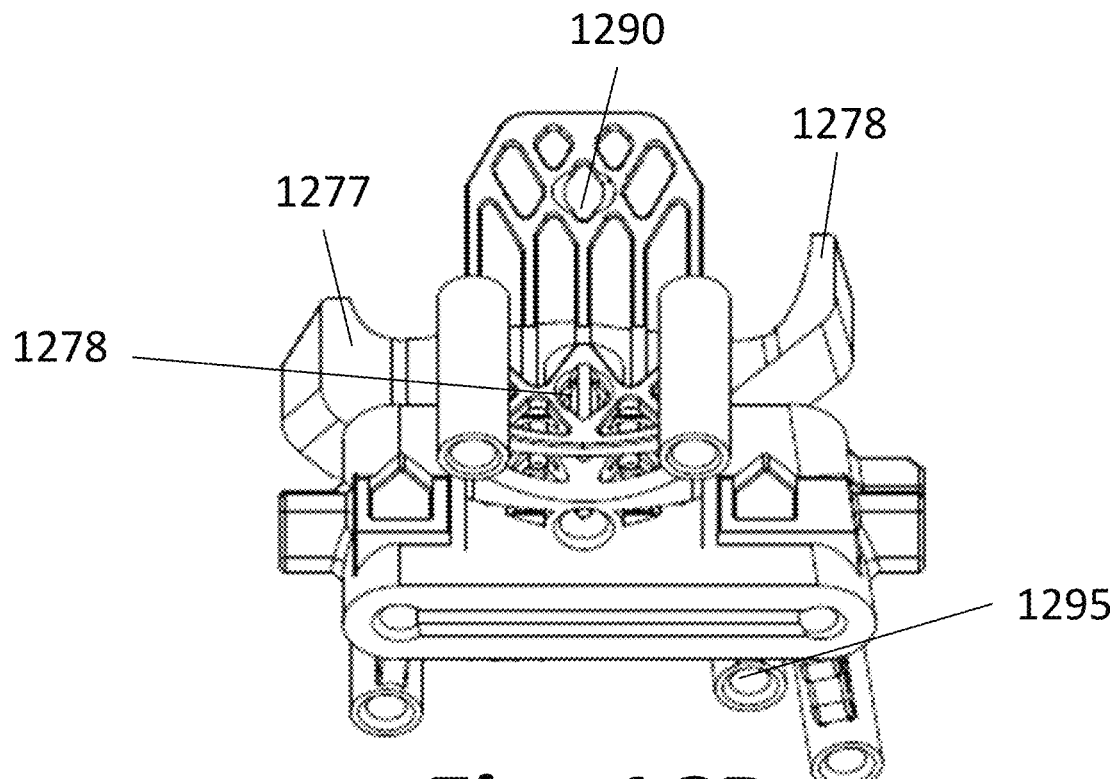
Figure 16C:
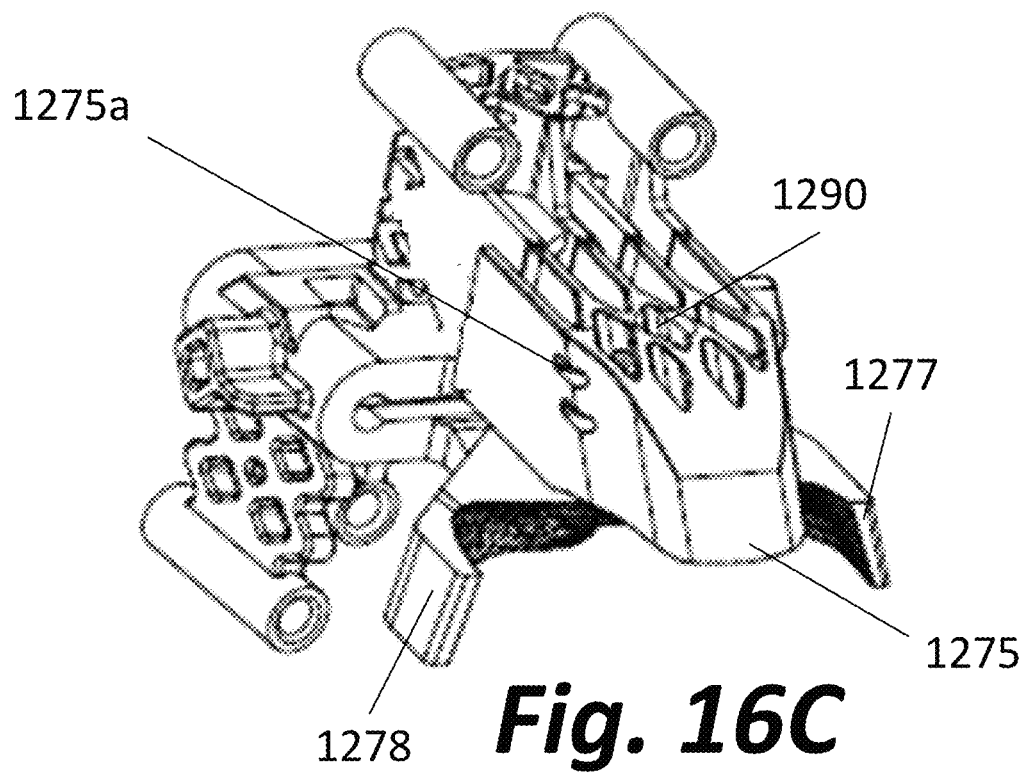

FIGS. 16A-C illustrate another embodiment of a patient-specific talus guide 1250 that is similar to talus guide 1150 in most respects. Talus guide 1250 may have various features similar to other talus guides described herein, including talus guides 150 and 1150. For example, talus guide 1250 may include an anterior surface 1252 and one or more posterior bone-contacting surfaces 1254 described in greater detail below. Talus guide 1250 may include an upper portion configured to attach to the anterior surface of the patient's tibia 10 and a lower portion configured to attach to the anterior surface of the patient's talus 20. The posterior bone-contacting surfaces 2154 of the upper portion and lower portion may be keyed to the geometry of the patient's tibia 10 and talus 20, respectively, so that talus guide 1150 may fit onto the patient's tibia 10 and talus 20 in only (or substantially only) a single position and orientation, as described in greater detail below. As with other talus guides described herein, talus guide 1150 may be coupled to the talus 20 only, or to both the tibia 10 and the talus 20, with any of the contact areas optionally being patient-specific and configured to fit in only one or substantially only one orientation.

Two pin holes 1260 and 1262 may extend through both the anterior surface 1252 and a posterior surface 1254 of the upper portion of the talus guide 1250 and are sized and shaped to receive fixation pins, or other suitable fixation means, therethrough to fix the upper portion of the talus guide 1250 to the patient's tibia 10. In the illustrated example, pin holes 1260 and 1262 are positioned superior to a transverse cutting guide slot 1270 of the talus guide 1250. Pin hole 1260 and may be positioned on a medial side of the talus guide 1250 and pin hole 1262 may be positioned on a lateral side of the talus guide 1250, with pin holes 1260 and 1262 being positioned substantially the same height from transverse slot 1270. Pin holes 1260 and 1262 may be defined by cylindrical or other shaped projections, in order to provide greater surface area for contact between a pin inserted through pin holes 1260 and 1262. Pin holes 1260 and 1262 may have the same size, position, and orientation with respect to one another as pin holes 1210 and 1212 of tibia guide 1200 so that, after use and removal of the tibia guide 1200, the pin holes 1260 and 1262 of the talus guide 1250 may be slipped over the pins that were previously used with pin holes 1210 and 1212 of the tibia guide 1200.

The transverse slot 1270 may be defined by a guide portion generally consisting of two parallel walls defining the transverse slot 1270 therebetween. Transverse slot 1270 may be configured to assist the surgeon in creating a flat transverse cut in the patient's talus 20. The transverse slot 1270 may be fully enclosed to facilitate a saw blade or other resection tool being directed in a limited intended manner. The parallel walls defining the transverse slot 1270 may also define a first pin hole 1271 on a medial side of the talus guide 1250 and a second pin hole 1272 on a lateral side of the talus guide 1250. The pin holes 1271 and 1272 may be configured to receive pins, similar to as described above in connection with pin holes 1260 and 1262. Pins extending through pin holes 1271 and 1272 and into the patient's talus 20 may help guide the saw blade, or other cutting tool, as it is inserted through the transverse cutting slot 1270 and into the patient's talus 20. In addition, the pins extending through pin holes 1271 and 1272 may help protect soft tissue, hard tissue, and portions of the cutting guide from being unintentionally cut or otherwise damaged.

The talus guide 1250 may include a protrusion in the form of a tongue or paddle 1275 extending posteriorly from an area of the talus guide 1250 between the upper portion and lower portion and superior to the transverse slot 1270. The paddle 1275 may be configured for insertion between the resected surface of the distal tibia 10 and the unresected proximal surface of the talus 20. Paddle 1275 is preferably sized and shaped to provide additional surface area contact between talus guide 1250 and the tibia 10 and talus 20, which may better support the foot after the tibia 20 has been cut. This support may be particularly useful during the step of resecting the talus 20 with a blade or other cutting tool through transverse slot 1270. All or some parts of paddle 1275 may be patient specific in order to match corresponding surfaces of the bone, although in some embodiments the paddle 1275 need not have any patient specific features. For example, a posterior portion of the inferior side of paddle 1275 may have a surface contour that matches the contours of the anterior/superior surfaces of the talus dome, similar to the embodiment shown in FIG. 11H. In addition, paddle 1275 may include an angled pin hole 1290 to guide the datum pin into place so the surgeon can attach the existing datum pin cutting guides. Paddle 1275 may also help serve as a joint space evaluator to help ensure enough bone was removed from the patient so that the implants will fit on the prepared bone surface, with the height of the paddle 1275 being based on the patient's anatomy and the amount of bone to be resected. It should be understood that, in some embodiments, the paddle 1275 may be configured to provide relatively little contact with the bone, and an additional stabilizer (such as a stabilizer including wings 1277, 1278 described in greater detail below) may provide most of the desired or necessary contact area (which contact may be patient specific) between the talus guide 1250 and the patient's bone. It should be understood that, even while paddle 1275 is larger in talus guide 1250 compared to the paddle 1275' in talus guide 1250', the wings of the stabilizer may provide the primary contact area between the talus guide and the patient's talus in both embodiments.

Talus guide 1250 may include an additional stabilizer, which is best shown in FIGS. 16B-C. The additional stabilizer may include a medial wing 1277 and a lateral wing 1278 adapted to contact the medial and lateral aspects of the dome of the talus 20. Medial and lateral wings 1277, 1278 may each extend away from a center portion of the stabilizer and curve posteriorly, with the surfaces preferably including contours that match the contours of the patient's talus 20 to help provide better stabilization of the talus guide 1250 on the talus. Although not shown in connection with FIGS. 16A-C, the stabilizer may include two posterior rails, similar to posterior rails 1179 of talus guide 1150 shown in FIG. 11F.

As noted above, pin holes 1260 and 1262 of talus guide 1250 may be slid over pins protruding from the tibia 10 that were previously engaged with the tibia guide 1200. Prior to resecting the talus 20, the patient's foot may be rotated so that the talus 20 is in proper contact with the paddle 1275 and the stabilizer of talus guide 1250. Once the talus 20 is in the proper position, the surgeon may insert pins through pin holes 1264 and 1266 and into the properly positioned talus 20. Pin holes 1264 and 1266 are positioned inferiorly of the transverse cutting slot 1270. It should be noted that, similar to tibia guide 1200, talus guide 1250 may include one or more fixation blocks, 1284, 1286, which may assist in the fixation of the talus guide 1250 during manufacturing operations. For example, fixation blocks 1284, 1286 may be used to guide a milling machine that creates certain features in the talus guide 1250. In one example, talus guide 1250 is additively manufactured, with certain features being milled into the talus guide 1250, and the fixation blocks 1284, 1286 may assist in guiding the milling process.

Talus guide 1250 may include a first alignment hole 1282 and a second alignment hole 1283, each alignment hole adapted to receive an alignment rod therethrough. Alignment hole 1282 may include a top opening and a bottom opening, the alignment hole 1282 extending substantially orthogonal to transverse cutting slot 1270. Similar to the tibia guide 1200, an alignment rod may be passed through alignment hole 1282 to check for desired alignment of the talus guide 1250 to the talus 20 and/or tibia 10, similar to the embodiment shown in FIG. 11J. Alignment hole 1283 may extend in an anterior-to-posterior direction substantially parallel to the anterior-to-posterior passage within slot 1270 and may be aligned with the anterior-to-posterior vector of the angled pin hole 1290. Similar to the embodiment shown in FIG. 11K, an alignment rod may be positioned within alignment hole 1283 to check the suitability of the alignment of the patient's forefoot.

Although most of the features of talus guide 1250 described above are similar to corresponding features of talus guide 1150, talus guide 1250 has additional features. For example, as best seen in FIGS. 16A and 16C, tongue or paddle 1275 may include one, two, or more cutouts 1275a or other indicia. In the illustrated embodiment, paddle 1275 includes two cutouts 1275a which are positioned along an axis that corresponds to the channel that extends along angled pin hole 1290. In other words, when the datum pin is passed through the angled pin hole 1290, the axis of the datum pin aligns with the cutouts 1275a. Thus, the cutouts 1275a may provide an indication to the user of the trajectory that the datum pin will have, prior to actually being inserted into angled pin hole 1290. In other embodiments, the cutouts 1275a may take the form of indicia such as markings or lines on the paddle 1275.

Referring to FIGS. 16A and 16B, talus guide 1250 may include an auxiliary pin hole 1295. Auxiliary pin hole 1295 is shown as positioned inferior to cutting guide slot 1270 and between pin holes 1264 and 1266, closer to pin hole 1266. Pin hole 1295 may be generally similar in structure and function to pin holes 1264 and 1266, providing an option for additional stabilization of the talus guide 1250 by passing a fixation pin through the auxiliary pin hole 1295 into the talus 20. In other embodiments the auxiliary pin hole 1295 may be positioned in other locations, for example closer to pin hole 1264, and in further embodiments multiple auxiliary pin holes may be included for additional stabilization options.

Figure 17A:
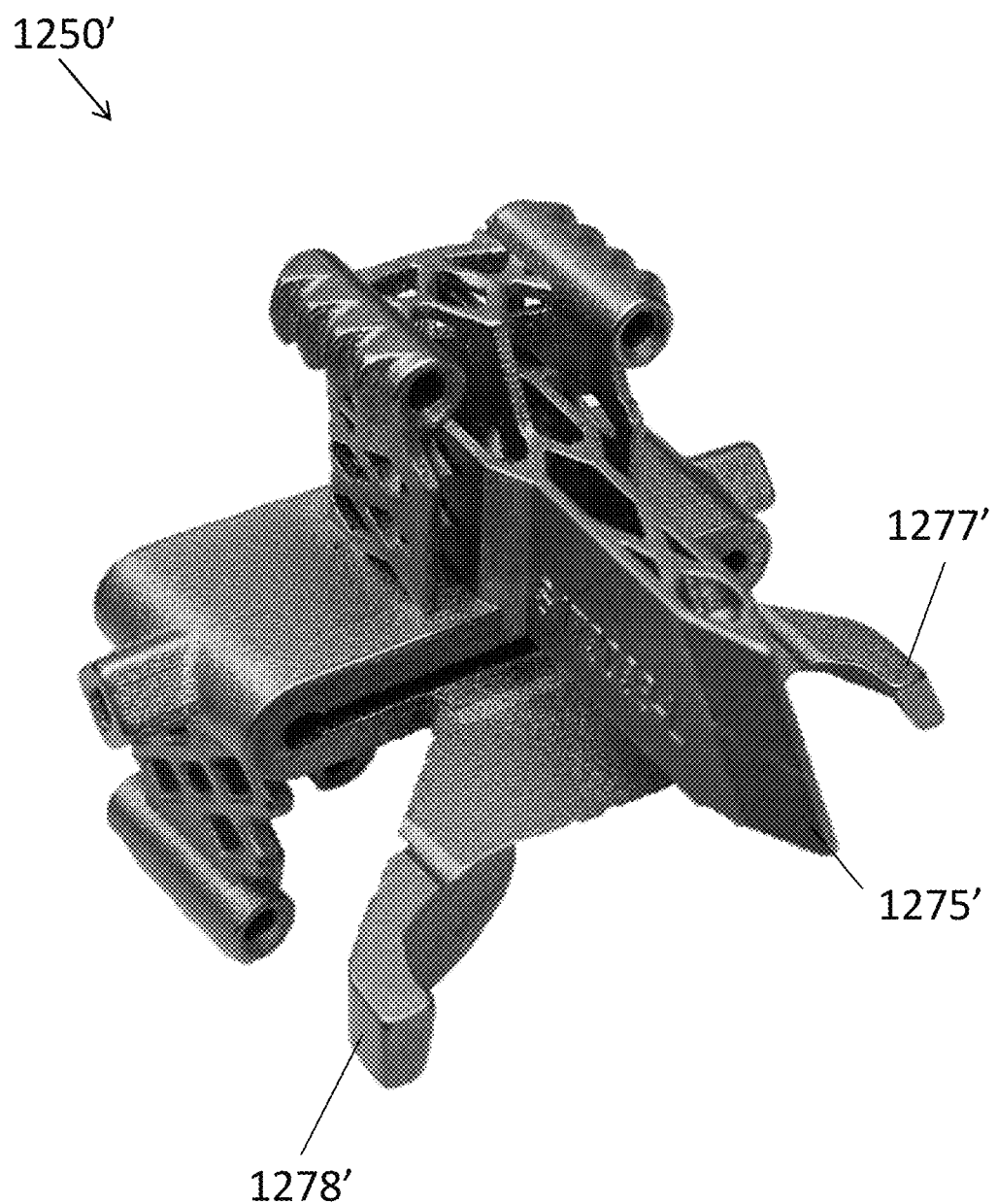
FIGS. 17A-B are top and bottom perspective views, respectively, of a talus cutting guide according to a further aspect of the disclosure.
Figure 17B:
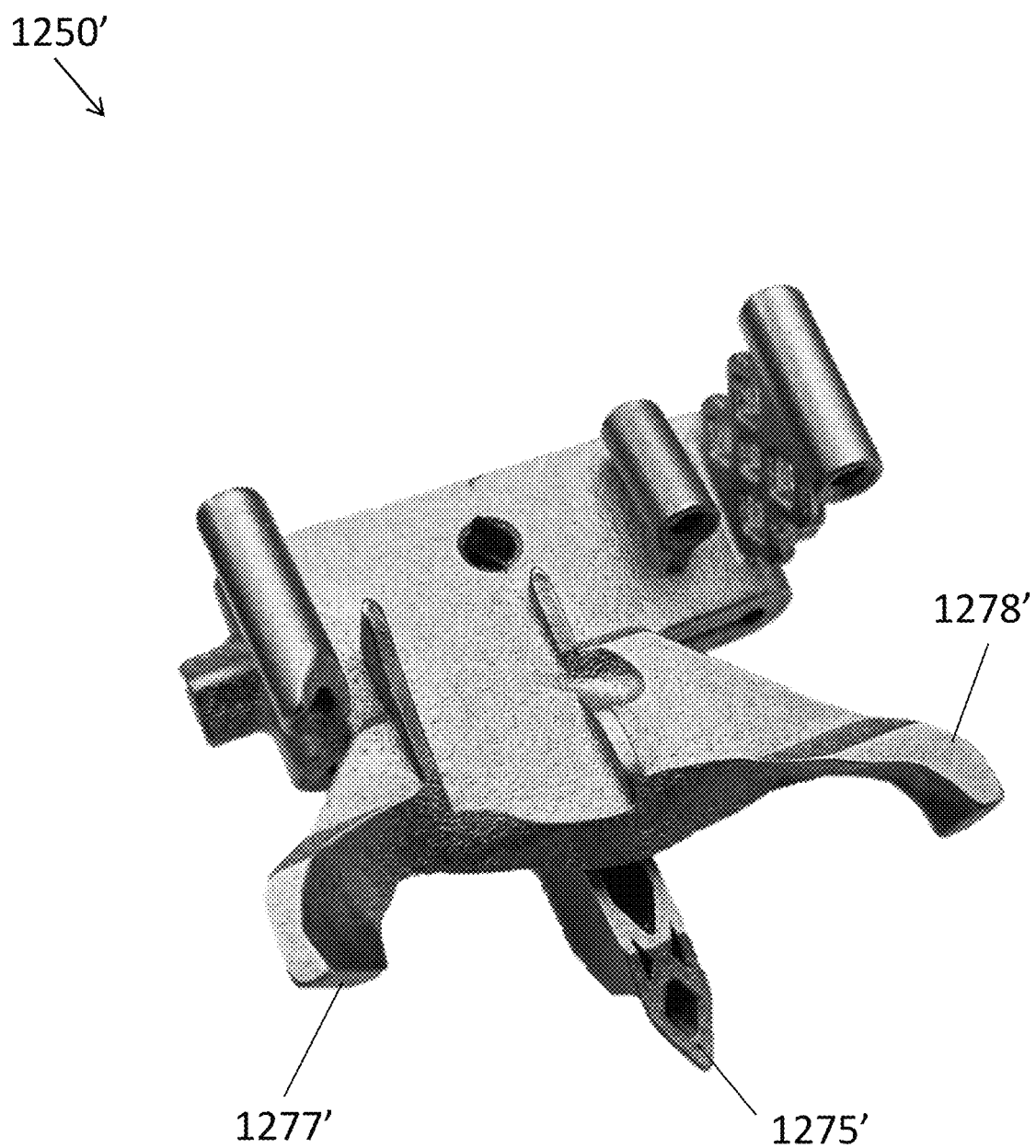

FIGS. 17A-B are top and bottom perspective views, respectively, of a talus guide 1250' that is similar or identical to talus guide 1250 in almost all respects, with the exception of the paddle 1275'. Thus, other aspects of the talus guide 1250' are not described again here. As is clear from the figures, paddle 1275' has a generally similar shape and function as paddle 1275, except that paddle 1275' has a significantly smaller width in the medial-to-lateral direction compared to paddle 1275. With this configuration, paddle 1275' may provide a relatively small amount of the overall patient-specific contact between talus guide 1275' and the patient's tibia 10 and/or talus 20. Rather, the medial wing 1277' and lateral wing 1278' of the stabilizer of talus guide 1250', which may be substantially similar to the medial wing 1277 and lateral wing 1278 of talus guide 1250, may be the primary patient-specific contact surfaces between the talus guide 1250' and the patient's bone.

For the various transverse cutting slots described above, including those in connection with tibia guides 1100, 2100 and talus guides 1150, 1250, 1250', the posterior or bone-facing sides of the slots may be formed in patient-specific surfaces of the posterior surface, or otherwise in separate non-patient-specific surfaces of the posterior surface. Further, the various tibia guides and talus guides described herein may be formed from any suitable materials, including plastics or metals, such as commercially pure titanium (CPTi) or stainless steel. The tibia guides and talus guides may also be formed via any suitable manufacturing modality, including via additive manufacturing such as 3D printing. If additive manufacturing is used to form the tibia guides and/or talus guides described herein, the guides may be intentionally "overbuilt" in certain areas, and those "overbuilt" areas may be milled down or otherwise modified via subtractive manufacturing to create accurate/precise geometries and features in those areas.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A cutting guide for assistance in performing an arthroplasty procedure on a bone, the cutting guide comprising:
 a first guide member defining a transverse cutting slot and having an anterior entrance and a posterior exit, wherein the transverse cutting slot is configured to guide a cutting instrument when the bone is engaged to the cutting guide,
 wherein the transverse cutting slot includes a top wall and a bottom wall, the top wall being defined by a first series of curves having alternating peaks and troughs, the bottom wall being defined by a second series of curves having alternating peaks and troughs, each peak of the top wall being aligned in a superior-to-inferior direction with a corresponding trough of the bottom wall, and each peak of the bottom wall is aligned in the superior-to-inferior direction with a corresponding trough of the top wall,
 a paddle member having a first mating surface configured to engage a non-resected bone surface of the bone in a first matching manner on account of a patient-specific nature of the first mating surface, the first matching manner registering a single relative position of the first mating surface relative to the non-resected bone surface of the bone, and
 a stabilizer member having a second mating surface configured to engage the non-resected bone surface of the bone in a second matching manner on account of a patient-specific nature of the second mating surface, the second matching manner registering a single relative position of the second mating surface relative to the non-resected bone surface of the bone, the first guide member is positioned inferior to the paddle member, and the stabilizer member is positioned inferior to the first guide member, wherein the stabilizer member has a first rail and a second rail each extending in an anterior-to-posterior direction, the second mating surface of the stabilizer member being positioned on inferior surfaces of the first rail and the second rail.

2. The cutting guide of claim 1, further comprising:
 a posterior surface having a mating surface configured to engage a non-resected surface of the bone in a matching manner on account of a patient-specific nature of the mating surface, the matching manner registering a single relative position of the mating surface relative to the non-resected bone surface.

3. The cutting guide of claim 2, wherein the bone is a tibia, and the arthroplasty procedure is an ankle arthroplasty procedure.

4. The cutting guide of claim 3, wherein the cutting guide further includes a second guide member coupled to the first guide member, the second guide member defining an angled guide surface angled obliquely to the transverse cutting slot.

5. The cutting guide of claim 4, wherein the mating surface has a first curvature that is curved posteriorly from a central area of the mating surface toward a medial and a lateral edge of the mating surface so that the central area of the mating surface is positioned anterior to the medial and lateral edges of the mating surface.

6. The cutting guide of claim 5, wherein the mating surface has a second curvature that is curved posteriorly from the central area of the mating surface toward a superior and an inferior edge of the mating surface so that the central area of the mating surface is positioned anterior to the superior and inferior edges of the mating surface.

7. The cutting guide of claim 1, wherein the bone is a talus, and the arthroplasty procedure is an ankle arthroplasty procedure.

8. The cutting guide of claim 1, wherein the stabilizer member has a medial wing portion and a lateral wing portion, the second mating surface of the stabilizer member being positioned on the medial and lateral wing portions.

9. The cutting guide of claim 1, wherein the first mating surface of the paddle member is positioned on a posterior and inferior end of the paddle member.

10. The cutting guide of claim 1, wherein the paddle member includes an angled pin hole extending at an oblique angle to the transverse cutting slot.

11. A cutting guide for assistance in performing an arthroplasty procedure on a bone, the cutting guide comprising:
    a first guide member defining a transverse cutting slot and having an anterior entrance and a posterior exit, wherein the transverse cutting slot is configured to guide a cutting instrument when the bone is engaged to the cutting guide,
    wherein the transverse cutting slot includes a top wall defined by a series of first curves having peaks and troughs, and a bottom wall defined by a series of second curves having peaks and troughs, a radius of curvature of the first curves being substantially the same as a radius of curvature of the second curves such that the transverse cutting slot defines an undulating cutting slot,
    a paddle member having a first mating surface configured to engage a non-resected bone surface of the bone in a first matching manner on account of a patient-specific nature of the first mating surface, the first matching manner registering a single relative position of the first mating surface relative to the non-resected bone surface of the bone, and
    a stabilizer member having a second mating surface configured to engage the non-resected bone surface of the bone in a second matching manner on account of a patient-specific nature of the second mating surface, the second matching manner registering a single relative position of the second mating surface relative to the non-resected bone surface of the bone, the first guide member is positioned inferior to the paddle member, and the stabilizer member is positioned inferior to the first guide member, wherein the stabilizer member has a first rail and a second rail each extending in an anterior-to-posterior direction, the second mating surface of the stabilizer member being positioned on inferior surfaces of the first rail and the second rail.

12. The cutting guide of claim 11, further comprising:
    a posterior surface having a mating surface configured to engage a non-resected surface of the bone in a matching manner on account of a patient-specific nature of the mating surface, the matching manner registering a single relative position of the mating surface relative to the non-resected bone surface.

13. The cutting guide of claim 12, wherein the bone is a tibia, and the arthroplasty procedure is an ankle arthroplasty procedure.

14. The cutting guide of claim 13, wherein the cutting guide further includes a second guide member coupled to the first guide member, the second guide member defining an angled guide surface angled obliquely to the transverse cutting slot.

15. The cutting guide of claim 14, wherein the mating surface has a first curvature that is curved posteriorly from a central area of the mating surface toward a medial and a lateral edge of the mating surface so that the central area of the mating surface is positioned anterior to the medial and lateral edges of the mating surface.

* * * * *